United States Patent
Kumar et al.

(10) Patent No.: US 11,021,527 B2
(45) Date of Patent: Jun. 1, 2021

(54) TRANSFORMING GROWTH FACTOR BETA RECEPTOR TYPE II FUSION POLYPEPTIDES

(71) Applicant: Acceleron Pharma Inc., Cambridge, MA (US)

(72) Inventors: Ravindra Kumar, Acton, MA (US); Dianne S. Sako, Medford, MA (US)

(73) Assignee: ACCELERON PHARMA INC., Cambridge, MA (US)

(*) Notice: Subject to any disclaimer, the term of this patent is extended or adjusted under 35 U.S.C. 154(b) by 0 days.

(21) Appl. No.: 15/969,957

(22) Filed: May 3, 2018

(65) Prior Publication Data

US 2018/0327477 A1 Nov. 15, 2018

Related U.S. Application Data

(60) Provisional application No. 62/501,229, filed on May 4, 2017, provisional application No. 62/510,422, filed on May 24, 2017, provisional application No. 62/578,674, filed on Oct. 30, 2017.

(51) Int. Cl.
  *C07K 14/71* (2006.01)
  *A61K 38/00* (2006.01)

(52) U.S. Cl.
  CPC .............. *C07K 14/71* (2013.01); *A61K 38/00* (2013.01); *C07K 2319/30* (2013.01)

(58) Field of Classification Search
  CPC ..... C07K 14/71; C07K 2319/30; A61K 38/00
  See application file for complete search history.

(56) References Cited

U.S. PATENT DOCUMENTS

| | | | |
|---|---|---|---|
| 5,543,143 A | 8/1996 | Reed | |
| 5,571,714 A | 11/1996 | Dasch et al. | |
| 5,662,904 A | 9/1997 | Ferguson et al. | |
| 5,693,607 A | 12/1997 | Segarini et al. | |
| 5,772,998 A | 6/1998 | Dasch et al. | |
| 5,783,185 A | 7/1998 | Dasch et al. | |
| 5,844,099 A | 12/1998 | Stahl et al. | |
| 6,001,969 A | 12/1999 | Lin et al. | |
| 6,008,011 A | 12/1999 | Lin et al. | |
| 6,046,157 A | 4/2000 | Lin et al. | |
| 6,090,383 A | 7/2000 | Dasch et al. | |
| 6,294,350 B1 | 9/2001 | Peterson | |
| 6,419,928 B1 | 7/2002 | Dasch et al. | |
| 6,630,326 B2 | 10/2003 | Markowitz et al. | |
| 6,998,125 B2 | 2/2006 | Hanna et al. | |
| 7,026,283 B2 | 4/2006 | Fleming et al. | |
| 7,786,261 B2 | 8/2010 | De Crescenzo et al. | |
| 7,795,389 B2 | 9/2010 | Sun et al. | |
| 7,867,496 B2 | 1/2011 | Khanna et al. | |
| 8,067,389 B2 | 11/2011 | Kumar et al. | |
| 8,283,449 B2 | 10/2012 | Galipeau et al. | |
| 8,318,135 B2 | 11/2012 | O'Connor-McCourt et al. | |
| 8,591,901 B2 | 11/2013 | Ledbetter et al. | |
| 8,658,135 B2 | 2/2014 | O'Connor-McCourt et al. | |
| 8,993,524 B2 | 3/2015 | Bedi et al. | |
| 9,676,863 B2 | 6/2017 | Lo | |
| 9,809,637 B2 | 11/2017 | Kumar et al. | |
| 9,884,900 B2 | 2/2018 | Kumar et al. | |
| 2002/0004037 A1 | 1/2002 | Koteliansky et al. | |
| 2004/0192583 A1 | 9/2004 | Medicherla et al. | |
| 2004/0234967 A1 | 11/2004 | Moskowitz | |
| 2005/0148555 A1 | 7/2005 | Gupta et al. | |
| 2005/0203022 A1 | 9/2005 | Gotwals et al. | |
| 2006/0286105 A1 | 12/2006 | Ledbetter et al. | |
| 2007/0014767 A1 | 1/2007 | Ezquerro Saenz et al. | |
| 2007/0077598 A1 | 4/2007 | Breit et al. | |
| 2008/0261879 A1 | 10/2008 | Melton et al. | |
| 2009/0004182 A1 | 1/2009 | Baiocchi et al. | |
| 2009/0036382 A1 | 2/2009 | Bressan et al. | |
| 2009/0042780 A1 | 2/2009 | Knopf et al. | |
| 2009/0186016 A1 | 7/2009 | Rade et al. | |
| 2010/0003256 A1 | 1/2010 | Lu et al. | |
| 2010/0008911 A1 | 1/2010 | Streisand et al. | |
| 2010/0204104 A1 | 8/2010 | Qiu et al. | |
| 2011/0008364 A1 | 1/2011 | Ledbetter et al. | |
| 2011/0104121 A1 | 5/2011 | Wira et al. | |
| 2011/0172296 A1 | 7/2011 | Bennett et al. | |
| 2011/0177070 A1 | 7/2011 | Lofquist et al. | |
| 2011/0236309 A1 | 9/2011 | O'Connor-Mccourt et al. | |
| 2011/0245107 A1 | 10/2011 | Kuchroo et al. | |

(Continued)

FOREIGN PATENT DOCUMENTS

CN  101852804 A  10/2010
EP  0 975 771 A1  2/2000

(Continued)

OTHER PUBLICATIONS

Abelsson et al., "Patients with polycythemia vera have worst impairment of quality of life among patients with newly diagnosed myeloproliferative neoplasms," Leuk Lymphoma, vol. 54(10):2226-2230 (2013).

Agarwal et al., "Bone marrow fibrosis in primary myelofibrosis: pathogenic mechanisms and the role of TGF-β," Stem Cell Investigation. vol. 3(5): 1-10. (General Review) (2016).

Akhurst et al., "Targeting the TGFβ signalling pathway in disease," Nature Review Drug Discovery. vol. 11(10): 790-810 (2012).

Alvarez-Larran et al., "JAK2V617F monitoring in polycythemia vera and essential thrombocythemia: Clinical usefulness for predicting myelofibrotic transformation and thrombotic events," *Am J Hematol* vol. 89(5):517-523 (2014).

(Continued)

*Primary Examiner* — Robert S Landsman
(74) *Attorney, Agent, or Firm* — White & Case LLP

(57) ABSTRACT

In certain aspects, the present disclosure relates to TβRII fusion polypeptides comprising a heterologous portion and a truncated, ligand-binding portion of the extracellular domain of TβRII polypeptide useful to selectively antagonize a TβRII ligand. The disclosure further provides compositions and methods for use in treating or preventing TGFβ associated disorders.

4 Claims, 11 Drawing Sheets
(9 of 11 Drawing Sheet(s) Filed in Color)
Specification includes a Sequence Listing.

(56) References Cited

U.S. PATENT DOCUMENTS

| | | |
|---|---|---|
| 2011/0319406 A1 | 12/2011 | Kim et al. |
| 2012/0010178 A1 | 1/2012 | Rubin et al. |
| 2012/0114640 A1 | 5/2012 | Kulkarni et al. |
| 2013/0011397 A1 | 1/2013 | Pasricha |
| 2013/0039911 A1 | 2/2013 | Bedi et al. |
| 2013/0045272 A1 | 2/2013 | Niitsu et al. |
| 2013/0287688 A1 | 10/2013 | Jain et al. |
| 2013/0287802 A1 | 10/2013 | Govindappa et al. |
| 2015/0056199 A1 | 2/2015 | Kumar et al. |
| 2015/0080320 A1 | 3/2015 | Desai |
| 2015/0225483 A1 | 8/2015 | Lo |
| 2016/0017026 A1 | 1/2016 | Wei et al. |
| 2016/0287664 A1 | 10/2016 | Yu et al. |
| 2016/0298093 A1 | 10/2016 | Kumar et al. |
| 2016/0376341 A1 | 12/2016 | Kumar et al. |
| 2017/0158770 A1 | 6/2017 | Bedi et al. |
| 2017/0202918 A1 | 7/2017 | Yung et al. |
| 2018/0118832 A1 | 5/2018 | Lo et al. |

FOREIGN PATENT DOCUMENTS

| | | |
|---|---|---|
| JP | 2016-037488 A | 3/2016 |
| WO | WO-91/19513 A1 | 12/1991 |
| WO | WO-98/48024 A1 | 10/1998 |
| WO | WO-1998/048024 A1 | 10/1998 |
| WO | WO-99/65948 A1 | 12/1999 |
| WO | WO-01/66140 A1 | 9/2001 |
| WO | WO-03/011908 A2 | 2/2003 |
| WO | WO-03/061587 A2 | 7/2003 |
| WO | WO-04/098637 A1 | 11/2004 |
| WO | WO-2005/019258 A2 | 3/2005 |
| WO | WO-06/036729 A2 | 4/2006 |
| WO | WO-2008/060371 A1 | 5/2008 |
| WO | WO-2008/157367 A1 | 12/2008 |
| WO | WO-2009/026204 A1 | 2/2009 |
| WO | WO-2010/003118 A1 | 1/2010 |
| WO | WO-2010/083034 A1 | 7/2010 |
| WO | WO-2011/109789 A2 | 9/2011 |
| WO | WO-2012/030394 A1 | 3/2012 |
| WO | WO-2012/093125 A1 | 7/2012 |
| WO | WO-2012/145539 A1 | 10/2012 |
| WO | WO-2013/000234 A1 | 1/2013 |
| WO | WO-2013/012648 A1 | 1/2013 |
| WO | WO-2013/019805 A1 | 2/2013 |
| WO | WO-2013/059879 A1 | 5/2013 |
| WO | WO-2013/164694 A1 | 11/2013 |
| WO | WO-2014/164427 A1 | 10/2014 |
| WO | WO-2014/172584 A1 | 10/2014 |
| WO | WO-2015/027082 A1 | 2/2015 |
| WO | WO-2015/077540 A2 | 5/2015 |
| WO | WO-2015/179227 A1 | 11/2015 |
| WO | WO-2015/189790 A1 | 12/2015 |
| WO | WO-2016/019368 A1 | 2/2016 |
| WO | WO 2016/164501 A1 | 10/2016 |
| WO | WO-2017/024171 A1 | 2/2017 |
| WO | WO-2017/037634 A1 | 3/2017 |
| WO | WO-2017/134592 A1 | 8/2017 |
| WO | WO-2018/064190 A1 | 4/2018 |
| WO | WO-2018/129331 A1 | 7/2018 |
| WO | WO-2018/158727 A1 | 9/2018 |
| WO | WO-2019/157342 A1 | 8/2019 |

OTHER PUBLICATIONS

Barbui et al., "Disease characteristics and clinical outcome in young adults with essential thrombocythemia versus early/prefibrotic primary myelofibrosis," Blood vol. 120(3):569-571 (2012).
Barbui et al., "Thrombosis in primary myelofibrosis: incidence and risk factors," Blood, vol. 115(4): 778-782 (2010).
Barbui et al., "Masked polycythemia vera diagnosed according to WHO and BCSH classification," American Journal Hematology, vol. 89(2):199-202 (2014).
Barbui et al., "Front-line therapy in polycythemia vera and essential thrombocythemia," Blood Reviews, vol. 26: 205-211 (2012).
Barbui et al., "Rethinking the diagnostic criteria of polycythemia vera," Leukemia, vol. 28: 1191-1195 (2014).
Barosi et al., "JAK2 V617F mutational status predicts progression to large splenomegaly and leukemic transformation in primary myelofibrosis," Blood, vol. 110 (12): 4030-4036 (2007).
Barosi et al., "Therapeutic approaches in myelofibrosis," Expert Opin Pharmacother, vol. 12(10): 1597-1611 (2011).
Barosi et al., "Proposed criteria for the diagnosis of post-polycythemia vera and post-essential thrombocythemia myelofibrosis: a consensus statement from the international working group for myelofibrosis research and treatment," Leukemia, vol. 22:437-438 (2008).
Baxter et al., "Acquired mutation of the tyrosine kinase JAK2 in human myeloproliferative disorders," Lancet, vol. 365:1054-1061 (2005).
Begna et al., "A phase-2 trial of low-dose pomalidomide in myelofibrosis," Leukemia, vol. 25:301-304 (2011).
Birgegard G., "Advances and challenges in the management of essential thrombocythemia," Therapeutics Advances Hematology, vol. 6 (3): 142-156 (2015).
Bunn, "Drug-induced autoimmune red-cell aplasia," New England Journal of Medicine, vol. 346(7): 522-523 (2002).
Campbell et al., "Definition of subtypes of essential thrombocythaemia and relation to polycythaemia vera based on JAK2 V617F mutation status: a prospective study," Lancet, vol. 366:1945-1953 (2005).
Campbell et al., "The Myeloproliferative Disorders," N Engl J Med, vol. 355:2452-2466 (2006).
Carbuccia et al., "Mutations of ASXL1 gene in myeloproliferative neoplasms," Leukemia, vol. 23:2183-2186 (2009).
Cervantes et al., "New prognostic scoring system for primary myelofibrosis based on a study of the International Working Group for Myelofibrosis Research and Treatment," Blood, vol. 113(13):2895-2901 (2009).
Chagraoui et al., "Prominent role of TGF-β1 in thrombopoietin-induced myelofibrosis in mice," Blood, vol. 100(10): 3495-3503 (2002).
Chou et al., "Leukocytosis in polycythemia vera and splenomegaly in essential thrombocythemia are independent risk factors for hemorrhage," European Journal of Haematology, vol. 90:228-236 (2013).
Dahabreh et al., "Is JAK2 V617F mutation more than a diagnostic index? A meta-analysis of clinical outcomes in essential thrombocythemia," Leukemia Research, vol. 33: 67-73 (2009).
Database Geneseq [Online] "Il-6xR/TNF-alpha binding multispecific xceptor fusion protein, SEQ 735," retrieved from EBI accession No. GSP:AXU77688 (Apr. 1, 2010).
Delanty et al., "Erythropoietin-associated hypertensive posterior leukoencephalopathy," Neurology, vol. 49: 686-689 (1997).
Delhommeau et al., "Mutation in TET2 in Myeloid Cancers," N Engl J Med, vol. 360(22):2289-2301 (2009).
Del Re et al., "In the absence of type III receptor, the transforming growth factor (TGF)-β type II-B receptor requires the type I receptor to bind TGF-β2," J Biol Chem, vol. 279(21): 22765-22772 (2004).
Dennler et al, "Direct binding of Smad3 and Smad4 to critical TGFβ-inducible elements in the promoter of human plasminogen activator inhibitor-type 1 gene," EMBO, vol. 17(11): 3091-3100 (1998).
Dong and Blobe, "Role of transforming growth factor-β in hematologic malignancies," Blood, vol. 107(12): 4589-4596 (2006).
Druker et al., "Efficacy and Safety of a Specific Inhibitor of the BCR-ABL Tyrosine Kinase in Chronic Myeloid Leukemia," N Engl J Med, vol. 344(14):1031-1037 (2001).
Elliott et al., "Splenic irradiation in myelofibrosis with myeloid metaplasia: a review, "Blood Reviews, vol. 13(3):163-170 (1999).
Emanuel et al., "Myeloproliferative Neoplasm (MPN) Symptom Assessment Form Total Symptom Score: Prospective International Assessment of an Abbreviated Symptom Burden Scoring System Among Patients with MPNs," J Clin Oncol, vol. 30(33): 4098-4103 (2012).
Faoro et al., "Long-term analysis of the palliative benefit of 2-chlorodeoxyadenosine for myelofibrosis with myeloid metaplasia, "Eur J Haematol, vol. 74(2): 117-120 (2005).

(56) References Cited

OTHER PUBLICATIONS

Finazzi et al., "Acute leukemia in polycythemia vera: an analysis of 1638 patients enrolled in a prospective observational study," *Blood*, vol. 105(7):2664-2670 (2005).
Finazzi et al., "How I treat patients with polycythemia vera," *Blood*, vol. 109(12):5104-5111 (2007).
Gangat et al., "Mutations and thrombosis in essential thrombocythemia: prognostic interaction with age and thrombosis history," *Eur J Haematol*, vol. 94: 31-36 (2014).
Gastinne et al., "Adenoviral-mediated TGF-β1 inhibition in a mouse model of myelofibrosis inhibit bone marrow fibrosis development," Experimental Hematology, vol. 35, Issue 1: 64-74; , p. 67, Retroviral transfer in SCID mice BM cells is highly efficient, p. 68, Histological analysis (2007).
Grobet et al., "A deletion in the bovine myostatin gene causes the double-muscled phenotype in cattle," Nat Genet, vol. 17 (1): 71-74 (1997).
Guglielmelli et al., "Safety and efficacy of everolimus, a mTOR inhibitor, as single agent in a phase 1/2 study in patients with myelofibrosis," *Blood*, vol. 118(8):2069-2076 (2011).
Gupta et al., "Allogeneic hematopoietic cell transplantation for myelofibrosis in the era of JAK inhibitors," *Blood*, vol. 120(7):1367-1379 (2012).
Harrison et al., "Prodomains regulate the synthesis, extracellular localisation and activity of TGF-β superfamily ligands," Growth Factors, vol. 29(5): 174-186 (2011).
Hensley et al., "Polycythemia vera: current pharmacotherapy and future directions," Expert Opin Pharmacotherapy, vol. 14:609-617 (2013).
Hirai and Fijita, "A Human Transforming Growth Factor-beta Type II Receptor that Contains an Insertion in the Extracellular Domain," Ex. Cell Res., vol. 223: 135-141 (1996).
Horl et al., "European Best Practice Guidelines 17-18 Adverse effects," *Nephrol Dial Transplant*, vol. 15 (suppl. 4), 51-56 (2000).
Hussein et al., "Conventional cytogenetics in myelofibrosis: literature review and discussion," *Eur J Haematology*, vol. 82:329-338 (2009).
Hussein et al., "International Prognostic Scoring System-independent cytogenetic risk categorization in primary myelofibrosis," *Blood*, vol. 115(3):496-499 (2010).
Isaka et al., "Gene therapy by transforming growth factor-β receptor-IgG Fc chimera suppressed extracellular matrix accumulation in experimental glomerulonephritis," Kidney International, vol. 55(2): 467-475 (1999).
James et al., "A unique clonal JAK2 mutation leading to constitutive signaling causes polycythaemia vera," Nature, vol. 434: 1144-1148 (2005).
Klampfl et al., Somatic Mutations of Calreticulin in Myeloproliferative Neoplasms, *N Engl J Medicine*, vol. 369(25): 2379-2390 (2013).
Komesli et al., "Chimeric extracellular domain of type II transforming growth factor (TGF)-β receptor fused to the Fc region of human immunoglobulin as a TGF-β antagonist," Eur. J. Biochem., vol. 254: 505-513 (1998).
Konrad et al., "Alternative splicing of TGF-betas and their high-affinity receptors TβRI, TβRII and TβRIII (betaglycan) reveal new variants in human prostatic cells," BMC Genomics, vol. 8: 318 (2007).
Kontani et al., "Spontaneous elicitation of potent antitumor immunity and eradication of established tumors by administration of DNA encoding soluble transforming growth factor-b II receptor without active antigen-sensitization," Cancer Immunol. Immunother; vol. 55: 579-587 (2006).
Kralovics et al., "A Gain-of-Function Mutation of JAK2 in Myeloproliferative Disorders," *N Engl J Medicine*, vol. 352(17): 1779-1790 (2005).
Kvasnicka et al., "Prodromal myeloproliferative neoplasms: The 2008 WHO classification," *Am J Hematology*, vol. 85:62-69 (2010).

Lasho et al., "SRSF2 mutations in primary myelofibrosis: significant clustering with IDH mutations and independent association with inferior overall and leukemia-free survival," *Blood*, vol. 120 (20):4168-4171 (2012).
Levine et al., "Activating mutation in the tyrosine kinase JAK2 in polycythemia vera, essential thrombocythemia, and myeloid metaplasia with myelofibrosis," *Cancer Cell*, vol. 7:387-397 (2005).
Levine et al., "Role of JAK2 in the pathogenesis and therapy of myeloproliferative disorders," *Nat Rev Cancer*, vol. 7:673-683 (2007).
Lin et al. "Expression cloning of the TGF-β type II receptor, a functional transmembrane serine/threonine kinase," Cell, vol. 68(4): 775-785 (1992).
Lussana et al., "Association of V617F Jak2 mutation with the risk of thrombosis among patients with essential thrombocythaemia or idiopathic myelofibrosis: A systematic review," *Thrombosis Research*, vol. 124: 409-417 (2009).
Manoharan et al., "The Reticulin Content of Bone Marrow in Acute Leukaemia in Adults," *Br J Haematology*, vol. 43: 185-190 (1979).
Martinez-Trillos et al., "Efficacy and tolerability of hydroxyurea in the treatment of the hyperproliferative manifestations of myelofibrosis: results in 40 patients," *Ann Hematol.*, vol. 89(12):1233-1237 (2010).
Mascarenhas et al., "Advances in myelofibrosis: a clinical case approach," Haematologica, vol. 98(10): 1499-1509 (2013).
Mascarenhas et al., "Biology and Clinical Management of Myeloproliferative Neoplasms and Development of the JAK Inhibitor Ruxolitinib," *Current Medical Chemistry*, vol. 19:4399-4413 (2012).
Mascarenhas et al., "Anti-transforming growth factor-β therapy in patients with myelofibrosis," Leukemia & Lymphoma. vol. 55(2): 450-452 (2014).
Mascarenhas et al. "Prolonged Low Dose Therapy with a Pan-Deacetylase Inhibitor, Panobinostat (LBH589), in Patients with Myelofibrosis," Blood, The Journal of American Society of Hematology, vol. 118(Suppl.1) (2011).
Massagué, J., "How cells read TGF-beta signals," Nat. Rev. Mol. Cell Biol. 1(3): 169-178 (2000).
McMullin et al., "Amendment to the guideline for diagnosis and investigation of polycythaemia/erythrocytosis," British Journal Haematology, vol. 138:812-823 (2007).
Mehta et al., "Epidemiology of myeloproliferative neoplasms in the United States," *Leukemia & Lymphoma*, vol. 55:595-600 (2014).
Mesa et al., "Phase1/-2 study of pomalidomide in myelofibrosis," Am J. Hemtatol, vol. 85:129-130 (2010).
Mesa, R.A., "How I treat symptomatic splenomegaly in patients with myelofibrosis," *Blood*, vol. 113(22):5394-5400 (2009).
Mesa, R.A., "The evolving treatment paradigm in myelofibrosis," *Leukemia & Lymphoma*. vol. 54(2):242-251 (2013).
Murphy, Scott, "Diagnostic Criteria and Prognosis in Polycythemia Vera and Essential Thrombocythemia," Seminars in Hematology, vol. 36(1), Suppl. 2: 9-13 (1999).
Nangalia et al., "Somatic CALR Mutations in Myeloproliferative Neoplasms with Nonmutated JAK2," The New England Journal of Medicine, vol. 369 (25): 2391-2405 (2013).
Nikawa, Jun-ichi, "A cDNA encoding the human transforming growth factor β receptor suppresses the growth defect of yeast mutant," Gene, vol. 149: 367-372 (1994).
Oh et al., "Novel mutations in the inhibitory adaptor protein LNK drive JAK-STAT signaling in patients with myeloproliferative neoplasms," *Blood*, vol. 116(6):988-992 (2010).
O'Shea et al., "Janus Kinase Inhibitors in autoimmune diseases," Ann. Rheum Dis., vol. 72(0 2): ii111-115 (2013).
Passamonti et al., "Life Expectancy and Prognostic Factors for Survival in Patients with Polycythemia Vera and Essential Thrombocythemia," *Am J Med*, vol. 117:755-761 (2004).
Passamonti et al., "Clinical Relevance of JAK2 (V617F) Mutant Allele Burden," *Haematologica*, vol. 94 (6 pages) (2009).
Passamoti et al., "A dynamic prognostic model to predict survival in primary myelofibrosis: a study by the IWG-MRT (International Working Group for Myeloproliferative Neoplasms Research and Treatment)," *Blood*, vol. 115(9): 1703-1708 (2010).
Passamonti et al., "A prospective study of 338 patients with polycythemia vera: the impact of JAK2 (V617F) allele burden and leukocytosis on

(56) References Cited

OTHER PUBLICATIONS fibrotic or leukemic disease transformation and vascular complications," *Leukemia*, vol. 24:1574-1579 (2010).
Passamonti et al., "A prognostic model to predict survival in 867 World Health Organization-defined essential thrombocythemia at diagnosis: a study by the International Working Group on Myelofibrosis Research and Treatment," *Blood*, vol. 120(6):1197-1201 (2012).
Passamonti F., "How I treat polycythemia vera," *Blood*, vol. 120(2):275-284 (2012).
Patnaik et al., "Age and platelet count are IPSS-independent prognostic factors in young patients with primary myelofibrosis and complement IPSS in predicting very long or very short survival," *European Journal of Haemotology*, vol. 84:105-108 (2010).
Pikman et al., "MPLW515L Is a Novel Somatic Activating Mutation in Myelofibrosis with Myeloid Metaplasia," *PLOS Medicine*, vol. 3:e270 (2006).
Quintas-Cardama et al., "Janus kinase inhibitors for the treatment of myeloproliferative neoplasias and beyond," *Nature Reviews Drug Discovery*, vol. 10:127-140 (2011).
R&D Systems, Recombinant Human TGF-β RBII Fc Chimera, Catalog No. 341-BR (2015).
R&D Systems, Recombinant Human TGF-β RI Isoform 2 Fc Chimera Catalog No. 1003-RT (2015).
Radaev et al., "Ternary complex and transforming growth factor-β1 reveals isoform-specific ligand recognition and receptor recruitment in the superfamily," J Biol Chem, vol. 285(19):14806-14814 (2010).
Rotunno et al., "Impact of calreticulin mutations on clinical and hematological phenotype and outcome in essential thrombocythemia," *Blood*, vol. 123(10):1552-1555 (2014).
Rotzer et al., "Type III TGF-β receptor-independent signaling of TGFβ2 via TβRII-B, an alternatively spliced TGF-β type II receptor," The EMBO Journal, vol. 20(3): 480-490 (2001).
Rumi et al., "CALR exon 9 mutations are somatically acquired events in familial cases of essential thrombocythemia or primary myelofibrosis," *Blood*, vol. 123(15):2416-2419 (2014).
Scherber et al., "The Myeloproliferative Neoplasm Symptom Assessment Form (MPN-SAF): International Prospective Validation and Reliability Trial in 402 patients," *Blood*, vol. 118(2):401-408 (2011).
Schuelke et al., " Myostatin mutation associated with gross muscle hypertrophy in a child," N Engl J Med vol. 350(26): 2682-26888 (2004).
Scott et al., "JAK2 Exon 12 Mutations in Polycythemia Vera and Idiopathic Erthrocytosis," New England Journal of Medicine, vol. 356(5):459-468 (2007).
Sever et al., "Therapeutic options for patients for polycythemia vera and essential thrombocythemia refractory/resistant to hydroxyurea," *Leukemia & Lymphoma*, vol. 55(12):2685-2690 (2014).
Shi et al., "Latent TGF-β structure and activation," Nature, vol. 474(7351): 343-349 (2011).
Singbartl et al., "Erythropoietin and Autologous Transfusion: Adverse events of erythropoietin in long-term and in acute/short-term treatment," *Journal Clin Investig*, vol. 72(suppl 6), S36-S43 (1994).
Sonbol et al., "Comprehensive review of JAK inhibitors in myeloproliferative neoplasms," Therapeutic Advances in Hematology, vol. 4(1): 15-35 (2013).
Spivak, J.L., "Polycythemia vera: myths, mechanisms, and management," *Blood*, vol. 100 (13):4272-4290 (2002).
Stuart et al., "Polycythemia Vera," *Am Fam Physician* 69:2139-2144 (2004).
Suzuki et al., "Cloning of an isoform of mouse TGF-β type II receptor gene," FEBS Letters, vol. 335: 19-22 (1994).
Talarico et al., "Myeloproliferative disorders: a practical review," *Patient Care*, vol. 30:37-57 (1998).
Tefferi et al., "Proposals and rationale for revision of the World Health Organization diagnostic criteria for polycythemia vera, essential thrombocythemia, and primary myelofibrosis: recommendations from an ad hoc international expert panel," *Blood*, vol. 110(4):1092-1 097 (2007).

Tefferi et al., "CALR and ASXL1 mutations-based molecular prognostication in primary myelofibrosis: an international study of 570 patients," Leukemia, vol. 28:1494-1500 (2014).
Tefferi, A., "Primary myelofibrosis: 2012 update on diagnosis, risk stratification, and management," *Am J Hematology*, vol. 86(12): 1017-1026 (2011).
Tefferi, A., "How I treat myelofibrosis," *Blood* 117(13):3494-3504 (2011).
Tefferi, A., "Mutations galore in myeloproliferative neoplasms: Would the real Spartacus please stand up?," Leukemia, vol. 25: 1059-1063 (2011).
Tefferi et al., "CALR vs JAK2 vs MPL-mutated or triple-negative myelofibrosis: clinical, cytogenetic and molecular comparisons," Leukemia, vol. 28: 1472-1477 (2014).
Tefferi et al., "CME Information: Primary myelofibrosis: 2014 update on diagnosis, risk-stratification and management," *Am J Hematol*, vol. 89(9):915-925 (2014).
Tefferi et al., "The JAK2V617F tyrosine kinase mutation in myelofibrosis with myeloid metaplasia: lineage specificity and clinical correlates," British Journal Haematology, vol. 131:320-328 (2005).
Tefferi et al., "Lenalidomide therapy in del(5)(q31)-associated myelofibrosis: cytogenetic and JAK2V617F molecular remissions," *Leukemia*, vol. 21(8): 1827-1828 (2007).
Tefferi et al., "Thrombosis in Myeloproliferative Disorders: Prevalence, Prognostic Factors, and the Role of Leukocytes and JAK2V617F," Seminars in Thrombosis and Hemostasis, vol. 33:313-320 (2007).
Tefferi et al., "Transfusion-dependency at presentation and its acquisition in the first year of diagnosis are both equally detrimental for survival in primary myelofibrosis-prognostic relevance is independent of IPSS or karyotype," American Journal of Hematology, vol. 85:14-17 (2009).
Tefferi et al., "Predictors of greater than 80% 2-year mortality in primary myelofibrosis: a Mayo Clinic study of 884 karyotypically annotated patients," Blood, vol. 118:4595-4598 (2011).
Tefferi et al., "IDH mutations in primary myelofibrosis predict leukemic transformation and shortened survival: clinical evidence for leukemogenic collaboration with JAK2V617F," Leukemia, vol. 26: 475-480 (2012).
Tefferi et al., "Survival and prognosis among 1545 patients with contemporary polycythemia vera: an international study," *Leukemia*, vol. 27:1874-1881 (2013).
Tefferi et al., "Calreticulin mutations and long-term survival in essential thrombocythemia," *Leukemia*, vol. 28: 2300-2303 (2014).
Thapaliya et al., "International working group for myelofibrosis research and treatment response assessment and long-term follow-up of 50 myelofibrosis patients treated with thalidomide-prednisone based regiments," *Am J Hematology*, vol. 86(1):96-98 (2011).
Thiele et al., "European consensus on grading bone marrow fibrosis and assessment of cellularity," Haematologica, vol. 90:1128-1132 (2005).
Thiele et al., WHO Classification of Tumours of Haematopoietic and Lymphoid Tissues. IARC Lyon: World Health Organization, 44-47 (2008).
Tibes et al., "Emerging drugs for polycythemia vera," Expert Opinion, vol. 18:393-404 (2013).
Vannucchi et al., "A pathobiologic pathway linking thrombopoietin, GATA-1, and TGF-β1 in the development of myelofibrosis," Blood, vol. 105 (9): 3493-3501 (2005).
Vannucchi A.M., "Insights into the pathogenesis and management of thrombosis in polycythemia vera and essential thrombocythemia," Intern Emerg Med, vol. 5: 177-184 (2010).
Vannucchi et al., "The mTOR Inhibitor, RAD001, Inhibits the Growth of Cells From Patients with Myeloproliferative Neoplasms," Blood. vol. 114(22):2914 (2009).
Vannucchi et al., "Management of Myelofibrosis," American Society of Hematology, Current Issues in Myeloproliferative Neoplasms:222-230 (2011).
Wrana et al., "TGFβ 3 signals through a heteromeric protein kinase receptor complex," Cell vol. 71(6): 1003-1014 (1992).
Wynn, Thomas A., "Common and unique mechanisms regulate fibrosis in various fibroproliferative diseases," The Journal of Clinical Investigation, vol. 117(3):524-529 (2007).

(56) References Cited

OTHER PUBLICATIONS

Xing et al., "Transgenic expression of JAK2V617F causes myeloproliferative disorders in mice," Blood, vol. 111(10): 5109-5117 (2008).
Xu et al., JAK2V617F: prevalence in a large Chinese hospital population, Blood, vol. 109(1):339-342 (2007).
Xin et al., "Suppression of Cyclosporine a Nephrotoxicity in Vivo by Transforming Growth Factor β Receptor-Immunoglobulin G. Chimeric Protein," Transplantation, vol. 77(9): 1433-1442 (2004).
Yan et al., "A Model of Myelofibrosis and Osterosclerosis in Mice Induced by Overexpressing Thrombopoietin (mpl Ligand): Reversal of Disease by Bone Marrow Transplantation," Blood, vol. 88(2): 402-409 (1996).
Yavorkovsky et al., "Correspondence: Classifying Chronic Myelomonocytic Leukemia," Journal of Clinical Oncology, vol. 19(17):3790-3792 (2001).
Zahr et al., "Bone marrow fibrosis in myelofibrosis: pathogenesis, prognosis and targeted strategies," Haematologica, vol. 101(6): 660-671 (2016).
Zauli et al., "Reduced responsiveness of bone marrow megakaryocyte progenitors to platelet-derived transforming growth factor β1, produced in normal amount, in patients with essential thromboycythamia," Br J Haematol, vol. 83(1): 14-20 (1993).
Zwaagstra et al., "Engineering and Therapeutic Application of Single-Chain Bivalent TGF-β Family Traps," Molecular Cancer Therapeutics, vol. 11(7): 1477-1487 (2012).
Ziakas P., "Effect of JAK2 V617F on thrombotic risk in patients with essential thrombocythemia: measuring the uncertain," Haematologica, vol. 93(9): 1412-1414 (2008).
Akhurst et al., "Targeting the TGFβ signalling pathway in disease," Nature Reviews Drug Discovery, vol. 11(10):790-811 (2012).
Anderton et al., "Induction of heart valve lesions by small-molecule ALK5 inhibitors," Toxicologic Pathology, vol. 39(6):916-924 (2011).
Anonymous: "TGF[beta]1 Antagonist Inhibits Fibrosis in a Murine Model of Myelofibrosis—Acceleron Pharma, Inc.", pp. 1-2 (2015).
Aschner et al., "Transforming Growth Factor-β: Master Regulator of the Respiratory System in Health and Disease," American Journal of Respiratory Cell and Molecular Biology, vol. 54(5):647-655 (2016).
Bock et al., "Identification of new target molecules PTK2, TGFBR2 and CD9 overexpressed during advanced bone marrow remodelling in primary myelofibrosis," British Journal of Haematology, vol. 146(5): 510-520 (2009).
Botney et al., "Vascular Remodeling in Primary Pulmonary Hypertension: Potential Role for Transforming Growth Factor-β," American Journal of Pathology, vol. 144(2):286-295 (1994).
Cao et al., "Changes of calponin and TGFβ1 in pulmonary artery smooth muscle of pulmonary artery hypertension rats." Chinese Pharmacological Bulletin 23(2):277-278 (2007).
Chen et al., "Dominant negative mutation of the TGF-β receptor blocks hypoxia-induced pulmonary vascular remodeling," Journal of Applied Physiology, vol. 100:564-571 (2006).
Czajkowsky et al., "Fc-fusion proteins: new developments and future perspectives," EMBO Molecular Medicine, vol. 4(10):1015-1028 (2012).
Derrett-Smith et al., "Endothelial Injury in a Transforming Growth Factor β-Dependent Mouse Model of Scleroderma Induces Pulmonary Arterial Hypertension," Arthritis & Rheumatism, vol. 65(11):2928-2939 (2013).
Gäbler et al., "JAK2 mutants (e.g., JAK2V617F) and their importance as drug targets in myeloproliferative neoplasms," JAK-STAT, vol. 2(3): p. e250525 (2013).
Gong et al., "Hypoxia induces downregulation of PPAR-α in isolated pulmonary arterial smooth muscle cells and in rat lung via transforming growth factor-β signaling," American Journal of Physiology-Lung Cellular and Molecular Physiology, vol. 301(6):L899-L907 (2011).
Gonzalez-Nunez et al., "The ALK-1/SMAD1 pathway in cardiovascular physiopathology. A new target for therapy?," Biochimica Biophysica Acta, vol. 1832(10):1492-1510 (2013).
Gordon et al., "Role of transforming growth factor-β superfamily signaling pathways in human disease," Biochimica et Biophysica Acta, vol. 1782(4):197-228 (2008).
Grafe et al., "Excessive TGFβ signaling is a common mechanism in Osteogenesis Imperfecta," Nature Medicine, vol. 20(6):670-675 (2014).
Graham et al., "Transforming Growth Factor-β Signaling Promotes Pulmonary Hypertension Caused by Schistosoma Mansoni," Circulation, vol. 128:1354-1364 (2013).
Harrison et al., "Transforming Growth Factor-β Receptor Mutations and Pulmonary Arterial Hypertension in Childhood," Circulation, vol. 111:435-441 (2005).
Hatton et al., "Transforming growth factor signalling: a common pathway in pulmonary arterial hypertension and systemic sclerosis," International Journal of Clinical Practice 65:35-43 (2011).
Jasinska-Stroschein et al., "The current approach into signaling pathways in pulmonary arterial hypertension and their implications in novel therapeutic strategies," Pharmacological Reports 1-13 (2014).
Long et al., "Altered Bone Morphogenetic Protein and Transforming Growth Factor-≠ Signaling in Rat Models of Pulmonary Hypertension: Potential for Activin Receptor-Like Kinase-5 Inhibition in Prevention and Progression of Disease," Circulation, vol. 119:566-576 (2009).
Meadows et al., "Increased expression of growth differentiation factor-15 in systemic sclerosis-associated pulmonary arterial hypertension," Chest, vol. 139(5):994-1002 (2011).
Megalou et al., "Transforming growth factor-beta inhibition and endothelin receptor blockade in rats with monocrotaline-induced pulmonary hypertension," Pulmonary Circulation, vol. 2(4): 461-469 (2012).
Megalou et al., "Transforming growth factor-β inhibition attenuates pulmonary arterial hypertension in rats," Int. J. Clin, Exp. Med., vol. 3(4): 332-340 (2010).
Montani et al., "Targeted therapies in pulmonary arterial hypertension," Pharmacology & Therapeutics 141:172-191 (2014).
Nasim et al., "BMPR-II deficiency elicits pro-proliferative and anti-apoptotic responses through the activation of TGFβ TAK1-MAPK pathways in PAH," Human Molecular Genetics, vol. 21(11):2548-2558 (2012).
Ogo et al., "Inhibition of Overactive Transforming Growth Factor-β Signaling by Prostacyclin Analogs in Pulmonary Arterial Hypertension," American Journal of Respiratory Cell and Molecular Biology, vol. 48(6):733-741 (2013).
Perkett et al., "Transforming Growth Factor-β Activity in Sheep Lung Lymph during the Development of Pulmonary Hypertension," Journal of Clinical Investigation, vol. 86:1459-1464 (1990).
Rabbani et al., "Soluble TGFβ Type II Receptor Gene Therapy Ameliorates Acute Radiation-Induced Pulmonary Injury in Rats", International Journal of Radiation Oncology, Biology, Physics, vol. 57(2):563-572 (2003).
Rainer et al., "Cardiomyocyte-Specific Transforming Growth Factor β Suppression Blocks Neutrophil Infiltration, Augments Multiple Cytoprotective Cascades, and Reduces Early Mortality After Myocardial Infarction," Circulation Research, vol. 114:1246-1257 (2014).
Samuel et al., "Serelaxin Is a More Efficacious Antifibrotic Than Enalapril in an Experimental Model of Heart Disease," Hypertension, vol. 64:315-322 (2014).
Suragani, R Nvs et al: "605: TGFb1 Antagonist Inhibits Fibrosis in a Murine Model of Myelofibrosis," 1-3 (2015).
Suragani, Rajasekhar Nvs, "Murine TGF[beta]-antagonist (RAP-1332) Inhibits Fibrosis in a Murine Model of Myelofibrosis," pp. 1-18, 2015.
Thomas et al., "Activin-like kinase 5 (ALK5) mediates abnormal proliferation of vascular smooth muscle cells from patients with familial pulmonary arterial hypertension and is involved in the progression of experimental pulmonary arterial hypertension induced by monocrotaline," The American Journal of Pathology, vol. 174(2):380-389 (2009).

(56) References Cited

OTHER PUBLICATIONS

Upton et al., "The transforming growth factor-β-bone morphogenetic protein type signalling pathway in pulmonary vascular homeostasis and disease," Experimental Physiology, vol. 98(8):1262-1266 (2013).

Upton et al., "Transforming Growth Factor-β1 Represses Bone Morphogenetic Protein-Mediated Smad Signaling in Pulmonary Artery Smooth Muscle Cells via Smad3," American Journal of Respiratory Cell and Molecular Biology, vol. 49(6):1135-1145 (2013).

Yung et al., "Abstract 17285: A Selective Transforming Growth Factor-β and Growth Differentiation Factor-15 Ligand Trap Attenuates Pulmonary Hypertension," Circulation 130:A17285 (2014) (4 pages).

Zaiman et al., "Role of the TGF-β/ALK5 Signaling Pathway in Monocrotaline-induced Pulmonary Hypertension," American Journal of Respiratory and Critical Care Medicine, vol. 177:896-905 (2008).

Raju T.S., "Glycosylation Variations with Expression Systems and Their Impact on Biological Activity of Therapeutic Immunoglobulines," BioProcess International: 44-53 (2003).

Yung et al., "A selective transforming growth factor-B ligand trap attenuates pulmonary hypertension," American Journal of Respiratory and Critical Care Medicine, vol. 194(9): 1140-1151 (2016).

Gupta et al., "Connective tissue growth factor: Potential role in glomerulosclerosis and tubulointerstitial fibrosis," Kidney International, vol. 58: 1389-1399 (2000).

Varga et al., "Transforming growth factor-β as a therapeutic target in systemic sclerosis," Nat Rev Rheumatol. vol. 5(4): 200-206 (2009).

Li, et al., "Purification and Biological Characterization of the Fusion Protein TGF-β RII/Fc", Chin J. Cell Mol Immunol 19(4), p. 400-405, 2003 (English Translation).

Li, et al., "Construction of eukaryotic expression vector of fusion gene TGF-βRII/Fc and its expression in CHO cells", J Fourth Mil Med Univ 23(4), 2003 (English Translation).

Li, et al., "Expression of fusion gene TGF-βRII/Fc in Bac-to-Bac baculovirus expression system", J. Fourth Mil Med Univ 24(4), 2003 (English Translation).

```
  1  mgrgllrglw plhivlwtri astipphvqk svnndmivtd nngavkfpql
 51  ckfcdvrfst cdnqkscmsn csitsicekp qevcvavwrk ndenitletv
101  chdpklpyhd filedaaspk cimkekkkpg etffmcscss decndniifs
151  eeyntsnpdl llvifqvtgi sllpplgvai sviiifycyr vnrqqklsst
201  wetgktrklm efsehcaiil eddrsdisst canninhnte llpieldtlv
251  gkgrfaevyk aklkqntseq fetvavkifp yeeyaswkte kdifsdinlk
301  henilqflta eerktelgkq ywlitafhak gnlqeyltrh viswedlrkl
351  gsslargiah lhsdhtpcgr pkmpivhrdl kssnilvknd ltcclcdfgl
401  slrldptlsv ddlansgqvg tarymapevl esrmnlenve sfkqtdvysm
451  alvlwemtsr cnavgevkdy eppfgskvre hpcvesmkdn vlrdrgrpei
501  psfwlnhqgi qmvcetltec wdhdpearlt aqcvaerfse lehldrlsgr
551  scseekiped gslnttk                (SEQ ID NO: 1)
```

FIGURE 1

```
  1  mgrgllrglw plhivlwtri astipphvqk sdvemeaqkd eiicpscnrt
 51  ahplrhinnd mivtdnngav kfpqlckfcd vrfstcdnqk scmsncsits
101  icekpqevcv avwrkndeni tletvchdpk lpyhdfiled aaspkcimke
151  kkkpgetffm cscssdecnd niifseeynt snpdlllvif qvtgisllpp
201  lgvaisviii fycyrvnrqq klsstwetgk trklmefseh caiileddrs
251  disstcanni nhntellpie ldtlvgkgrf aevykaklkq ntseqfetva
301  vkifpyeeya swtekdifs dinlkhenil qfltaeerkt elgkqywlit
351  afhakgnlqe yltrhviswe dlrklgssla rgiahlhsdh tpcgrpkmpi
401  vhrdlkssni lvkndltccl cdfglslrld ptlsvddlan sgqvgtarym
451  apevlesrmn lenvesfkqt dvysmalvlw emtsrcnavg evkdyeppfg
501  skvrehpcve smkdnvlrdr grpeipsfwl nhqgiqmvce tltecwdhdp
551  earltaqcva erfselehld rlsgrscsee kipedgslnt tk
     (SEQ ID NO: 2)
```

| | Fusion Protein | $k_a$ (1/Ms) | $k_d$ (1/s) | $K_D$ (pM) |
|---|---|---|---|---|
| TGFβ1 | hTβRII-hFc | $2.01 \times 10^6$ | $4.16 \times 10^{-4}$ | 207.0 |
| | hTβRII (G4S)2-hFc | $2.91 \times 10^6$ | $4.83 \times 10^{-4}$ | 165.8 |
| | hTβRII (G4S)3-hFc | $3.89 \times 10^6$ | $5.10 \times 10^{-4}$ | 92.4 |
| | hTβRII (G4S)4-hFc | $6.69 \times 10^6$ | $4.57 \times 10^{-4}$ | 68.4 |
| | hTβRII-extended hinge-hFc | $2.38 \times 10^6$ | $4.64 \times 10^{-4}$ | 195.5 |
| TGFβ3 | hTβRII-hFc | $1.99 \times 10^7$ | $1.57 \times 10^{-3}$ | 79.1 |
| | hTβRII (G4S)2-hFc | $1.74 \times 10^7$ | $1.81 \times 10^{-3}$ | 104.1 |
| | hTβRII (G4S)3-hFc | $2.09 \times 10^7$ | $8.32 \times 10^{-4}$ | 39.9 |
| | hTβRII (G4S)4-hFc | $8.80 \times 10^6$ | $2.76 \times 10^{-4}$ | 31.4 |
| | hTβRII-extended hinge-hFc | $1.51 \times 10^7$ | $1.39 \times 10^{-3}$ | 92.1 |

| Receptor | TGFβ1 | | |
|---|---|---|---|
| | $k_a$ (1/Ms) | $k_d$ (1/s) | $K_D$ (pM) |
| hTβRII (G4S)5-hFc | $7.36 \times 10^7$ | $6.48 \times 10^{-4}$ | 8.8 |
| hTβRII (G4S)6-hFc | $1.66 \times 10^8$ | $6.32 \times 10^{-4}$ | 3.8 |

| Receptor | TGFβ3 | | |
|---|---|---|---|
| | $k_a$ (1/Ms) | $k_d$ (1/s) | $K_D$ (pM) |
| hTβRII (G4S)5-hFc | $1.47 \times 10^8$ | $4.35 \times 10^{-4}$ | 2.96 |
| hTβRII (G4S)6-hFc | $5.99 \times 10^7$ | $2.75 \times 10^{-4}$ | 4.60 |

| | IC$_{50}$ (nM) | | |
|---|---|---|---|
| | TGFβ1 | TGFβ3 | Ratio TGFβ1/TGFβ3 |
| hTβRII-hFc | 7.69 | 0.18 | 42 |
| hTβRII(G4S)2-hFc | 1.12 | 0.13 | 8.61 |
| hTβRII(G4S)3-hFc | 0.22 | 0.17 | 1.29 |
| hTβRII(G4S)4-hFc | 0.07 | 0.03 | 2.3 |
| hTβRII extended hinge-hFc | 5.67 | 0.11 | 52 |

| Construct | TGFβ1—IC50 (nM) | TGFβ3—IC50 (nM) | Ratio TGFβ1/TGFβ3 |
|---|---|---|---|
| hTβRII (G4S)5-hFc | 0.03 | 0.04 | 0.75 |
| hTβRII (G4S)6-hFc | 0.02 | 0.04 | 0.5 |

Figure 5F

SEQUENCE LISTING

<160> NUMBER OF SEQ ID NOS: 66

<210> SEQ ID NO 1
<211> LENGTH: 567
<212> TYPE: PRT
<213> ORGANISM: Homo sapiens

<400> SEQUENCE: 1

Met Gly Arg Gly Leu Leu Arg Gly Leu Trp Pro Leu His Ile Val Leu
1               5                   10                  15

Trp Thr Arg Ile Ala Ser Thr Ile Pro Pro His Val Gln Lys Ser Val
            20                  25                  30

Asn Asn Asp Met Ile Val Thr Asp Asn Asn Gly Ala Val Lys Phe Pro
        35                  40                  45

Gln Leu Cys Lys Phe Cys Asp Val Arg Phe Ser Thr Cys Asp Asn Gln
    50                  55                  60

Lys Ser Cys Met Ser Asn Cys Ser Ile Thr Ser Ile Cys Glu Lys Pro
65                  70                  75                  80

Gln Glu Val Cys Val Ala Val Trp Arg Lys Asn Asp Glu Asn Ile Thr
                85                  90                  95

Leu Glu Thr Val Cys His Asp Pro Lys Leu Pro Tyr His Asp Phe Ile
            100                 105                 110

Leu Glu Asp Ala Ala Ser Pro Lys Cys Ile Met Lys Glu Lys Lys Lys
        115                 120                 125

Pro Gly Glu Thr Phe Phe Met Cys Ser Cys Ser Ser Asp Glu Cys Asn
    130                 135                 140

Asp Asn Ile Ile Phe Ser Glu Glu Tyr Asn Thr Ser Asn Pro Asp Leu
145                 150                 155                 160

Leu Leu Val Ile Phe Gln Val Thr Gly Ile Ser Leu Leu Pro Pro Leu
                165                 170                 175

Gly Val Ala Ile Ser Val Ile Ile Ile Phe Tyr Cys Tyr Arg Val Asn
            180                 185                 190

Arg Gln Gln Lys Leu Ser Ser Thr Trp Glu Thr Gly Lys Thr Arg Lys
        195                 200                 205

Leu Met Glu Phe Ser Glu His Cys Ala Ile Ile Leu Glu Asp Asp Arg
    210                 215                 220

Ser Asp Ile Ser Ser Thr Cys Ala Asn Asn Ile Asn His Asn Thr Glu
225                 230                 235                 240

Leu Leu Pro Ile Glu Leu Asp Thr Leu Val Gly Lys Gly Arg Phe Ala
                245                 250                 255

Glu Val Tyr Lys Ala Lys Leu Lys Gln Asn Thr Ser Glu Gln Phe Glu
            260                 265                 270

Thr Val Ala Val Lys Ile Phe Pro Tyr Glu Glu Tyr Ala Ser Trp Lys
        275                 280                 285

Thr Glu Lys Asp Ile Phe Ser Asp Ile Asn Leu Lys His Glu Asn Ile
    290                 295                 300

Leu Gln Phe Leu Thr Ala Glu Glu Arg Lys Thr Glu Leu Gly Lys Gln
305                 310                 315                 320

Tyr Trp Leu Ile Thr Ala Phe His Ala Lys Gly Asn Leu Gln Glu Tyr
                325                 330                 335

Leu Thr Arg His Val Ile Ser Trp Glu Asp Leu Arg Lys Leu Gly Ser
            340                 345                 350

Ser Leu Ala Arg Gly Ile Ala His Leu His Ser Asp His Thr Pro Cys
        355                 360                 365

Gly Arg Pro Lys Met Pro Ile Val His Arg Asp Leu Lys Ser Ser Asn
        370                 375                 380

Ile Leu Val Lys Asn Asp Leu Thr Cys Cys Leu Cys Asp Phe Gly Leu
385                 390                 395                 400

Ser Leu Arg Leu Asp Pro Thr Leu Ser Val Asp Asp Leu Ala Asn Ser
                405                 410                 415

Gly Gln Val Gly Thr Ala Arg Tyr Met Ala Pro Glu Val Leu Glu Ser
            420                 425                 430

Arg Met Asn Leu Glu Asn Val Glu Ser Phe Lys Gln Thr Asp Val Tyr
        435                 440                 445

Ser Met Ala Leu Val Leu Trp Glu Met Thr Ser Arg Cys Asn Ala Val
    450                 455                 460

Gly Glu Val Lys Asp Tyr Glu Pro Pro Phe Gly Ser Lys Val Arg Glu
465                 470                 475                 480

His Pro Cys Val Glu Ser Met Lys Asp Asn Val Leu Arg Asp Arg Gly
                485                 490                 495

Arg Pro Glu Ile Pro Ser Phe Trp Leu Asn His Gln Gly Ile Gln Met
            500                 505                 510

Val Cys Glu Thr Leu Thr Glu Cys Trp Asp His Asp Pro Glu Ala Arg
        515                 520                 525

Leu Thr Ala Gln Cys Val Ala Glu Arg Phe Ser Glu Leu Glu His Leu
    530                 535                 540

Asp Arg Leu Ser Gly Arg Ser Cys Ser Glu Glu Lys Ile Pro Glu Asp
545                 550                 555                 560

Gly Ser Leu Asn Thr Thr Lys
                565

<210> SEQ ID NO 2
<211> LENGTH: 592
<212> TYPE: PRT
<213> ORGANISM: Homo sapiens

<400> SEQUENCE: 2

Met Gly Arg Gly Leu Leu Arg Gly Leu Trp Pro Leu His Ile Val Leu
1               5                   10                  15

Trp Thr Arg Ile Ala Ser Thr Ile Pro Pro His Val Gln Lys Ser Asp
                20                  25                  30

Val Glu Met Glu Ala Gln Lys Asp Glu Ile Ile Cys Pro Ser Cys Asn
            35                  40                  45

Arg Thr Ala His Pro Leu Arg His Ile Asn Asn Asp Met Ile Val Thr
        50                  55                  60

Asp Asn Asn Gly Ala Val Lys Phe Pro Gln Leu Cys Lys Phe Cys Asp
65                  70                  75                  80

Val Arg Phe Ser Thr Cys Asp Asn Gln Lys Ser Cys Met Ser Asn Cys
                85                  90                  95

Ser Ile Thr Ser Ile Cys Glu Lys Pro Gln Glu Val Cys Val Ala Val
                100                 105                 110

Trp Arg Lys Asn Asp Glu Asn Ile Thr Leu Glu Thr Val Cys His Asp
            115                 120                 125

Pro Lys Leu Pro Tyr His Asp Phe Ile Leu Glu Asp Ala Ala Ser Pro
        130                 135                 140

Lys Cys Ile Met Lys Glu Lys Lys Pro Gly Glu Thr Phe Phe Met
145                 150                 155                 160

Cys Ser Cys Ser Ser Asp Glu Cys Asn Asp Asn Ile Ile Phe Ser Glu
                165                 170                 175

-continued

```
Glu Tyr Asn Thr Ser Asn Pro Asp Leu Leu Val Ile Phe Gln Val
                180                 185                 190
Thr Gly Ile Ser Leu Leu Pro Pro Leu Gly Val Ala Ile Ser Val Ile
            195                 200                 205
Ile Ile Phe Tyr Cys Tyr Arg Val Asn Arg Gln Gln Lys Leu Ser Ser
210                 215                 220
Thr Trp Glu Thr Gly Lys Thr Arg Lys Leu Met Glu Phe Ser Glu His
225                 230                 235                 240
Cys Ala Ile Ile Leu Glu Asp Asp Arg Ser Asp Ile Ser Ser Thr Cys
                245                 250                 255
Ala Asn Asn Ile Asn His Asn Thr Glu Leu Leu Pro Ile Glu Leu Asp
                260                 265                 270
Thr Leu Val Gly Lys Gly Arg Phe Ala Glu Val Tyr Lys Ala Lys Leu
                275                 280                 285
Lys Gln Asn Thr Ser Glu Gln Phe Glu Thr Val Ala Val Lys Ile Phe
290                 295                 300
Pro Tyr Glu Glu Tyr Ala Ser Trp Lys Thr Glu Lys Asp Ile Phe Ser
305                 310                 315                 320
Asp Ile Asn Leu Lys His Glu Asn Ile Leu Gln Phe Leu Thr Ala Glu
                325                 330                 335
Glu Arg Lys Thr Glu Leu Gly Lys Gln Tyr Trp Leu Ile Thr Ala Phe
                340                 345                 350
His Ala Lys Gly Asn Leu Gln Glu Tyr Leu Thr Arg His Val Ile Ser
                355                 360                 365
Trp Glu Asp Leu Arg Lys Leu Gly Ser Ser Leu Ala Arg Gly Ile Ala
                370                 375                 380
His Leu His Ser Asp His Thr Pro Cys Gly Arg Pro Lys Met Pro Ile
385                 390                 395                 400
Val His Arg Asp Leu Lys Ser Ser Asn Ile Leu Val Lys Asn Asp Leu
                405                 410                 415
Thr Cys Cys Leu Cys Asp Phe Gly Leu Ser Leu Arg Leu Asp Pro Thr
                420                 425                 430
Leu Ser Val Asp Asp Leu Ala Asn Ser Gly Gln Val Gly Thr Ala Arg
                435                 440                 445
Tyr Met Ala Pro Glu Val Leu Glu Ser Arg Met Asn Leu Glu Asn Val
450                 455                 460
Glu Ser Phe Lys Gln Thr Asp Val Tyr Ser Met Ala Leu Val Leu Trp
465                 470                 475                 480
Glu Met Thr Ser Arg Cys Asn Ala Val Gly Glu Val Lys Asp Tyr Glu
                485                 490                 495
Pro Pro Phe Gly Ser Lys Val Arg Glu His Pro Cys Val Glu Ser Met
                500                 505                 510
Lys Asp Asn Val Leu Arg Asp Arg Gly Arg Pro Glu Ile Pro Ser Phe
                515                 520                 525
Trp Leu Asn His Gln Gly Ile Gln Met Val Cys Glu Thr Leu Thr Glu
                530                 535                 540
Cys Trp Asp His Asp Pro Glu Ala Arg Leu Thr Ala Gln Cys Val Ala
545                 550                 555                 560
Glu Arg Phe Ser Glu Leu Glu His Leu Asp Arg Leu Ser Gly Arg Ser
                565                 570                 575
Cys Ser Glu Glu Lys Ile Pro Glu Asp Gly Ser Leu Asn Thr Thr Lys
                580                 585                 590
```

<210> SEQ ID NO 3
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Thr Gly Gly Gly
1

<210> SEQ ID NO 4
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Thr Gly Gly Gly Gly Ser Gly Gly Gly Gly Ser
1               5                   10

<210> SEQ ID NO 5
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Thr Gly Gly Gly Gly Ser Gly Gly Gly Gly Ser Gly Gly Gly Gly Ser
1               5                   10                  15

<210> SEQ ID NO 6
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Thr Gly Gly Gly Gly Ser Gly Gly Gly Gly Ser Gly Gly Gly Gly Ser
1               5                   10                  15

Gly Gly Gly Gly Ser
            20

<210> SEQ ID NO 7
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Thr Gly Gly Gly Pro Lys Ser Cys Asp Lys
1               5                   10

<210> SEQ ID NO 8
<211> LENGTH: 1248
<212> TYPE: DNA
<213> ORGANISM: Artificial Sequence
<220> FEATURE:

<223> OTHER INFORMATION: Description of Artificial Sequence: Synthetic
polynucleotide

<400> SEQUENCE: 8

```
atggatgcaa tgaagagagg gctctgctgt gtgctgctgc tgtgtggagc agtcttcgtt    60
tcgcccggcg ccacgatccc accgcacgtt cagaagtcgg atgtggaaat ggaggcccag   120
aaagatgaaa tcatctgccc cagctgtaat aggactgccc atccactgag acatattaat   180
aacgacatga tagtcactga caacaacggt gcagtcaagt tccacaact gtgtaaattt    240
tgtgatgtga gattttccac ctgtgacaac cagaaatcct gcatgagcaa ctgcagcatc   300
acctccatct gtgagaagcc acaggaagtc tgtgtggctg tatggagaaa gaatgacgag   360
aacataacac tagagacagt ttgccatgac cccaagctcc cctaccatga ctttattctg   420
gaagatgctg cttctccaaa gtgcattatg aaggaaaaaa aaaagcctgg tgagactttc   480
ttcatgtgtt cctgtagctc tgatgagtgc aatgacaaca tcatcttctc agaagaatat   540
aacaccagca atcctgacac cggtggtgga actcacacat gcccaccgtg cccagcacct   600
gaactcctgg ggggaccgtc agtcttcctc ttccccccaa acccaagga caccctcatg    660
atctcccgga cccctgaggt cacatgcgtg gtggtggacg tgagccacga agaccctgag   720
gtcaagttca actggtacgt ggacggcgtg gaggtgcata atgccaagac aaagccgcgg   780
gaggagcagt acaacagcac gtaccgtgtg gtcagcgtcc tcaccgtcct gcaccaggac   840
tggctgaatg gcaaggagta caagtgcaag gtctccaaca aagccctccc agcccccatc   900
gagaaaacca tctccaaagc caagggcag ccccgagaac cacaggtgta caccctgccc    960
ccatcccggg aggagatgac caagaaccag gtcagcctga cctgcctggt caaaggcttc  1020
tatcccagcg acatcgccgt ggagtgggag agcaatgggc agccggagaa caactacaag  1080
accacgcctc ccgtgctgga ctccgacggc tccttcttcc tctatagcaa gctcaccgtg  1140
gacaagagca ggtggcagca ggggaacgtc ttctcatgct ccgtgatgca tgaggctctg  1200
cacaaccact acacgcagaa gagcctctcc ctgtctccgg gtaaatga              1248
```

<210> SEQ ID NO 9
<211> LENGTH: 415
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 9

```
Met Asp Ala Met Lys Arg Gly Leu Cys Cys Val Leu Leu Leu Cys Gly
1               5                   10                  15
Ala Val Phe Val Ser Pro Gly Ala Thr Ile Pro Pro His Val Gln Lys
            20                  25                  30
Ser Asp Val Glu Met Glu Ala Gln Lys Asp Glu Ile Ile Cys Pro Ser
        35                  40                  45
Cys Asn Arg Thr Ala His Pro Leu Arg His Ile Asn Asn Asp Met Ile
    50                  55                  60
Val Thr Asp Asn Asn Gly Ala Val Lys Phe Pro Gln Leu Cys Lys Phe
65                  70                  75                  80
Cys Asp Val Arg Phe Ser Thr Cys Asp Asn Gln Lys Ser Cys Met Ser
                85                  90                  95
Asn Cys Ser Ile Thr Ser Ile Cys Glu Lys Pro Gln Glu Val Cys Val
            100                 105                 110
```

Ala Val Trp Arg Lys Asn Asp Glu Asn Ile Thr Leu Glu Thr Val Cys
            115                 120                 125

His Asp Pro Lys Leu Pro Tyr His Asp Phe Ile Leu Glu Asp Ala Ala
        130                 135                 140

Ser Pro Lys Cys Ile Met Lys Glu Lys Lys Pro Gly Glu Thr Phe
145                 150                 155                 160

Phe Met Cys Ser Cys Ser Ser Asp Glu Cys Asn Asp Asn Ile Ile Phe
                165                 170                 175

Ser Glu Glu Tyr Asn Thr Ser Asn Pro Asp Thr Gly Gly Gly Thr His
                180                 185                 190

Thr Cys Pro Pro Cys Pro Ala Pro Glu Leu Leu Gly Gly Pro Ser Val
            195                 200                 205

Phe Leu Phe Pro Pro Lys Pro Lys Asp Thr Leu Met Ile Ser Arg Thr
        210                 215                 220

Pro Glu Val Thr Cys Val Val Val Asp Val Ser His Glu Asp Pro Glu
225                 230                 235                 240

Val Lys Phe Asn Trp Tyr Val Asp Gly Val Glu Val His Asn Ala Lys
                245                 250                 255

Thr Lys Pro Arg Glu Glu Gln Tyr Asn Ser Thr Tyr Arg Val Val Ser
            260                 265                 270

Val Leu Thr Val Leu His Gln Asp Trp Leu Asn Gly Lys Glu Tyr Lys
        275                 280                 285

Cys Lys Val Ser Asn Lys Ala Leu Pro Ala Pro Ile Glu Lys Thr Ile
    290                 295                 300

Ser Lys Ala Lys Gly Gln Pro Arg Glu Pro Gln Val Tyr Thr Leu Pro
305                 310                 315                 320

Pro Ser Arg Glu Glu Met Thr Lys Asn Gln Val Ser Leu Thr Cys Leu
                325                 330                 335

Val Lys Gly Phe Tyr Pro Ser Asp Ile Ala Val Glu Trp Glu Ser Asn
            340                 345                 350

Gly Gln Pro Glu Asn Asn Tyr Lys Thr Thr Pro Pro Val Leu Asp Ser
        355                 360                 365

Asp Gly Ser Phe Phe Leu Tyr Ser Lys Leu Thr Val Asp Lys Ser Arg
    370                 375                 380

Trp Gln Gln Gly Asn Val Phe Ser Cys Ser Val Met His Glu Ala Leu
385                 390                 395                 400

His Asn His Tyr Thr Gln Lys Ser Leu Ser Leu Ser Pro Gly Lys
                405                 410                 415

<210> SEQ ID NO 10
<211> LENGTH: 1284
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 10
atggatgcaa tgaagagagg gctctgctgt gtgctgctgc tgtgtggagc agtcttcgtt      60
tcgcccggcg ccacgatccc accgcacgtt cagaagtcgg atgtggaaat ggaggcccag     120
aaagatgaaa tcatctgccc cagctgtaat aggactgccc atccactgag acatattaat     180
aacgacatga tagtcactga caacaacggt gcagtcaagt ttccacaact gtgtaaattt     240
tgtgatgtga gattttccac ctgtgacaac cagaaatcct gcatgagcaa ctgcagcatc     300
acctccatct gtgagaagcc acaggaagtc tgtgtggctg tatggagaaa gaatgacgag     360

```
aacataacac tagagacagt ttgccatgac cccaagctcc cctaccatga ctttattctg    420
gaagatgctg cttctccaaa gtgcattatg aaggaaaaaa aaaagcctgg tgagactttc    480
ttcatgtgtt cctgtagctc tgatgagtgc aatgacaaca tcatcttctc agaagaatat    540
aacaccagca atcctgacac cggtggtgga ggaagtggtg gaggtggttc tggaggtggt    600
ggaagtactc acacatgccc accgtgccca gcacctgaac tcctgggggg accgtcagtc    660
ttcctcttcc cccaaaaacc caaggacacc ctcatgatct cccggacccc tgaggtcaca    720
tgcgtggtgg tggacgtgag ccacgaagac cctgaggtca agttcaactg gtacgtggac    780
ggcgtggagg tgcataatgc caagacaaag ccgcgggagg agcagtacaa cagcacgtac    840
cgtgtggtca gcgtcctcac cgtcctgcac caggactggc tgaatggcaa ggagtacaag    900
tgcaaggtct ccaacaaagc cctcccagcc ccatcgaga  aaaccatctc caaagccaaa    960
gggcagcccc gagaaccaca ggtgtacacc ctgcccccat cccgggagga gatgaccaag   1020
aaccaggtca gcctgacctg cctggtcaaa ggcttctatc ccagcgacat cgccgtggag   1080
tgggagagca atgggcagcc ggagaacaac tacaagacca cgcctcccgt gctggactcc   1140
gacggctcct tcttcctcta tagcaagctc accgtggaca agagcaggtg gcagcagggg   1200
aacgtcttct catgctccgt gatgcatgag gctctgcaca accactacac gcagaagagc   1260
ctctccctgt ctccgggtaa atga                                          1284

<210> SEQ ID NO 11
<211> LENGTH: 427
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Met Asp Ala Met Lys Arg Gly Leu Cys Cys Val Leu Leu Cys Gly
1               5                   10                  15

Ala Val Phe Val Ser Pro Gly Ala Thr Ile Pro Pro His Val Gln Lys
                20                  25                  30

Ser Asp Val Glu Met Glu Ala Gln Lys Asp Glu Ile Ile Cys Pro Ser
            35                  40                  45

Cys Asn Arg Thr Ala His Pro Leu Arg His Ile Asn Asn Asp Met Ile
        50                  55                  60

Val Thr Asp Asn Asn Gly Ala Val Lys Phe Pro Gln Leu Cys Lys Phe
65                  70                  75                  80

Cys Asp Val Arg Phe Ser Thr Cys Asp Asn Gln Lys Ser Cys Met Ser
                85                  90                  95

Asn Cys Ser Ile Thr Ser Ile Cys Glu Lys Pro Gln Glu Val Cys Val
            100                 105                 110

Ala Val Trp Arg Lys Asn Asp Glu Asn Ile Thr Leu Glu Thr Val Cys
        115                 120                 125

His Asp Pro Lys Leu Pro Tyr His Asp Phe Ile Leu Glu Asp Ala Ala
    130                 135                 140

Ser Pro Lys Cys Ile Met Lys Glu Lys Lys Pro Gly Glu Thr Phe
145                 150                 155                 160

Phe Met Cys Ser Cys Ser Ser Asp Glu Cys Asn Asp Asn Ile Ile Phe
                165                 170                 175

Ser Glu Glu Tyr Asn Thr Ser Asn Pro Asp Thr Gly Gly Gly Gly Ser
            180                 185                 190
```

```
Gly Gly Gly Gly Ser Gly Gly Gly Ser Thr His Thr Cys Pro Pro
        195                 200                 205

Cys Pro Ala Pro Glu Leu Leu Gly Gly Pro Ser Val Phe Leu Phe Pro
        210                 215                 220

Pro Lys Pro Lys Asp Thr Leu Met Ile Ser Arg Thr Pro Glu Val Thr
225                 230                 235                 240

Cys Val Val Val Asp Val Ser His Glu Asp Pro Glu Val Lys Phe Asn
                245                 250                 255

Trp Tyr Val Asp Gly Val Glu Val His Asn Ala Lys Thr Lys Pro Arg
                260                 265                 270

Glu Glu Gln Tyr Asn Ser Thr Tyr Arg Val Val Ser Val Leu Thr Val
            275                 280                 285

Leu His Gln Asp Trp Leu Asn Gly Lys Glu Tyr Lys Cys Lys Val Ser
        290                 295                 300

Asn Lys Ala Leu Pro Ala Pro Ile Glu Lys Thr Ile Ser Lys Ala Lys
305                 310                 315                 320

Gly Gln Pro Arg Glu Pro Gln Val Tyr Thr Leu Pro Pro Ser Arg Glu
                325                 330                 335

Glu Met Thr Lys Asn Gln Val Ser Leu Thr Cys Leu Val Lys Gly Phe
            340                 345                 350

Tyr Pro Ser Asp Ile Ala Val Glu Trp Glu Ser Asn Gly Gln Pro Glu
        355                 360                 365

Asn Asn Tyr Lys Thr Thr Pro Pro Val Leu Asp Ser Asp Gly Ser Phe
370                 375                 380

Phe Leu Tyr Ser Lys Leu Thr Val Asp Lys Ser Arg Trp Gln Gln Gly
385                 390                 395                 400

Asn Val Phe Ser Cys Ser Val Met His Glu Ala Leu His Asn His Tyr
                405                 410                 415

Thr Gln Lys Ser Leu Ser Leu Ser Pro Gly Lys
            420                 425

<210> SEQ ID NO 12
<211> LENGTH: 1299
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 12
atggatgcaa tgaagagagg gctctgctgt gtgctgctgc tgtgtggagc agtcttcgtt       60
tcgcccggcg ccacgatccc accgcacgtt cagaagtcgg atgtggaaat ggaggcccag     120
aaagatgaaa tcatctgccc cagctgtaat aggactgccc atccactgag acatattaat     180
aacgacatga tagtcactga acaacggttg cagtcaagt ttccacaact gtgtaaattt     240
tgtgatgtga gatttccac ctgtgacaac cagaaatcct gcatgagcaa ctgcagcatc     300
acctccatct gtgagaagcc acaggaagtc tgtgtggctg tatggagaaa gaatgacgag     360
aacataacac tagagacagt ttgccatgac cccaagctcc cctaccatga ctttattctg     420
gaagatgctg cttctccaaa gtgcattatg aaggaaaaaa aaaagcctgg tgagactttc     480
ttcatgtgtt cctgtagctc tgatgagtgc aatgacaaca tcatcttctc agaagaatat     540
aacaccagca atcctgacac cggtggtgga ggttctggag gtggaggaag tggtggaggt     600
ggttctggag gtggtggaag tactcacaca tgcccaccgt gcccagcacc tgaactcctg     660
```

```
ggggaccgt cagtcttcct cttccccca aacccaagg acaccctcat gatctcccgg      720
acccctgagg tcacatgcgt ggtggtggac gtgagccacg aagaccctga ggtcaagttc      780
aactggtacg tggacggcgt ggaggtgcat aatgccaaga caaagccgcg ggaggagcag      840
tacaacagca cgtaccgtgt ggtcagcgtc ctcaccgtcc tgcaccagga ctggctgaat      900
ggcaaggagt acaagtgcaa ggtctccaac aaagccctcc cagcccccat cgagaaaacc      960
atctccaaag ccaaagggca gccccgagaa ccacaggtgt acaccctgcc cccatcccgg     1020
gaggagatga ccaagaacca ggtcagcctg acctgcctgg tcaaaggctt ctatcccagc     1080
gacatcgccg tggagtggga gagcaatggg cagccggaga acaactacaa gaccacgcct     1140
cccgtgctgg actccgacgg ctccttcttc ctctatagca agctcaccgt ggacaagagc     1200
aggtggcagc aggggaacgt cttctcatgc tccgtgatgc atgaggctct gcacaaccac     1260
tacacgcaga agagcctctc cctgtctccg ggtaaatga                           1299
```

<210> SEQ ID NO 13
<211> LENGTH: 432
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

```
Met Asp Ala Met Lys Arg Gly Leu Cys Cys Val Leu Leu Leu Cys Gly
1               5                   10                  15

Ala Val Phe Val Ser Pro Gly Ala Thr Ile Pro Pro His Val Gln Lys
            20                  25                  30

Ser Asp Val Glu Met Glu Ala Gln Lys Asp Glu Ile Ile Cys Pro Ser
        35                  40                  45

Cys Asn Arg Thr Ala His Pro Leu Arg His Ile Asn Asn Asp Met Ile
    50                  55                  60

Val Thr Asp Asn Asn Gly Ala Val Lys Phe Pro Gln Leu Cys Lys Phe
65                  70                  75                  80

Cys Asp Val Arg Phe Ser Thr Cys Asp Asn Gln Lys Ser Cys Met Ser
                85                  90                  95

Asn Cys Ser Ile Thr Ser Ile Cys Glu Lys Pro Gln Glu Val Cys Val
            100                 105                 110

Ala Val Trp Arg Lys Asn Asp Glu Asn Ile Thr Leu Glu Thr Val Cys
        115                 120                 125

His Asp Pro Lys Leu Pro Tyr His Asp Phe Ile Leu Glu Asp Ala Ala
    130                 135                 140

Ser Pro Lys Cys Ile Met Lys Glu Lys Lys Pro Gly Glu Thr Phe Phe
145                 150                 155                 160

Phe Met Cys Ser Cys Ser Ser Asp Glu Cys Asn Asp Asn Ile Ile Phe
                165                 170                 175

Ser Glu Glu Tyr Asn Thr Ser Asn Pro Asp Thr Gly Gly Gly Gly Ser
            180                 185                 190

Gly Gly Gly Gly Ser Gly Gly Gly Ser Gly Gly Gly Gly Ser Thr
        195                 200                 205

His Thr Cys Pro Pro Cys Pro Ala Pro Glu Leu Leu Gly Gly Pro Ser
    210                 215                 220

Val Phe Leu Phe Pro Pro Lys Pro Lys Asp Thr Leu Met Ile Ser Arg
225                 230                 235                 240

Thr Pro Glu Val Thr Cys Val Val Val Asp Val Ser His Glu Asp Pro
```

```
            245                 250                 255
Glu Val Lys Phe Asn Trp Tyr Val Asp Gly Val Glu Val His Asn Ala
            260                 265                 270

Lys Thr Lys Pro Arg Glu Glu Gln Tyr Asn Ser Thr Tyr Arg Val Val
        275                 280                 285

Ser Val Leu Thr Val Leu His Gln Asp Trp Leu Asn Gly Lys Glu Tyr
    290                 295                 300

Lys Cys Lys Val Ser Asn Lys Ala Leu Pro Ala Pro Ile Glu Lys Thr
305                 310                 315                 320

Ile Ser Lys Ala Lys Gly Gln Pro Arg Glu Pro Gln Val Tyr Thr Leu
                325                 330                 335

Pro Pro Ser Arg Glu Glu Met Thr Lys Asn Gln Val Ser Leu Thr Cys
            340                 345                 350

Leu Val Lys Gly Phe Tyr Pro Ser Asp Ile Ala Val Glu Trp Glu Ser
        355                 360                 365

Asn Gly Gln Pro Glu Asn Asn Tyr Lys Thr Thr Pro Pro Val Leu Asp
    370                 375                 380

Ser Asp Gly Ser Phe Phe Leu Tyr Ser Lys Leu Thr Val Asp Lys Ser
385                 390                 395                 400

Arg Trp Gln Gln Gly Asn Val Phe Ser Cys Ser Val Met His Glu Ala
                405                 410                 415

Leu His Asn His Tyr Thr Gln Lys Ser Leu Ser Leu Ser Pro Gly Lys
            420                 425                 430

<210> SEQ ID NO 14
<211> LENGTH: 1269
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 14
atggatgcaa tgaagagagg ctctgctgtg tgctgctgc tgtgtggagc agtcttcgtt      60
tcgcccggcg ccacgatccc accgcacgtt cagaagtcgg atgtggaaat ggaggcccag    120
aaagatgaaa tcatctgccc cagctgtaat aggactgccc atccactgag acatattaat    180
aacgacatga tagtcactga caacaacggt gcagtcaagt ttccacaact gtgtaaattt    240
tgtgatgtga gattttccac ctgtgacaac cagaaatcct gcatgagcaa ctgcagcatc    300
acctccatct gtgagaagcc acaggaagtc tgtgtggctg tatggagaaa gaatgacgag    360
aacataacac tagagacagt ttgccatgac cccaagctcc cctaccatga ctttattctg    420
gaagatgctg cttctccaaa gtgcattatg aaggaaaaaa aaaagcctgg tgagactttc    480
ttcatgtgtt cctgtagctc tgatgagtgc aatgacaaca tcatcttctc agaagaatat    540
aacaccagca atcctgacac cggtggaggt ggttctggag gtggtggaag tactcacaca    600
tgcccaccgt gcccagcacc tgaactcctg ggggaccgt cagtcttcct cttccccca     660 aaacccaagg acaccctcat gatctcccgg acccctgagg tcacatgcgt ggtggtggac    720
gtgagccacg aagaccctga ggtcaagttc aactggtacg tggacggcgt ggaggtgcat    780
aatgccaaga caaagccgcg ggaggagcag tacaacagca cgtaccgtgt ggtcagcgtc    840
ctcaccgtcc tgcaccagga ctggctgaat ggcaaggagt acaagtgcaa ggtctccaac    900
aaagccctcc cagcccccat cgagaaaacc atctccaaag ccaaggca gccccgagaa      960 ccacaggtgt acaccctgcc cccatcccgg gaggagatga ccaagaacca ggtcagcctg   1020
```

```
acctgcctgg tcaaaggctt ctatcccagc gacatcgccg tggagtggga gagcaatggg    1080
cagccggaga caactacaa gaccacgcct cccgtgctgg actccgacgg ctccttcttc    1140
ctctatagca agctcaccgt ggacaagagc aggtggcagc aggggaacgt cttctcatgc    1200
tccgtgatgc atgaggctct gcacaaccac tacacgcaga gagcctctc cctgtctccg    1260 ggtaaatga                                                            1269
```

<210> SEQ ID NO 15
<211> LENGTH: 422
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 15

```
Met Asp Ala Met Lys Arg Gly Leu Cys Cys Val Leu Leu Cys Gly
1               5                   10                  15

Ala Val Phe Val Ser Pro Gly Ala Thr Ile Pro His Val Gln Lys
                20                  25                  30

Ser Asp Val Glu Met Glu Ala Gln Lys Asp Glu Ile Ile Cys Pro Ser
            35                  40                  45

Cys Asn Arg Thr Ala His Pro Leu Arg His Ile Asn Asn Asp Met Ile
    50                  55                  60

Val Thr Asp Asn Asn Gly Ala Val Lys Phe Pro Gln Leu Cys Lys Phe
65                  70                  75                  80

Cys Asp Val Arg Phe Ser Thr Cys Asp Asn Gln Lys Ser Cys Met Ser
                85                  90                  95

Asn Cys Ser Ile Thr Ser Ile Cys Glu Lys Pro Gln Glu Val Cys Val
            100                 105                 110

Ala Val Trp Arg Lys Asn Asp Glu Asn Ile Thr Leu Glu Thr Val Cys
        115                 120                 125

His Asp Pro Lys Leu Pro Tyr His Asp Phe Ile Leu Glu Asp Ala Ala
    130                 135                 140

Ser Pro Lys Cys Ile Met Lys Glu Lys Lys Pro Gly Glu Thr Phe
145                 150                 155                 160

Phe Met Cys Ser Cys Ser Ser Asp Glu Cys Asn Asp Asn Ile Ile Phe
                165                 170                 175

Ser Glu Glu Tyr Asn Thr Ser Asn Pro Asp Thr Gly Gly Gly Ser
            180                 185                 190

Gly Gly Gly Gly Ser Thr His Thr Cys Pro Pro Cys Pro Ala Pro Glu
        195                 200                 205

Leu Leu Gly Gly Pro Ser Val Phe Leu Phe Pro Pro Lys Pro Lys Asp
    210                 215                 220

Thr Leu Met Ile Ser Arg Thr Pro Glu Val Thr Cys Val Val Asp
225                 230                 235                 240

Val Ser His Glu Asp Pro Glu Val Lys Phe Asn Trp Tyr Val Asp Gly
                245                 250                 255

Val Glu Val His Asn Ala Lys Thr Lys Pro Arg Glu Glu Gln Tyr Asn
            260                 265                 270

Ser Thr Tyr Arg Val Val Ser Val Leu Thr Val Leu His Gln Asp Trp
        275                 280                 285

Leu Asn Gly Lys Glu Tyr Lys Cys Lys Val Ser Asn Lys Ala Leu Pro
    290                 295                 300
```

Ala Pro Ile Glu Lys Thr Ile Ser Lys Ala Lys Gly Gln Pro Arg Glu
305                 310                 315                 320

Pro Gln Val Tyr Thr Leu Pro Pro Ser Arg Glu Glu Met Thr Lys Asn
            325                 330                 335

Gln Val Ser Leu Thr Cys Leu Val Lys Gly Phe Tyr Pro Ser Asp Ile
            340                 345                 350

Ala Val Glu Trp Glu Ser Asn Gly Gln Pro Glu Asn Asn Tyr Lys Thr
            355                 360                 365

Thr Pro Pro Val Leu Asp Ser Asp Gly Ser Phe Phe Leu Tyr Ser Lys
    370                 375                 380

Leu Thr Val Asp Lys Ser Arg Trp Gln Gln Gly Asn Val Phe Ser Cys
385                 390                 395                 400

Ser Val Met His Glu Ala Leu His Asn His Tyr Thr Gln Lys Ser Leu
            405                 410                 415

Ser Leu Ser Pro Gly Lys
            420

<210> SEQ ID NO 16
<211> LENGTH: 1266
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 16
atggatgcaa tgaagagagg gctctgctgt gtgctgctgc tgtgtggagc agtcttcgtt      60
tcgcccggcg ccacgatccc accgcacgtt cagaagtcgg atgtggaaat ggaggcccag     120
aaagatgaaa tcatctgccc cagctgtaat aggactgccc atccactgag acatattaat     180
aacgacatga tagtcactga caacaacggt gcagtcaagt tccacaact gtgtaaattt     240 tgtgatgtga gattttccac ctgtgacaac cagaaatcct gcatgagcaa ctgcagcatc     300
acctccatct gtgagaagcc acaggaagtc tgtgtggctg tatggagaaa gaatgacgag     360
aacataacac tagagacagt ttgccatgac cccaagctcc cctaccatga ctttattctg     420
gaagatgctg cttctccaaa gtgcattatg aaggaaaaaa aaaagcctgg tgagactttc     480
ttcatgtgtt cctgtagctc tgatgagtgc aatgacaaca tcatcttctc agaagaatat     540
aacaccagca atcctgacac cggtggtgga cccaaatctt gtgacaaaac tcacacatgc     600
ccaccgtgcc cagcacctga actcctgggg ggaccgtcag tcttcctctt ccccccaaaa     660
cccaaggaca ccctcatgat ctcccggacc cctgaggtca catgcgtggt ggtggacgtg     720
agccacgaag accctgaggt caagttcaac tggtacgtgg acggcgtgga ggtgcataat     780
gccaagacaa agccgcggga ggagcagtac aacagcacgt accgtgtggt cagcgtcctc     840
accgtcctgc accaggactg gctgaatggc aaggagtaca agtgcaaggt ctccaacaaa     900
gccctcccag cccccatcga gaaaaccatc tccaaagcca agggcagccc cgagaaccca     960
caggtgtaca ccctgccccc atcccgggag gagatgacca agaaccaggt cagcctgacc    1020
tgcctggtca aaggcttcta tcccagcgac atcgccgtgg agtgggagag caatgggcag    1080
ccggagaaca actacaagac cacgcctccc gtgctggact ccgacggctc cttcttcctc    1140
tatagcaagc tcaccgtgga caagagcagg tggcagcagg ggaacgtctt ctcatgctcc    1200
gtgatgcatg aggctctgca caaccactac acgcagaaga gcctctccct gtccccgggt    1260
aaatga                                                              1266

<210> SEQ ID NO 17
<211> LENGTH: 421
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 17

```
Met Asp Ala Met Lys Arg Gly Leu Cys Cys Val Leu Leu Leu Cys Gly
1               5                   10                  15

Ala Val Phe Val Ser Pro Gly Ala Thr Ile Pro Pro His Val Gln Lys
            20                  25                  30

Ser Asp Val Glu Met Glu Ala Gln Lys Asp Glu Ile Ile Cys Pro Ser
        35                  40                  45

Cys Asn Arg Thr Ala His Pro Leu Arg His Ile Asn Asn Asp Met Ile
    50                  55                  60

Val Thr Asp Asn Asn Gly Ala Val Lys Phe Pro Gln Leu Cys Lys Phe
65                  70                  75                  80

Cys Asp Val Arg Phe Ser Thr Cys Asp Asn Gln Lys Ser Cys Met Ser
                85                  90                  95

Asn Cys Ser Ile Thr Ser Ile Cys Glu Lys Pro Gln Glu Val Cys Val
            100                 105                 110

Ala Val Trp Arg Lys Asn Asp Glu Asn Ile Thr Leu Glu Thr Val Cys
        115                 120                 125

His Asp Pro Lys Leu Pro Tyr His Asp Phe Ile Leu Glu Asp Ala Ala
    130                 135                 140

Ser Pro Lys Cys Ile Met Lys Glu Lys Lys Lys Pro Gly Glu Thr Phe
145                 150                 155                 160

Phe Met Cys Ser Cys Ser Ser Asp Glu Cys Asn Asp Asn Ile Ile Phe
                165                 170                 175

Ser Glu Glu Tyr Asn Thr Ser Asn Pro Asp Thr Gly Gly Gly Pro Lys
            180                 185                 190

Ser Cys Asp Lys Thr His Thr Cys Pro Pro Cys Pro Ala Pro Glu Leu
        195                 200                 205

Leu Gly Gly Pro Ser Val Phe Leu Phe Pro Pro Lys Pro Lys Asp Thr
    210                 215                 220

Leu Met Ile Ser Arg Thr Pro Glu Val Thr Cys Val Val Val Asp Val
225                 230                 235                 240

Ser His Glu Asp Pro Glu Val Lys Phe Asn Trp Tyr Val Asp Gly Val
                245                 250                 255

Glu Val His Asn Ala Lys Thr Lys Pro Arg Glu Glu Gln Tyr Asn Ser
            260                 265                 270

Thr Tyr Arg Val Val Ser Val Leu Thr Val Leu His Gln Asp Trp Leu
        275                 280                 285

Asn Gly Lys Glu Tyr Lys Cys Lys Val Ser Asn Lys Ala Leu Pro Ala
    290                 295                 300

Pro Ile Glu Lys Thr Ile Ser Lys Ala Lys Gly Gln Pro Arg Glu Pro
305                 310                 315                 320

Gln Val Tyr Thr Leu Pro Pro Ser Arg Glu Glu Met Thr Lys Asn Gln
                325                 330                 335

Val Ser Leu Thr Cys Leu Val Lys Gly Phe Tyr Pro Ser Asp Ile Ala
            340                 345                 350

Val Glu Trp Glu Ser Asn Gly Gln Pro Glu Asn Asn Tyr Lys Thr Thr
        355                 360                 365
```

Pro Pro Val Leu Asp Ser Asp Gly Ser Phe Phe Leu Tyr Ser Lys Leu
            370                 375                 380

Thr Val Asp Lys Ser Arg Trp Gln Gln Gly Asn Val Phe Ser Cys Ser
385                 390                 395                 400

Val Met His Glu Ala Leu His Asn His Tyr Thr Gln Lys Ser Leu Ser
                405                 410                 415

Leu Ser Pro Gly Lys
            420

<210> SEQ ID NO 18
<211> LENGTH: 162
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Thr Ile Pro Pro His Val Gln Lys Ser Asp Val Glu Met Glu Ala Gln
1               5                   10                  15

Lys Asp Glu Ile Ile Cys Pro Ser Cys Asn Arg Thr Ala His Pro Leu
            20                  25                  30

Arg His Ile Asn Asn Asp Met Ile Val Thr Asp Asn Asn Gly Ala Val
        35                  40                  45

Lys Phe Pro Gln Leu Cys Lys Phe Cys Asp Val Arg Phe Ser Thr Cys
    50                  55                  60

Asp Asn Gln Lys Ser Cys Met Ser Asn Cys Ser Ile Thr Ser Ile Cys
65                  70                  75                  80

Glu Lys Pro Gln Glu Val Cys Val Ala Val Trp Arg Lys Asn Asp Glu
                85                  90                  95

Asn Ile Thr Leu Glu Thr Val Cys His Asp Pro Lys Leu Pro Tyr His
            100                 105                 110

Asp Phe Ile Leu Glu Asp Ala Ala Ser Pro Lys Cys Ile Met Lys Glu
        115                 120                 125

Lys Lys Lys Pro Gly Glu Thr Phe Phe Met Cys Ser Cys Ser Ser Asp
    130                 135                 140

Glu Cys Asn Asp Asn Ile Ile Phe Ser Glu Glu Tyr Asn Thr Ser Asn
145                 150                 155                 160

Pro Asp

<210> SEQ ID NO 19
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Gly Gly Gly Gly Ser
1               5

<210> SEQ ID NO 20
<211> LENGTH: 225
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Thr His Thr Cys Pro Pro Cys Pro Ala Pro Glu Leu Leu Gly Gly Pro
1               5                   10                  15
Ser Val Phe Leu Phe Pro Pro Lys Pro Lys Asp Thr Leu Met Ile Ser
            20                  25                  30
Arg Thr Pro Glu Val Thr Cys Val Val Val Asp Val Ser His Glu Asp
        35                  40                  45
Pro Glu Val Lys Phe Asn Trp Tyr Val Asp Gly Val Glu Val His Asn
    50                  55                  60
Ala Lys Thr Lys Pro Arg Glu Glu Gln Tyr Asn Ser Thr Tyr Arg Val
65                  70                  75                  80
Val Ser Val Leu Thr Val Leu His Gln Asp Trp Leu Asn Gly Lys Glu
                85                  90                  95
Tyr Lys Cys Lys Val Ser Asn Lys Ala Leu Pro Ala Pro Ile Glu Lys
            100                 105                 110
Thr Ile Ser Lys Ala Lys Gly Gln Pro Arg Glu Pro Gln Val Tyr Thr
        115                 120                 125
Leu Pro Pro Ser Arg Glu Glu Met Thr Lys Asn Gln Val Ser Leu Thr
    130                 135                 140
Cys Leu Val Lys Gly Phe Tyr Pro Ser Asp Ile Ala Val Glu Trp Glu
145                 150                 155                 160
Ser Asn Gly Gln Pro Glu Asn Asn Tyr Lys Thr Thr Pro Pro Val Leu
                165                 170                 175
Asp Ser Asp Gly Ser Phe Phe Leu Tyr Ser Lys Leu Thr Val Asp Lys
            180                 185                 190
Ser Arg Trp Gln Gln Gly Asn Val Phe Ser Cys Ser Val Met His Glu
        195                 200                 205
Ala Leu His Asn His Tyr Thr Gln Lys Ser Leu Ser Leu Ser Pro Gly
    210                 215                 220
Lys
225

<210> SEQ ID NO 21
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Gly Gly Gly Gly Ser Gly Gly Gly Gly Ser
1               5                   10

<210> SEQ ID NO 22
<211> LENGTH: 22
<212> TYPE: PRT
<213> ORGANISM: Unknown
<220> FEATURE:
<223> OTHER INFORMATION: Description of Unknown:
      Native sequence

<400> SEQUENCE: 22

Met Gly Arg Gly Leu Leu Arg Gly Leu Trp Pro Leu His Ile Val Leu
1               5                   10                  15
Trp Thr Arg Ile Ala Ser
            20

```
<210> SEQ ID NO 23
<211> LENGTH: 22
<212> TYPE: PRT
<213> ORGANISM: Unknown
<220> FEATURE:
<223> OTHER INFORMATION: Description of Unknown:
      Tissue plasminogen activator sequence

<400> SEQUENCE: 23

Met Asp Ala Met Lys Arg Gly Leu Cys Cys Val Leu Leu Leu Cys Gly
1               5                   10                  15

Ala Val Phe Val Ser Pro
            20

<210> SEQ ID NO 24
<211> LENGTH: 21
<212> TYPE: PRT
<213> ORGANISM: Apis sp.

<400> SEQUENCE: 24

Met Lys Phe Leu Val Asn Val Ala Leu Val Phe Met Val Val Tyr Ile
1               5                   10                  15

Ser Tyr Ile Tyr Ala
            20

<210> SEQ ID NO 25
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Thr Gly Gly Gly Gly Ser Gly Gly Gly Ser Gly Gly Gly Gly Ser
1               5                   10                  15

Gly Gly Gly Gly Ser Gly Gly Gly Gly Ser
            20                  25

<210> SEQ ID NO 26
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Thr Gly Gly Gly Gly Ser Gly Gly Gly Gly Ser Gly Gly Gly Gly Ser
1               5                   10                  15

Gly Gly Gly Gly Ser Gly Gly Gly Gly Ser Gly Gly Gly Gly Ser
            20                  25                  30

<210> SEQ ID NO 27
<211> LENGTH: 137
<212> TYPE: PRT
<213> ORGANISM: Homo sapiens

<400> SEQUENCE: 27

Thr Ile Pro Pro His Val Gln Lys Ser Val Asn Asn Asp Met Ile Val
1               5                   10                  15

Thr Asp Asn Asn Gly Ala Val Lys Phe Pro Gln Leu Cys Lys Phe Cys
            20                  25                  30

Asp Val Arg Phe Ser Thr Cys Asp Asn Gln Lys Ser Cys Met Ser Asn
```

```
            35                  40                  45
Cys Ser Ile Thr Ser Ile Cys Glu Lys Pro Gln Glu Val Cys Val Ala
        50                  55                  60
Val Trp Arg Lys Asn Asp Glu Asn Ile Thr Leu Glu Thr Val Cys His
 65                  70                  75                  80
Asp Pro Lys Leu Pro Tyr His Asp Phe Ile Leu Glu Asp Ala Ala Ser
                85                  90                  95
Pro Lys Cys Ile Met Lys Glu Lys Lys Pro Gly Glu Thr Phe Phe
            100                 105                 110
Met Cys Ser Cys Ser Ser Asp Glu Cys Asn Asp Asn Ile Ile Phe Ser
        115                 120                 125
Glu Glu Tyr Asn Thr Ser Asn Pro Asp
    130                 135
```

<210> SEQ ID NO 28
<211> LENGTH: 131
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

```
Gln Lys Ser Val Asn Asn Asp Met Ile Val Thr Asp Asn Asn Gly Ala
 1               5                  10                  15
Val Lys Phe Pro Gln Leu Cys Lys Phe Cys Asp Val Arg Phe Ser Thr
            20                  25                  30
Cys Asp Asn Gln Lys Ser Cys Met Ser Asn Cys Ser Ile Thr Ser Ile
        35                  40                  45
Cys Glu Lys Pro Gln Glu Val Cys Val Ala Val Trp Arg Lys Asn Asp
    50                  55                  60
Glu Asn Ile Thr Leu Glu Thr Val Cys His Asp Pro Lys Leu Pro Tyr
 65                  70                  75                  80
His Asp Phe Ile Leu Glu Asp Ala Ala Ser Pro Lys Cys Ile Met Lys
                85                  90                  95
Glu Lys Lys Pro Gly Glu Thr Phe Phe Met Cys Ser Cys Ser Ser
            100                 105                 110
Asp Glu Cys Asn Asp Asn Ile Ile Phe Ser Glu Glu Tyr Asn Thr Ser
        115                 120                 125
Asn Pro Asp
    130
```

<210> SEQ ID NO 29
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

```
Asp Met Ile Val Thr Asp Asn Asn Gly Ala Val Lys Phe Pro Gln Leu
 1               5                  10                  15
Cys Lys Phe Cys Asp Val Arg Phe Ser Thr Cys Asp Asn Gln Lys Ser
            20                  25                  30
Cys Met Ser Asn Cys Ser Ile Thr Ser Ile Cys Glu Lys Pro Gln Glu
        35                  40                  45
Val Cys Val Ala Val Trp Arg Lys Asn Asp Glu Asn Ile Thr Leu Glu
```

```
                   50                    55                   60

Thr Val Cys His Asp Pro Lys Leu Pro Tyr His Asp Phe Ile Leu Glu
 65                  70                   75                  80

Asp Ala Ala Ser Pro Lys Cys Ile Met Lys Glu Lys Lys Pro Gly
                 85                  90                  95

Glu Thr Phe Phe Met Cys Ser Cys Ser Ser Asp Glu Cys Asn Asp Asn
               100                 105                 110

Ile Ile Phe Ser Glu Glu Tyr Asn Thr Ser Asn Pro Asp
            115                 120                 125

<210> SEQ ID NO 30
<211> LENGTH: 131
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Thr Ile Pro Pro His Val Gln Lys Ser Val Asn Asn Asp Met Ile Val
  1               5                  10                  15

Thr Asp Asn Asn Gly Ala Val Lys Phe Pro Gln Leu Cys Lys Phe Cys
             20                  25                  30

Asp Val Arg Phe Ser Thr Cys Asp Asn Gln Lys Ser Cys Met Ser Asn
         35                  40                  45

Cys Ser Ile Thr Ser Ile Cys Glu Lys Pro Gln Glu Val Cys Val Ala
     50                  55                  60

Val Trp Arg Lys Asn Asp Glu Asn Ile Thr Leu Glu Thr Val Cys His
 65                  70                  75                  80

Asp Pro Lys Leu Pro Tyr His Asp Phe Ile Leu Glu Asp Ala Ala Ser
                 85                  90                  95

Pro Lys Cys Ile Met Lys Glu Lys Lys Pro Gly Glu Thr Phe Phe
               100                 105                 110

Met Cys Ser Cys Ser Ser Asp Glu Cys Asn Asp Asn Ile Ile Phe Ser
            115                 120                 125

Glu Glu Tyr
        130

<210> SEQ ID NO 31
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Gln Lys Ser Val Asn Asn Asp Met Ile Val Thr Asp Asn Asn Gly Ala
  1               5                  10                  15

Val Lys Phe Pro Gln Leu Cys Lys Phe Cys Asp Val Arg Phe Ser Thr
             20                  25                  30

Cys Asp Asn Gln Lys Ser Cys Met Ser Asn Cys Ser Ile Thr Ser Ile
         35                  40                  45

Cys Glu Lys Pro Gln Glu Val Cys Val Ala Val Trp Arg Lys Asn Asp
     50                  55                  60

Glu Asn Ile Thr Leu Glu Thr Val Cys His Asp Pro Lys Leu Pro Tyr
 65                  70                  75                  80

His Asp Phe Ile Leu Glu Asp Ala Ala Ser Pro Lys Cys Ile Met Lys
```

```
                    85                  90                  95

Glu Lys Lys Lys Pro Gly Glu Thr Phe Phe Met Cys Ser Cys Ser Ser
                100                 105                 110

Asp Glu Cys Asn Asp Asn Ile Ile Phe Ser Glu Glu Tyr
            115                 120                 125

<210> SEQ ID NO 32
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Asp Met Ile Val Thr Asp Asn Asn Gly Ala Val Lys Phe Pro Gln Leu
1               5                   10                  15

Cys Lys Phe Cys Asp Val Arg Phe Ser Thr Cys Asp Asn Gln Lys Ser
                20                  25                  30

Cys Met Ser Asn Cys Ser Ile Thr Ser Ile Cys Glu Lys Pro Gln Glu
            35                  40                  45

Val Cys Val Ala Val Trp Arg Lys Asn Asp Glu Asn Ile Thr Leu Glu
    50                  55                  60

Thr Val Cys His Asp Pro Lys Leu Pro Tyr His Asp Phe Ile Leu Glu
65                  70                  75                  80

Asp Ala Ala Ser Pro Lys Cys Ile Met Lys Glu Lys Lys Pro Gly
                85                  90                  95

Glu Thr Phe Phe Met Cys Ser Cys Ser Ser Asp Glu Cys Asn Asp Asn
                100                 105                 110

Ile Ile Phe Ser Glu Glu Tyr
            115

<210> SEQ ID NO 33
<211> LENGTH: 156
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

Gln Lys Ser Asp Val Glu Met Glu Ala Gln Lys Asp Glu Ile Ile Cys
1               5                   10                  15

Pro Ser Cys Asn Arg Thr Ala His Pro Leu Arg His Ile Asn Asn Asp
                20                  25                  30

Met Ile Val Thr Asp Asn Asn Gly Ala Val Lys Phe Pro Gln Leu Cys
            35                  40                  45

Lys Phe Cys Asp Val Arg Phe Ser Thr Cys Asp Asn Gln Lys Ser Cys
    50                  55                  60

Met Ser Asn Cys Ser Ile Thr Ser Ile Cys Glu Lys Pro Gln Glu Val
65                  70                  75                  80

Cys Val Ala Val Trp Arg Lys Asn Asp Glu Asn Ile Thr Leu Glu Thr
                85                  90                  95

Val Cys His Asp Pro Lys Leu Pro Tyr His Asp Phe Ile Leu Glu Asp
                100                 105                 110

Ala Ala Ser Pro Lys Cys Ile Met Lys Glu Lys Lys Pro Gly Glu
            115                 120                 125

Thr Phe Phe Met Cys Ser Cys Ser Ser Asp Glu Cys Asn Asp Asn Ile
```

```
               130                 135                 140
Ile Phe Ser Glu Glu Tyr Asn Thr Ser Asn Pro Asp
145                 150                 155

<210> SEQ ID NO 34
<211> LENGTH: 156
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

Thr Ile Pro Pro His Val Gln Lys Ser Asp Val Glu Met Glu Ala Gln
1               5                   10                  15

Lys Asp Glu Ile Ile Cys Pro Ser Cys Asn Arg Thr Ala His Pro Leu
                20                  25                  30

Arg His Ile Asn Asn Asp Met Ile Val Thr Asp Asn Asn Gly Ala Val
            35                  40                  45

Lys Phe Pro Gln Leu Cys Lys Phe Cys Asp Val Arg Phe Ser Thr Cys
    50                  55                  60

Asp Asn Gln Lys Ser Cys Met Ser Asn Cys Ser Ile Thr Ser Ile Cys
65                  70                  75                  80

Glu Lys Pro Gln Glu Val Cys Val Ala Val Trp Arg Lys Asn Asp Glu
                85                  90                  95

Asn Ile Thr Leu Glu Thr Val Cys His Asp Pro Lys Leu Pro Tyr His
            100                 105                 110

Asp Phe Ile Leu Glu Asp Ala Ala Ser Pro Lys Cys Ile Met Lys Glu
        115                 120                 125

Lys Lys Pro Gly Glu Thr Phe Phe Met Cys Ser Cys Ser Ser Asp
130                 135                 140

Glu Cys Asn Asp Asn Ile Ile Phe Ser Glu Glu Tyr
145                 150                 155

<210> SEQ ID NO 35
<211> LENGTH: 150
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

Gln Lys Ser Asp Val Glu Met Glu Ala Gln Lys Asp Glu Ile Ile Cys
1               5                   10                  15

Pro Ser Cys Asn Arg Thr Ala His Pro Leu Arg His Ile Asn Asn Asp
                20                  25                  30

Met Ile Val Thr Asp Asn Asn Gly Ala Val Lys Phe Pro Gln Leu Cys
            35                  40                  45

Lys Phe Cys Asp Val Arg Phe Ser Thr Cys Asp Asn Gln Lys Ser Cys
    50                  55                  60

Met Ser Asn Cys Ser Ile Thr Ser Ile Cys Glu Lys Pro Gln Glu Val
65                  70                  75                  80

Cys Val Ala Val Trp Arg Lys Asn Asp Glu Asn Ile Thr Leu Glu Thr
                85                  90                  95

Val Cys His Asp Pro Lys Leu Pro Tyr His Asp Phe Ile Leu Glu Asp
            100                 105                 110

Ala Ala Ser Pro Lys Cys Ile Met Lys Glu Lys Lys Pro Gly Glu
```

```
                115                 120                 125
Thr Phe Phe Met Cys Ser Cys Ser Ser Asp Glu Cys Asn Asp Asn Ile
    130                 135                 140

Ile Phe Ser Glu Glu Tyr
145                 150

<210> SEQ ID NO 36
<211> LENGTH: 137
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Thr Ile Pro Pro His Val Gln Lys Ser Val Asn Asn Asp Met Ile Val
1               5                   10                  15

Thr Asp Asn Asn Gly Ala Val Lys Phe Pro Gln Leu Cys Lys Phe Cys
            20                  25                  30

Asp Val Arg Phe Ser Thr Cys Asp Asn Gln Lys Ser Cys Met Ser Asn
        35                  40                  45

Cys Ser Ile Thr Ser Ile Cys Glu Lys Pro Gln Glu Val Cys Val Ala
    50                  55                  60

Val Trp Arg Lys Asn Asp Glu Asn Ile Thr Leu Glu Thr Val Cys His
65                  70                  75                  80

Asp Pro Lys Leu Pro Tyr His Lys Phe Ile Leu Glu Asp Ala Ala Ser
                85                  90                  95

Pro Lys Cys Ile Met Lys Glu Lys Lys Pro Gly Glu Thr Phe Phe
            100                 105                 110

Met Cys Ser Cys Ser Ser Asp Glu Cys Asn Asp Asn Ile Ile Phe Ser
        115                 120                 125

Glu Glu Tyr Asn Thr Ser Asn Pro Asp
    130                 135

<210> SEQ ID NO 37
<211> LENGTH: 162
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Thr Ile Pro Pro His Val Gln Lys Ser Asp Val Glu Met Glu Ala Gln
1               5                   10                  15

Lys Asp Glu Ile Ile Cys Pro Ser Cys Asn Arg Thr Ala His Pro Leu
            20                  25                  30

Arg His Ile Asn Asn Asp Met Ile Val Thr Asp Asn Asn Gly Ala Val
        35                  40                  45

Lys Phe Pro Gln Leu Cys Lys Phe Cys Asp Val Arg Phe Ser Thr Cys
    50                  55                  60

Asp Asn Gln Lys Ser Cys Met Ser Asn Cys Ser Ile Thr Ser Ile Cys
65                  70                  75                  80

Glu Lys Pro Gln Glu Val Cys Val Ala Val Trp Arg Lys Asn Asp Glu
                85                  90                  95

Asn Ile Thr Leu Glu Thr Val Cys His Asp Pro Lys Leu Pro Tyr His
                100                 105                 110

Lys Phe Ile Leu Glu Asp Ala Ala Ser Pro Lys Cys Ile Met Lys Glu
```

```
                115                 120                 125
Lys Lys Lys Pro Gly Glu Thr Phe Phe Met Cys Ser Cys Ser Ser Asp
            130                 135                 140

Glu Cys Asn Asp Asn Ile Ile Phe Ser Glu Glu Tyr Asn Thr Ser Asn
145                 150                 155                 160

Pro Asp

<210> SEQ ID NO 38
<211> LENGTH: 131
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Thr Ile Pro Pro His Val Gln Lys Ser Val Asn Asp Met Ile Val
1               5                   10                  15

Thr Asp Asn Asn Gly Ala Val Lys Phe Pro Gln Leu Cys Lys Phe Cys
            20                  25                  30

Asp Val Arg Phe Ser Thr Cys Asp Asn Gln Lys Ser Cys Met Ser Asp
        35                  40                  45

Cys Ser Ile Thr Ser Ile Cys Glu Lys Pro Gln Glu Val Cys Val Ala
    50                  55                  60

Val Trp Arg Lys Asn Asp Glu Asn Ile Thr Leu Glu Thr Val Cys His
65                  70                  75                  80

Asp Pro Lys Leu Pro Tyr His Asp Phe Ile Leu Glu Asp Ala Ala Ser
                85                  90                  95

Pro Lys Cys Ile Met Lys Glu Lys Lys Pro Gly Glu Thr Phe Phe
            100                 105                 110

Met Cys Ser Cys Ser Ser Asp Glu Cys Asn Asp Asn Ile Ile Phe Ser
        115                 120                 125

Glu Glu Tyr
    130

<210> SEQ ID NO 39
<211> LENGTH: 156
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

Thr Ile Pro Pro His Val Gln Lys Ser Asp Val Glu Met Glu Ala Gln
1               5                   10                  15

Lys Asp Glu Ile Ile Cys Pro Ser Cys Asn Arg Thr Ala His Pro Leu
            20                  25                  30

Arg His Ile Asn Asn Asp Met Ile Val Thr Asp Asn Asn Gly Ala Val
        35                  40                  45

Lys Phe Pro Gln Leu Cys Lys Phe Cys Asp Val Arg Phe Ser Thr Cys
    50                  55                  60

Asp Asn Gln Lys Ser Cys Met Ser Asp Cys Ser Ile Thr Ser Ile Cys
65                  70                  75                  80

Glu Lys Pro Gln Glu Val Cys Val Ala Val Trp Arg Lys Asn Asp Glu
                85                  90                  95

Asn Ile Thr Leu Glu Thr Val Cys His Asp Pro Lys Leu Pro Tyr His
            100                 105                 110
```

```
Asp Phe Ile Leu Glu Asp Ala Ala Ser Pro Lys Cys Ile Met Lys Glu
            115                 120                 125
Lys Lys Lys Pro Gly Glu Thr Phe Phe Met Cys Ser Cys Ser Ser Asp
130                 135                 140
Glu Cys Asn Asp Asn Ile Ile Phe Ser Glu Glu Tyr
145                 150                 155
```

<210> SEQ ID NO 40
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

```
Thr Gly Gly Gly Gly Ser Gly Gly Gly Gly Ser Gly Gly Gly Gly Ser
1               5                   10                  15
Gly Gly Gly Gly Ser Gly Gly Gly Ser Gly Gly Gly Gly Ser Gly
            20                  25                  30
Gly Gly Gly Ser
        35
```

<210> SEQ ID NO 41
<211> LENGTH: 36
<212> TYPE: PRT
<213> ORGANISM: Homo sapiens

<400> SEQUENCE: 41

```
Gly Arg Cys Lys Ile Arg His Ile Gly Ser Asn Asn Arg Leu Gln Arg
1               5                   10                  15
Ser Thr Cys Gln Asn Thr Gly Trp Glu Ser Ala His Val Met Lys Thr
            20                  25                  30
Pro Gly Phe Arg
        35
```

<210> SEQ ID NO 42
<211> LENGTH: 223
<212> TYPE: PRT
<213> ORGANISM: Homo sapiens

<400> SEQUENCE: 42

```
Val Glu Cys Pro Pro Cys Pro Ala Pro Pro Val Ala Gly Pro Ser Val
1               5                   10                  15
Phe Leu Phe Pro Pro Lys Pro Lys Asp Thr Leu Met Ile Ser Arg Thr
            20                  25                  30
Pro Glu Val Thr Cys Val Val Val Asp Val Ser His Glu Asp Pro Glu
        35                  40                  45
Val Gln Phe Asn Trp Tyr Val Asp Gly Val Glu Val His Asn Ala Lys
    50                  55                  60
Thr Lys Pro Arg Glu Glu Gln Phe Asn Ser Thr Phe Arg Val Val Ser
65                  70                  75                  80
Val Leu Thr Val Val His Gln Asp Trp Leu Asn Gly Lys Glu Tyr Lys
                85                  90                  95
Cys Lys Val Ser Asn Lys Gly Leu Pro Ala Pro Ile Glu Lys Thr Ile
            100                 105                 110
Ser Lys Thr Lys Gly Gln Pro Arg Glu Pro Gln Val Tyr Thr Leu Pro
        115                 120                 125
```

```
Pro Ser Arg Glu Glu Met Thr Lys Asn Gln Val Ser Leu Thr Cys Leu
    130                 135                 140
Val Lys Gly Phe Tyr Pro Ser Asp Ile Ala Val Glu Trp Glu Ser Asn
145                 150                 155                 160
Gly Gln Pro Glu Asn Asn Tyr Lys Thr Thr Pro Pro Met Leu Asp Ser
                165                 170                 175
Asp Gly Ser Phe Phe Leu Tyr Ser Lys Leu Thr Val Asp Lys Ser Arg
                180                 185                 190
Trp Gln Gln Gly Asn Val Phe Ser Cys Ser Val Met His Glu Ala Leu
                195                 200                 205
His Asn His Tyr Thr Gln Lys Ser Leu Ser Leu Ser Pro Gly Lys
    210                 215                 220

<210> SEQ ID NO 43
<211> LENGTH: 233
<212> TYPE: PRT
<213> ORGANISM: Homo sapiens

<400> SEQUENCE: 43

Gly Gly Pro Lys Ser Cys Asp Lys Thr His Thr Cys Pro Pro Cys Pro
1               5                   10                  15
Ala Pro Glu Leu Leu Gly Gly Pro Ser Val Phe Leu Phe Pro Pro Lys
                20                  25                  30
Pro Lys Asp Thr Leu Met Ile Ser Arg Thr Pro Glu Val Thr Cys Val
                35                  40                  45
Val Val Asp Val Ser His Glu Asp Pro Glu Val Lys Phe Asn Trp Tyr
50                  55                  60
Val Asp Gly Val Glu Val His Asn Ala Lys Thr Lys Pro Arg Glu Glu
65                  70                  75                  80
Gln Tyr Asn Ser Thr Tyr Arg Val Val Ser Val Leu Thr Val Leu His
                85                  90                  95
Gln Asp Trp Leu Asn Gly Lys Glu Tyr Lys Cys Lys Val Ser Asn Lys
                100                 105                 110
Ala Leu Pro Ala Pro Ile Glu Lys Thr Ile Ser Lys Ala Lys Gly Gln
                115                 120                 125
Pro Arg Glu Pro Gln Val Tyr Thr Leu Pro Pro Ser Arg Glu Glu Met
    130                 135                 140
Thr Lys Asn Gln Val Ser Leu Thr Cys Leu Val Lys Gly Phe Tyr Pro
145                 150                 155                 160
Ser Asp Ile Ala Val Glu Trp Glu Ser Asn Gly Gln Pro Glu Asn Asn
                165                 170                 175
Tyr Lys Thr Thr Pro Pro Val Leu Asp Ser Asp Gly Ser Phe Phe Leu
                180                 185                 190
Tyr Ser Lys Leu Thr Val Asp Lys Ser Arg Trp Gln Gln Gly Asn Val
                195                 200                 205
Phe Ser Cys Ser Val Met His Glu Ala Leu His Asn His Tyr Thr Gln
    210                 215                 220
Lys Ser Leu Ser Leu Ser Pro Gly Lys
225                 230

<210> SEQ ID NO 44
<211> LENGTH: 437
<212> TYPE: PRT
<213> ORGANISM: Artificial Sequence
<220> FEATURE:
<223> OTHER INFORMATION: Description of Artificial Sequence: Synthetic
      polypeptide
```

```
<400> SEQUENCE: 44

Met Asp Ala Met Lys Arg Gly Leu Cys Cys Val Leu Leu Leu Cys Gly
1               5                   10                  15

Ala Val Phe Val Ser Pro Gly Ala Thr Ile Pro Pro His Val Gln Lys
            20                  25                  30

Ser Asp Val Glu Met Glu Ala Gln Lys Asp Glu Ile Ile Cys Pro Ser
        35                  40                  45

Cys Asn Arg Thr Ala His Pro Leu Arg His Ile Asn Asn Asp Met Ile
    50                  55                  60

Val Thr Asp Asn Asn Gly Ala Val Lys Phe Pro Gln Leu Cys Lys Phe
65                  70                  75                  80

Cys Asp Val Arg Phe Ser Thr Cys Asp Asn Gln Lys Ser Cys Met Ser
                85                  90                  95

Asn Cys Ser Ile Thr Ser Ile Cys Glu Lys Pro Gln Glu Val Cys Val
            100                 105                 110

Ala Val Trp Arg Lys Asn Asp Glu Asn Ile Thr Leu Glu Thr Val Cys
        115                 120                 125

His Asp Pro Lys Leu Pro Tyr His Asp Phe Ile Leu Glu Asp Ala Ala
130                 135                 140

Ser Pro Lys Cys Ile Met Lys Glu Lys Lys Pro Gly Glu Thr Phe
145                 150                 155                 160

Phe Met Cys Ser Cys Ser Ser Asp Glu Cys Asn Asp Asn Ile Ile Phe
                165                 170                 175

Ser Glu Glu Tyr Asn Thr Ser Asn Pro Asp Thr Gly Gly Gly Gly Ser
            180                 185                 190

Gly Gly Gly Gly Ser Gly Gly Gly Ser Gly Gly Gly Ser Gly
        195                 200                 205

Gly Gly Gly Ser Thr His Thr Cys Pro Pro Cys Pro Ala Pro Glu Leu
210                 215                 220

Leu Gly Gly Pro Ser Val Phe Leu Phe Pro Pro Lys Pro Lys Asp Thr
225                 230                 235                 240

Leu Met Ile Ser Arg Thr Pro Glu Val Thr Cys Val Val Val Asp Val
                245                 250                 255

Ser His Glu Asp Pro Glu Val Lys Phe Asn Trp Tyr Val Asp Gly Val
            260                 265                 270

Glu Val His Asn Ala Lys Thr Lys Pro Arg Glu Glu Gln Tyr Asn Ser
        275                 280                 285

Thr Tyr Arg Val Val Ser Val Leu Thr Val Leu His Gln Asp Trp Leu
    290                 295                 300

Asn Gly Lys Glu Tyr Lys Cys Lys Val Ser Asn Lys Ala Leu Pro Ala
305                 310                 315                 320

Pro Ile Glu Lys Thr Ile Ser Lys Ala Lys Gly Gln Pro Arg Glu Pro
                325                 330                 335

Gln Val Tyr Thr Leu Pro Pro Ser Arg Glu Glu Met Thr Lys Asn Gln
            340                 345                 350

Val Ser Leu Thr Cys Leu Val Lys Gly Phe Tyr Pro Ser Asp Ile Ala
        355                 360                 365

Val Glu Trp Glu Ser Asn Gly Gln Pro Glu Asn Asn Tyr Lys Thr Thr
    370                 375                 380

Pro Pro Val Leu Asp Ser Asp Gly Ser Phe Phe Leu Tyr Ser Lys Leu
385                 390                 395                 400

Thr Val Asp Lys Ser Arg Trp Gln Gln Gly Asn Val Phe Ser Cys Ser
```

```
                    405                 410                 415
Val Met His Glu Ala Leu His Asn His Tyr Thr Gln Lys Ser Leu Ser
                420                 425                 430

Leu Ser Pro Gly Lys
            435

<210> SEQ ID NO 45
<211> LENGTH: 442
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45

Met Asp Ala Met Lys Arg Gly Leu Cys Cys Val Leu Leu Leu Cys Gly
1               5                   10                  15

Ala Val Phe Val Ser Pro Gly Ala Thr Ile Pro Pro His Val Gln Lys
                20                  25                  30

Ser Asp Val Glu Met Glu Ala Gln Lys Asp Glu Ile Ile Cys Pro Ser
            35                  40                  45

Cys Asn Arg Thr Ala His Pro Leu Arg His Ile Asn Asn Asp Met Ile
        50                  55                  60

Val Thr Asp Asn Asn Gly Ala Val Lys Phe Pro Gln Leu Cys Lys Phe
65                  70                  75                  80

Cys Asp Val Arg Phe Ser Thr Cys Asp Asn Gln Lys Ser Cys Met Ser
                85                  90                  95

Asn Cys Ser Ile Thr Ser Ile Cys Glu Lys Pro Gln Glu Val Cys Val
            100                 105                 110

Ala Val Trp Arg Lys Asn Asp Glu Asn Ile Thr Leu Glu Thr Val Cys
        115                 120                 125

His Asp Pro Lys Leu Pro Tyr His Asp Phe Ile Leu Glu Asp Ala Ala
130                 135                 140

Ser Pro Lys Cys Ile Met Lys Glu Lys Lys Pro Gly Glu Thr Phe
145                 150                 155                 160

Phe Met Cys Ser Cys Ser Ser Asp Glu Cys Asn Asp Asn Ile Ile Phe
                165                 170                 175

Ser Glu Glu Tyr Asn Thr Ser Asn Pro Asp Thr Gly Gly Gly Gly Ser
            180                 185                 190

Gly Gly Gly Gly Ser Gly Gly Gly Ser Gly Gly Gly Gly Ser Gly
        195                 200                 205

Gly Gly Gly Ser Gly Gly Gly Gly Ser Thr His Thr Cys Pro Pro Cys
210                 215                 220

Pro Ala Pro Glu Leu Leu Gly Gly Pro Ser Val Phe Leu Phe Pro Pro
225                 230                 235                 240

Lys Pro Lys Asp Thr Leu Met Ile Ser Arg Thr Pro Glu Val Thr Cys
                245                 250                 255

Val Val Val Asp Val Ser His Glu Asp Pro Glu Val Lys Phe Asn Trp
            260                 265                 270

Tyr Val Asp Gly Val Glu Val His Asn Ala Lys Thr Lys Pro Arg Glu
        275                 280                 285

Glu Gln Tyr Asn Ser Thr Tyr Arg Val Val Ser Val Leu Thr Val Leu
    290                 295                 300

His Gln Asp Trp Leu Asn Gly Lys Glu Tyr Lys Cys Lys Val Ser Asn
305                 310                 315                 320
```

```
Lys Ala Leu Pro Ala Pro Ile Glu Lys Thr Ile Ser Lys Ala Lys Gly
            325                 330                 335

Gln Pro Arg Glu Pro Gln Val Tyr Thr Leu Pro Pro Ser Arg Glu Glu
        340                 345                 350

Met Thr Lys Asn Gln Val Ser Leu Thr Cys Leu Val Lys Gly Phe Tyr
            355                 360                 365

Pro Ser Asp Ile Ala Val Glu Trp Glu Ser Asn Gly Gln Pro Glu Asn
        370                 375                 380

Asn Tyr Lys Thr Thr Pro Pro Val Leu Asp Ser Asp Gly Ser Phe Phe
385                 390                 395                 400

Leu Tyr Ser Lys Leu Thr Val Asp Lys Ser Arg Trp Gln Gln Gly Asn
                405                 410                 415

Val Phe Ser Cys Ser Val Met His Glu Ala Leu His Asn His Tyr Thr
            420                 425                 430

Gln Lys Ser Leu Ser Leu Ser Pro Gly Lys
        435                 440
```

<210> SEQ ID NO 46
<211> LENGTH: 1314
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 46

```
atggatgcaa tgaagagagg gctctgctgt gtgctgctgc tgtgtggagc agtcttcgtt    60
tcgcccggcg ccacgatccc accgcacgtt cagaagtcgg atgtggaaat ggaggcccag   120
aaagatgaaa tcatctgccc cagctgtaat aggactgccc atccactgag acatattaat   180
aacgacatga tagtcactga caacaacggt gcagtcaagt tccacaact gtgtaaattt   240
tgtgatgtga gattttccac ctgtgacaac cagaaatcct gcatgagcaa ctgcagcatc   300
acctccatct gtgagaagcc acaggaagtc tgtgtggctg tatggagaaa gaatgacgag   360
aacataacac tagagacagt ttgccatgac cccaagctcc cctaccatga ctttattctg   420
gaagatgctg cttctccaaa gtgcattatg aaggaaaaaa aaaagcctgg tgagactttc   480
ttcatgtgtt cctgtagctc tgatgagtgc aatgacaaca tcatcttctc agaagaatat   540
aacaccagca atcctgacac cggtggagga ggttctggtg gtggaggttc tggaggtgga   600
ggaagtggtg gaggtggttc tggaggtggt ggaagtactc acacatgccc accgtgccca   660
gcacctgaac tcctgggggg accgtcagtc ttcctcttcc ccccaaaacc caaggacacc   720
ctcatgatct cccggacccc tgaggtcaca tgcgtggtgg tggacgtgag ccacgaagac   780
cctgaggtca agttcaactg gtacgtggac ggcgtggagg tgcataatgc caagacaaag   840
ccgcgggagg agcagtacaa cagcacgtac cgtgtggtca gcgtcctcac cgtcctgcac   900
caggactggc tgaatggcaa ggagtacaag tgcaaggtct ccaacaaagc cctcccagcc   960
cccatcgaga aaaccatctc caaagccaaa gggcagcccc gagaaccaca ggtgtacacc  1020
ctgcccccat cccgggagga gatgaccaag aaccaggtca gcctgacctg cctggtcaaa  1080
ggcttctatc ccagcgacat cgccgtggag tgggagagca atgggcagcc ggagaacaac  1140
tacaagacca cgcctcccgt gctggactcc gacggctcct tcttcctcta tagcaagctc  1200
accgtggaca gagcaggtg gcagcagggg aacgtcttct catgctccgt gatgcatgag  1260
gctctgcaca accactacac gcagaagagc ctctccctgt ctccgggtaa atga        1314
```

<210> SEQ ID NO 47
<211> LENGTH: 1329
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 47

| | |
|---|---|
| atggatgcaa tgaagagagg gctctgctgt gtgctgctgc tgtgtggagc agtcttcgtt | 60 |
| tcgcccggcg ccacgatccc accgcacgtt cagaagtcgg atgtggaaat ggaggcccag | 120 |
| aaagatgaaa tcatctgccc cagctgtaat aggactgccc atccactgag acatattaat | 180 |
| aacgacatga tagtcactga caacaacggt gcagtcaagt ttccacaact gtgtaaattt | 240 |
| tgtgatgtga gattttccac tgtgacaaca cagaaatcct gcatgagcaa ctgcagcatc | 300 |
| acctccatct gtgagaagcc acaggaagtc tgtgtggctg tatggagaaa gaatgacgag | 360 |
| aacataacac tagagacagt ttgccatgac cccaagctcc cctaccatga ctttattctg | 420 |
| gaagatgctg cttctccaaa gtgcattatg aaggaaaaaa aaaagcctgg tgagactttc | 480 |
| ttcatgtgtt cctgtagctc tgatgagtgc aatgacaaca tcatcttctc agaagaatat | 540 |
| aacaccagca atcctgacac cggtggaggt ggaagtggtg gaggaggttc tggtggtgga | 600 |
| ggttctggag gtggaggaag tggtggaggt ggttctggag gtggtggaag tactcacaca | 660 |
| tgcccaccgt gcccagcacc tgaactcctg ggggaccgt cagtcttcct cttccccca | 720 |
| aaacccaagg acaccctcat gatctcccgg acccctgagg tcacatgcgt ggtggtggac | 780 |
| gtgagccacg aagaccctga ggtcaagttc aactggtacg tggacggcgt ggaggtgcat | 840 |
| aatgccaaga caaagccgcg ggaggagcag tacaacagca cgtaccgtgt ggtcagcgtc | 900 |
| ctcaccgtcc tgcaccagga ctggctgaat ggcaaggagt acaagtgcaa ggtctccaac | 960 |
| aaagccctcc cagcccccat cgagaaaacc atctccaaag ccaagggca gccccgagaa | 1020 |
| ccacaggtgt acaccctgcc cccatcccgg gaggagatga ccaagaacca ggtcagcctg | 1080 |
| acctgcctgg tcaaaggctt ctatcccagc gacatcgccg tggagtggga gagcaatggg | 1140 |
| cagccggaga acaactacaa gaccacgcct cccgtgctgg actccgacgg ctccttcttc | 1200 |
| ctctatagca agctcaccgt ggacaagagc aggtggcagc aggggaacgt cttctcatgc | 1260 |
| tccgtgatgc atgaggctct gcacaaccac tacacgcaga gagcctctc cctgtctccg | 1320 |
| ggtaaatga | 1329 |

<210> SEQ ID NO 48
<211> LENGTH: 408
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 48

Thr Ile Pro Pro His Val Gln Lys Ser Asp Val Glu Met Glu Ala Gln
1               5                   10                  15

Lys Asp Glu Ile Ile Cys Pro Ser Cys Asn Arg Thr Ala His Pro Leu
            20                  25                  30

Arg His Ile Asn Asn Asp Met Ile Val Thr Asp Asn Asn Gly Ala Val
        35                  40                  45

Lys Phe Pro Gln Leu Cys Lys Phe Cys Asp Val Arg Phe Ser Thr Cys
    50                  55                  60

Asp Asn Gln Lys Ser Cys Met Ser Asn Cys Ser Ile Thr Ser Ile Cys
65                  70                  75                  80

Glu Lys Pro Gln Glu Val Cys Val Ala Val Trp Arg Lys Asn Asp Glu
            85                  90                  95

Asn Ile Thr Leu Glu Thr Val Cys His Asp Pro Lys Leu Pro Tyr His
        100                 105                 110

Asp Phe Ile Leu Glu Asp Ala Ala Ser Pro Lys Cys Ile Met Lys Glu
    115                 120                 125

Lys Lys Lys Pro Gly Glu Thr Phe Phe Met Cys Ser Cys Ser Ser Asp
130                 135                 140

Glu Cys Asn Asp Asn Ile Ile Phe Ser Glu Glu Tyr Asn Thr Ser Asn
145                 150                 155                 160

Pro Asp Thr Gly Gly Gly Gly Ser Gly Gly Gly Gly Ser Gly Gly Gly
            165                 170                 175

Gly Ser Gly Gly Gly Gly Ser Thr His Thr Cys Pro Pro Cys Pro Ala
            180                 185                 190

Pro Glu Leu Leu Gly Gly Pro Ser Val Phe Leu Phe Pro Pro Lys Pro
            195                 200                 205

Lys Asp Thr Leu Met Ile Ser Arg Thr Pro Glu Val Thr Cys Val Val
210                 215                 220

Val Asp Val Ser His Glu Asp Pro Glu Val Lys Phe Asn Trp Tyr Val
225                 230                 235                 240

Asp Gly Val Glu Val His Asn Ala Lys Thr Lys Pro Arg Glu Glu Gln
            245                 250                 255

Tyr Asn Ser Thr Tyr Arg Val Val Ser Val Leu Thr Val Leu His Gln
            260                 265                 270

Asp Trp Leu Asn Gly Lys Glu Tyr Lys Cys Lys Val Ser Asn Lys Ala
            275                 280                 285

Leu Pro Ala Pro Ile Glu Lys Thr Ile Ser Lys Ala Lys Gly Gln Pro
            290                 295                 300

Arg Glu Pro Gln Val Tyr Thr Leu Pro Pro Ser Arg Glu Glu Met Thr
305                 310                 315                 320

Lys Asn Gln Val Ser Leu Thr Cys Leu Val Lys Gly Phe Tyr Pro Ser
            325                 330                 335

Asp Ile Ala Val Glu Trp Glu Ser Asn Gly Gln Pro Glu Asn Asn Tyr
            340                 345                 350

Lys Thr Thr Pro Pro Val Leu Asp Ser Asp Gly Ser Phe Phe Leu Tyr
            355                 360                 365

Ser Lys Leu Thr Val Asp Lys Ser Arg Trp Gln Gln Gly Asn Val Phe
            370                 375                 380

Ser Cys Ser Val Met His Glu Ala Leu His Asn His Tyr Thr Gln Lys
385                 390                 395                 400

Ser Leu Ser Leu Ser Pro Gly Lys
                405

<210> SEQ ID NO 49
<211> LENGTH: 162
<212> TYPE: PRT
<213> ORGANISM: Homo sapiens

<400> SEQUENCE: 49

Thr Ile Pro Pro His Val Gln Lys Ser Asp Val Glu Met Glu Ala Gln
1               5                   10                  15

Lys Asp Glu Ile Ile Cys Pro Ser Cys Asn Arg Thr Ala His Pro Leu

```
                   20                  25                  30
Arg His Ile Asn Asn Asp Met Ile Val Thr Asp Asn Asn Gly Ala Val
            35                  40                  45

Lys Phe Pro Gln Leu Cys Lys Phe Cys Asp Val Arg Phe Ser Thr Cys
    50                  55                  60

Asp Asn Gln Lys Ser Cys Met Ser Asn Cys Ser Ile Thr Ser Ile Cys
65                  70                  75                  80

Glu Lys Pro Gln Glu Val Cys Val Ala Val Trp Arg Lys Asn Asp Glu
                85                  90                  95

Asn Ile Thr Leu Glu Thr Val Cys His Asp Pro Lys Leu Pro Tyr His
            100                 105                 110

Asp Phe Ile Leu Glu Asp Ala Ala Ser Pro Lys Cys Ile Met Lys Glu
        115                 120                 125

Lys Lys Lys Pro Gly Glu Thr Phe Phe Met Cys Ser Cys Ser Ser Asp
    130                 135                 140

Glu Cys Asn Asp Asn Ile Ile Phe Ser Glu Glu Tyr Asn Thr Ser Asn
145                 150                 155                 160

Pro Asp

<210> SEQ ID NO 50
<211> LENGTH: 410
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50

Gly Ala Thr Ile Pro Pro His Val Gln Lys Ser Asp Val Glu Met Glu
1               5                   10                  15

Ala Gln Lys Asp Glu Ile Ile Cys Pro Ser Cys Asn Arg Thr Ala His
            20                  25                  30

Pro Leu Arg His Ile Asn Asn Asp Met Ile Val Thr Asp Asn Asn Gly
        35                  40                  45

Ala Val Lys Phe Pro Gln Leu Cys Lys Phe Cys Asp Val Arg Phe Ser
    50                  55                  60

Thr Cys Asp Asn Gln Lys Ser Cys Met Ser Asn Cys Ser Ile Thr Ser
65                  70                  75                  80

Ile Cys Glu Lys Pro Gln Glu Val Cys Val Ala Val Trp Arg Lys Asn
                85                  90                  95

Asp Glu Asn Ile Thr Leu Glu Thr Val Cys His Asp Pro Lys Leu Pro
            100                 105                 110

Tyr His Asp Phe Ile Leu Glu Asp Ala Ala Ser Pro Lys Cys Ile Met
        115                 120                 125

Lys Glu Lys Lys Lys Pro Gly Glu Thr Phe Phe Met Cys Ser Cys Ser
    130                 135                 140

Ser Asp Glu Cys Asn Asp Asn Ile Ile Phe Ser Glu Glu Tyr Asn Thr
145                 150                 155                 160

Ser Asn Pro Asp Thr Gly Gly Gly Ser Gly Gly Gly Ser Gly
                165                 170                 175

Gly Gly Gly Ser Gly Gly Gly Ser Thr His Thr Cys Pro Pro Cys
            180                 185                 190

Pro Ala Pro Glu Leu Leu Gly Gly Pro Ser Val Phe Leu Phe Pro Pro
        195                 200                 205

Lys Pro Lys Asp Thr Leu Met Ile Ser Arg Thr Pro Glu Val Thr Cys
```

```
            210                 215                 220
Val Val Val Asp Val Ser His Glu Asp Pro Glu Val Lys Phe Asn Trp
225                 230                 235                 240

Tyr Val Asp Gly Val Glu Val His Asn Ala Lys Thr Lys Pro Arg Glu
                245                 250                 255

Glu Gln Tyr Asn Ser Thr Tyr Arg Val Val Ser Val Leu Thr Val Leu
            260                 265                 270

His Gln Asp Trp Leu Asn Gly Lys Glu Tyr Lys Cys Lys Val Ser Asn
        275                 280                 285

Lys Ala Leu Pro Ala Pro Ile Glu Lys Thr Ile Ser Lys Ala Lys Gly
    290                 295                 300

Gln Pro Arg Glu Pro Gln Val Tyr Thr Leu Pro Pro Ser Arg Glu Glu
305                 310                 315                 320

Met Thr Lys Asn Gln Val Ser Leu Thr Cys Leu Val Lys Gly Phe Tyr
                325                 330                 335

Pro Ser Asp Ile Ala Val Glu Trp Glu Ser Asn Gly Gln Pro Glu Asn
            340                 345                 350

Asn Tyr Lys Thr Thr Pro Pro Val Leu Asp Ser Asp Gly Ser Phe Phe
        355                 360                 365

Leu Tyr Ser Lys Leu Thr Val Asp Lys Ser Arg Trp Gln Gln Gly Asn
    370                 375                 380

Val Phe Ser Cys Ser Val Met His Glu Ala Leu His Asn His Tyr Thr
385                 390                 395                 400

Gln Lys Ser Leu Ser Leu Ser Pro Gly Lys
                405                 410

<210> SEQ ID NO 51
<211> LENGTH: 408
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 51

Thr Ile Pro Pro His Val Gln Lys Ser Asp Val Glu Met Glu Ala Gln
1               5                   10                  15

Lys Asp Glu Ile Ile Cys Pro Ser Cys Asn Arg Thr Ala His Pro Leu
            20                  25                  30

Arg His Ile Asn Asn Asp Met Ile Val Thr Asp Asn Asn Gly Ala Val
        35                  40                  45

Lys Phe Pro Gln Leu Cys Lys Phe Cys Asp Val Arg Phe Ser Thr Cys
    50                  55                  60

Asp Asn Gln Lys Ser Cys Met Ser Asn Cys Ser Ile Thr Ser Ile Cys
65                  70                  75                  80

Glu Lys Pro Gln Glu Val Cys Val Ala Val Trp Arg Lys Asn Asp Glu
                85                  90                  95

Asn Ile Thr Leu Glu Thr Val Cys His Asp Pro Lys Leu Pro Tyr His
            100                 105                 110

Asp Phe Ile Leu Glu Asp Ala Ala Ser Pro Lys Cys Ile Met Lys Glu
        115                 120                 125

Lys Lys Lys Pro Gly Glu Thr Phe Phe Met Cys Ser Cys Ser Ser Asp
    130                 135                 140

Glu Cys Asn Asp Asn Ile Ile Phe Ser Glu Glu Tyr Asn Thr Ser Asn
145                 150                 155                 160
```

```
Pro Asp Thr Gly Gly Gly Ser Gly Gly Gly Ser Gly Gly Gly
            165                 170                 175

Gly Ser Gly Gly Gly Ser Thr His Thr Cys Pro Cys Pro Ala
            180                 185                 190

Pro Glu Leu Leu Gly Gly Pro Ser Val Phe Leu Phe Pro Pro Lys Pro
            195                 200                 205

Lys Asp Thr Leu Met Ile Ser Arg Thr Pro Glu Val Thr Cys Val Val
210                 215                 220

Val Asp Val Ser His Glu Asp Pro Glu Val Lys Phe Asn Trp Tyr Val
225                 230                 235                 240

Asp Gly Val Glu Val His Asn Ala Lys Thr Lys Pro Arg Glu Glu Gln
            245                 250                 255

Tyr Asn Ser Thr Tyr Arg Val Val Ser Val Leu Thr Val Leu His Gln
            260                 265                 270

Asp Trp Leu Asn Gly Lys Glu Tyr Lys Cys Lys Val Ser Asn Lys Ala
    275                 280                 285

Leu Pro Ala Pro Ile Glu Lys Thr Ile Ser Lys Ala Lys Gly Gln Pro
    290                 295                 300

Arg Glu Pro Gln Val Tyr Thr Leu Pro Pro Ser Arg Glu Glu Met Thr
305                 310                 315                 320

Lys Asn Gln Val Ser Leu Thr Cys Leu Val Lys Gly Phe Tyr Pro Ser
            325                 330                 335

Asp Ile Ala Val Glu Trp Glu Ser Asn Gly Gln Pro Glu Asn Asn Tyr
            340                 345                 350

Lys Thr Thr Pro Pro Val Leu Asp Ser Asp Gly Ser Phe Phe Leu Tyr
            355                 360                 365

Ser Lys Leu Thr Val Asp Lys Ser Arg Trp Gln Gln Gly Asn Val Phe
370                 375                 380

Ser Cys Ser Val Met His Glu Ala Leu His Asn His Tyr Thr Gln Lys
385                 390                 395                 400

Ser Leu Ser Leu Ser Pro Gly Lys
            405

<210> SEQ ID NO 52
<211> LENGTH: 409
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 52

Ala Thr Ile Pro Pro His Val Gln Lys Ser Asp Val Glu Met Glu Ala
1               5                   10                  15

Gln Lys Asp Glu Ile Ile Cys Pro Ser Cys Asn Arg Thr Ala His Pro
            20                  25                  30

Leu Arg His Ile Asn Asn Asp Met Ile Val Thr Asp Asn Asn Gly Ala
        35                  40                  45

Val Lys Phe Pro Gln Leu Cys Lys Phe Cys Asp Val Arg Phe Ser Thr
    50                  55                  60

Cys Asp Asn Gln Lys Ser Cys Met Ser Asn Cys Ser Ile Thr Ser Ile
65                  70                  75                  80

Cys Glu Lys Pro Gln Glu Val Cys Val Ala Val Trp Arg Lys Asn Asp
            85                  90                  95

Glu Asn Ile Thr Leu Glu Thr Val Cys His Asp Pro Lys Leu Pro Tyr
            100                 105                 110
```

His Asp Phe Ile Leu Glu Asp Ala Ala Ser Pro Lys Cys Ile Met Lys
            115                 120                 125

Glu Lys Lys Pro Gly Glu Thr Phe Phe Met Cys Ser Cys Ser Ser
        130                 135                 140

Asp Glu Cys Asn Asp Asn Ile Ile Phe Ser Glu Glu Tyr Asn Thr Ser
145                 150                 155                 160

Asn Pro Asp Thr Gly Gly Gly Ser Gly Gly Gly Ser Gly Gly
                165                 170                 175

Gly Gly Ser Gly Gly Gly Gly Ser Thr His Thr Cys Pro Pro Cys Pro
                180                 185                 190

Ala Pro Glu Leu Leu Gly Gly Pro Ser Val Phe Leu Phe Pro Pro Lys
                195                 200                 205

Pro Lys Asp Thr Leu Met Ile Ser Arg Thr Pro Glu Val Thr Cys Val
        210                 215                 220

Val Val Asp Val Ser His Glu Asp Pro Glu Val Lys Phe Asn Trp Tyr
225                 230                 235                 240

Val Asp Gly Val Glu Val His Asn Ala Lys Thr Lys Pro Arg Glu Glu
                245                 250                 255

Gln Tyr Asn Ser Thr Tyr Arg Val Val Ser Val Leu Thr Val Leu His
                260                 265                 270

Gln Asp Trp Leu Asn Gly Lys Glu Tyr Lys Cys Lys Val Ser Asn Lys
        275                 280                 285

Ala Leu Pro Ala Pro Ile Glu Lys Thr Ile Ser Lys Ala Lys Gly Gln
        290                 295                 300

Pro Arg Glu Pro Gln Val Tyr Thr Leu Pro Pro Ser Arg Glu Glu Met
305                 310                 315                 320

Thr Lys Asn Gln Val Ser Leu Thr Cys Leu Val Lys Gly Phe Tyr Pro
                325                 330                 335

Ser Asp Ile Ala Val Glu Trp Glu Ser Asn Gly Gln Pro Glu Asn Asn
                340                 345                 350

Tyr Lys Thr Thr Pro Pro Val Leu Asp Ser Asp Gly Ser Phe Phe Leu
        355                 360                 365

Tyr Ser Lys Leu Thr Val Asp Lys Ser Arg Trp Gln Gln Gly Asn Val
        370                 375                 380

Phe Ser Cys Ser Val Met His Glu Ala Leu His Asn His Tyr Thr Gln
385                 390                 395                 400

Lys Ser Leu Ser Leu Ser Pro Gly Lys
                405

<210> SEQ ID NO 53
<211> LENGTH: 407
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 53

Ile Pro Pro His Val Gln Lys Ser Asp Val Glu Met Glu Ala Gln Lys
1               5                   10                  15

Asp Glu Ile Ile Cys Pro Ser Cys Asn Arg Thr Ala His Pro Leu Arg
            20                  25                  30

His Ile Asn Asn Asp Met Ile Val Thr Asp Asn Asn Gly Ala Val Lys
        35                  40                  45

Phe Pro Gln Leu Cys Lys Phe Cys Asp Val Arg Phe Ser Thr Cys Asp

```
                 50                  55                  60
Asn Gln Lys Ser Cys Met Ser Asn Cys Ser Ile Thr Ser Ile Cys Glu
 65                  70                  75                  80

Lys Pro Gln Glu Val Cys Val Ala Val Trp Arg Lys Asn Asp Glu Asn
                 85                  90                  95

Ile Thr Leu Glu Thr Val Cys His Asp Pro Lys Leu Pro Tyr His Asp
            100                 105                 110

Phe Ile Leu Glu Asp Ala Ala Ser Pro Lys Cys Ile Met Lys Glu Lys
        115                 120                 125

Lys Lys Pro Gly Glu Thr Phe Phe Met Cys Ser Cys Ser Ser Asp Glu
130                 135                 140

Cys Asn Asp Asn Ile Ile Phe Ser Glu Glu Tyr Asn Thr Ser Asn Pro
145                 150                 155                 160

Asp Thr Gly Gly Gly Ser Gly Gly Gly Ser Gly Gly Gly Gly
                165                 170                 175

Ser Gly Gly Gly Gly Ser Thr His Thr Cys Pro Pro Cys Pro Ala Pro
            180                 185                 190

Glu Leu Leu Gly Gly Pro Ser Val Phe Leu Phe Pro Pro Lys Pro Lys
        195                 200                 205

Asp Thr Leu Met Ile Ser Arg Thr Pro Glu Val Thr Cys Val Val Val
    210                 215                 220

Asp Val Ser His Glu Asp Pro Glu Val Lys Phe Asn Trp Tyr Val Asp
225                 230                 235                 240

Gly Val Glu Val His Asn Ala Lys Thr Lys Pro Arg Glu Glu Gln Tyr
                245                 250                 255

Asn Ser Thr Tyr Arg Val Val Ser Val Leu Thr Val Leu His Gln Asp
            260                 265                 270

Trp Leu Asn Gly Lys Glu Tyr Lys Cys Lys Val Ser Asn Lys Ala Leu
        275                 280                 285

Pro Ala Pro Ile Glu Lys Thr Ile Ser Lys Ala Lys Gly Gln Pro Arg
    290                 295                 300

Glu Pro Gln Val Tyr Thr Leu Pro Pro Ser Arg Glu Glu Met Thr Lys
305                 310                 315                 320

Asn Gln Val Ser Leu Thr Cys Leu Val Lys Gly Phe Tyr Pro Ser Asp
                325                 330                 335

Ile Ala Val Glu Trp Glu Ser Asn Gly Gln Pro Glu Asn Asn Tyr Lys
            340                 345                 350

Thr Thr Pro Pro Val Leu Asp Ser Asp Gly Ser Phe Phe Leu Tyr Ser
        355                 360                 365

Lys Leu Thr Val Asp Lys Ser Arg Trp Gln Gln Gly Asn Val Phe Ser
    370                 375                 380

Cys Ser Val Met His Glu Ala Leu His Asn His Tyr Thr Gln Lys Ser
385                 390                 395                 400

Leu Ser Leu Ser Pro Gly Lys
                405

<210> SEQ ID NO 54
<211> LENGTH: 406
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 54
```

```
Pro Pro His Val Gln Lys Ser Asp Val Glu Met Glu Ala Gln Lys Asp
1               5                   10                  15
Glu Ile Ile Cys Pro Ser Cys Asn Arg Thr Ala His Pro Leu Arg His
            20                  25                  30
Ile Asn Asn Asp Met Ile Val Thr Asp Asn Asn Gly Ala Val Lys Phe
        35                  40                  45
Pro Gln Leu Cys Lys Phe Cys Asp Val Arg Phe Ser Thr Cys Asp Asn
    50              55                  60
Gln Lys Ser Cys Met Ser Asn Cys Ser Ile Thr Ser Ile Cys Glu Lys
65              70                  75                  80
Pro Gln Glu Val Cys Val Ala Val Trp Arg Lys Asn Asp Glu Asn Ile
                85                  90                  95
Thr Leu Glu Thr Val Cys His Asp Pro Lys Leu Pro Tyr His Asp Phe
            100                 105                 110
Ile Leu Glu Asp Ala Ala Ser Pro Lys Cys Ile Met Lys Glu Lys Lys
        115                 120                 125
Lys Pro Gly Glu Thr Phe Phe Met Cys Ser Cys Ser Ser Asp Glu Cys
    130                 135                 140
Asn Asp Asn Ile Ile Phe Ser Glu Glu Tyr Asn Thr Ser Asn Pro Asp
145                 150                 155                 160
Thr Gly Gly Gly Gly Ser Gly Gly Gly Ser Gly Gly Gly Gly Gly Ser
                165                 170                 175
Gly Gly Gly Gly Ser Thr His Thr Cys Pro Pro Cys Pro Ala Pro Glu
            180                 185                 190
Leu Leu Gly Gly Pro Ser Val Phe Leu Phe Pro Pro Lys Pro Lys Asp
    195                 200                 205
Thr Leu Met Ile Ser Arg Thr Pro Glu Val Thr Cys Val Val Val Asp
    210                 215                 220
Val Ser His Glu Asp Pro Glu Val Lys Phe Asn Trp Tyr Val Asp Gly
225                 230                 235                 240
Val Glu Val His Asn Ala Lys Thr Lys Pro Arg Glu Glu Gln Tyr Asn
                245                 250                 255
Ser Thr Tyr Arg Val Val Ser Val Leu Thr Val Leu His Gln Asp Trp
            260                 265                 270
Leu Asn Gly Lys Glu Tyr Lys Cys Lys Val Ser Asn Lys Ala Leu Pro
    275                 280                 285
Ala Pro Ile Glu Lys Thr Ile Ser Lys Ala Lys Gly Gln Pro Arg Glu
    290                 295                 300
Pro Gln Val Tyr Thr Leu Pro Pro Ser Arg Glu Glu Met Thr Lys Asn
305                 310                 315                 320
Gln Val Ser Leu Thr Cys Leu Val Lys Gly Phe Tyr Pro Ser Asp Ile
                325                 330                 335
Ala Val Glu Trp Glu Ser Asn Gly Gln Pro Glu Asn Asn Tyr Lys Thr
            340                 345                 350
Thr Pro Pro Val Leu Asp Ser Asp Gly Ser Phe Phe Leu Tyr Ser Lys
    355                 360                 365
Leu Thr Val Asp Lys Ser Arg Trp Gln Gln Gly Asn Val Phe Ser Cys
    370                 375                 380
Ser Val Met His Glu Ala Leu His Asn His Tyr Thr Gln Lys Ser Leu
385                 390                 395                 400
Ser Leu Ser Pro Gly Lys
            405
```

```
<210> SEQ ID NO 55
<211> LENGTH: 405
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 55

Pro His Val Gln Lys Ser Asp Val Glu Met Glu Ala Gln Lys Asp Glu
1               5                   10                  15

Ile Ile Cys Pro Ser Cys Asn Arg Thr Ala His Pro Leu Arg His Ile
            20                  25                  30

Asn Asn Asp Met Ile Val Thr Asp Asn Asn Gly Ala Val Lys Phe Pro
        35                  40                  45

Gln Leu Cys Lys Phe Cys Asp Val Arg Phe Ser Thr Cys Asp Asn Gln
    50                  55                  60

Lys Ser Cys Met Ser Asn Cys Ser Ile Thr Ser Ile Cys Glu Lys Pro
65                  70                  75                  80

Gln Glu Val Cys Val Ala Val Trp Arg Lys Asn Asp Glu Asn Ile Thr
                85                  90                  95

Leu Glu Thr Val Cys His Asp Pro Lys Leu Pro Tyr His Asp Phe Ile
            100                 105                 110

Leu Glu Asp Ala Ala Ser Pro Lys Cys Ile Met Lys Glu Lys Lys Lys
        115                 120                 125

Pro Gly Glu Thr Phe Phe Met Cys Ser Cys Ser Ser Asp Glu Cys Asn
    130                 135                 140

Asp Asn Ile Ile Phe Ser Glu Glu Tyr Asn Thr Ser Asn Pro Asp Thr
145                 150                 155                 160

Gly Gly Gly Gly Ser Gly Gly Gly Ser Gly Gly Gly Gly Ser Gly
                165                 170                 175

Gly Gly Gly Ser Thr His Thr Cys Pro Pro Cys Pro Ala Pro Glu Leu
            180                 185                 190

Leu Gly Gly Pro Ser Val Phe Leu Phe Pro Pro Lys Pro Lys Asp Thr
        195                 200                 205

Leu Met Ile Ser Arg Thr Pro Glu Val Thr Cys Val Val Val Asp Val
    210                 215                 220

Ser His Glu Asp Pro Glu Val Lys Phe Asn Trp Tyr Val Asp Gly Val
225                 230                 235                 240

Glu Val His Asn Ala Lys Thr Lys Pro Arg Glu Glu Gln Tyr Asn Ser
                245                 250                 255

Thr Tyr Arg Val Val Ser Val Leu Thr Val Leu His Gln Asp Trp Leu
            260                 265                 270

Asn Gly Lys Glu Tyr Lys Cys Lys Val Ser Asn Lys Ala Leu Pro Ala
        275                 280                 285

Pro Ile Glu Lys Thr Ile Ser Lys Ala Lys Gly Gln Pro Arg Glu Pro
    290                 295                 300

Gln Val Tyr Thr Leu Pro Pro Ser Arg Glu Glu Met Thr Lys Asn Gln
305                 310                 315                 320

Val Ser Leu Thr Cys Leu Val Lys Gly Phe Tyr Pro Ser Asp Ile Ala
                325                 330                 335

Val Glu Trp Glu Ser Asn Gly Gln Pro Glu Asn Asn Tyr Lys Thr Thr
            340                 345                 350

Pro Pro Val Leu Asp Ser Asp Gly Ser Phe Phe Leu Tyr Ser Lys Leu
        355                 360                 365
```

```
Thr Val Asp Lys Ser Arg Trp Gln Gln Gly Asn Val Phe Ser Cys Ser
    370                 375                 380

Val Met His Glu Ala Leu His Asn His Tyr Thr Gln Lys Ser Leu Ser
385                 390                 395                 400

Leu Ser Pro Gly Lys
                405

<210> SEQ ID NO 56
<211> LENGTH: 404
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 56

His Val Gln Lys Ser Asp Val Glu Met Glu Ala Gln Lys Asp Glu Ile
1               5                   10                  15

Ile Cys Pro Ser Cys Asn Arg Thr Ala His Pro Leu Arg His Ile Asn
                20                  25                  30

Asn Asp Met Ile Val Thr Asp Asn Asn Gly Ala Val Lys Phe Pro Gln
            35                  40                  45

Leu Cys Lys Phe Cys Asp Val Arg Phe Ser Thr Cys Asp Asn Gln Lys
    50                  55                  60

Ser Cys Met Ser Asn Cys Ser Ile Thr Ser Ile Cys Glu Lys Pro Gln
65                  70                  75                  80

Glu Val Cys Val Ala Val Trp Arg Lys Asn Asp Glu Asn Ile Thr Leu
                85                  90                  95

Glu Thr Val Cys His Asp Pro Lys Leu Pro Tyr His Asp Phe Ile Leu
            100                 105                 110

Glu Asp Ala Ala Ser Pro Lys Cys Ile Met Lys Glu Lys Lys Lys Pro
        115                 120                 125

Gly Glu Thr Phe Phe Met Cys Ser Cys Ser Ser Asp Glu Cys Asn Asp
130                 135                 140

Asn Ile Ile Phe Ser Glu Glu Tyr Asn Thr Ser Asn Pro Asp Thr Gly
145                 150                 155                 160

Gly Gly Gly Ser Gly Gly Gly Ser Gly Gly Gly Ser Gly Gly
                165                 170                 175

Gly Gly Ser Thr His Thr Cys Pro Pro Cys Pro Ala Pro Glu Leu Leu
            180                 185                 190

Gly Gly Pro Ser Val Phe Leu Phe Pro Pro Lys Pro Lys Asp Thr Leu
        195                 200                 205

Met Ile Ser Arg Thr Pro Glu Val Thr Cys Val Val Val Asp Val Ser
210                 215                 220

His Glu Asp Pro Glu Val Lys Phe Asn Trp Tyr Val Asp Gly Val Glu
225                 230                 235                 240

Val His Asn Ala Lys Thr Lys Pro Arg Glu Glu Gln Tyr Asn Ser Thr
                245                 250                 255

Tyr Arg Val Val Ser Val Leu Thr Val Leu His Gln Asp Trp Leu Asn
            260                 265                 270

Gly Lys Glu Tyr Lys Cys Lys Val Ser Asn Lys Ala Leu Pro Ala Pro
        275                 280                 285

Ile Glu Lys Thr Ile Ser Lys Ala Lys Gly Gln Pro Arg Glu Pro Gln
    290                 295                 300

Val Tyr Thr Leu Pro Pro Ser Arg Glu Glu Met Thr Lys Asn Gln Val
305                 310                 315                 320
```

```
Ser Leu Thr Cys Leu Val Lys Gly Phe Tyr Pro Ser Asp Ile Ala Val
                325                 330                 335

Glu Trp Glu Ser Asn Gly Gln Pro Glu Asn Asn Tyr Lys Thr Thr Pro
            340                 345                 350

Pro Val Leu Asp Ser Asp Gly Ser Phe Phe Leu Tyr Ser Lys Leu Thr
        355                 360                 365

Val Asp Lys Ser Arg Trp Gln Gln Gly Asn Val Phe Ser Cys Ser Val
    370                 375                 380

Met His Glu Ala Leu His Asn His Tyr Thr Gln Lys Ser Leu Ser Leu
385                 390                 395                 400

Ser Pro Gly Lys

<210> SEQ ID NO 57
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: See specification as filed for detailed
      description of substitutions and preferred embodiments

<400> SEQUENCE: 57

Gly Gly Gly Gly Ser Gly Gly Gly Gly Ser
1               5                   10

<210> SEQ ID NO 58
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: See specification as filed for detailed
      description of substitutions and preferred embodiments

<400> SEQUENCE: 58

Gly Gly Gly Gly Ser Gly Gly Gly Gly Ser Gly Gly Gly Gly Ser
1               5                   10                  15

<210> SEQ ID NO 59
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: See specification as filed for detailed
      description of substitutions and preferred embodiments

<400> SEQUENCE: 59

Gly Gly Gly Gly Ser Gly Gly Gly Gly Ser Gly Gly Gly Gly Ser Gly
1               5                   10                  15

Gly Gly Gly Ser
            20

<210> SEQ ID NO 60
<211> LENGTH: 25
<212> TYPE: PRT
<213> ORGANISM: Artificial Sequence
<220> FEATURE:
<223> OTHER INFORMATION: Description of Artificial Sequence: Synthetic
```

```
            peptide
<220> FEATURE:
<223> OTHER INFORMATION: See specification as filed for detailed
      description of substitutions and preferred embodiments

<400> SEQUENCE: 60

Gly Gly Gly Gly Ser Gly Gly Gly Ser Gly Gly Gly Gly Ser Gly
1               5                   10                  15

Gly Gly Gly Ser Gly Gly Gly Gly Ser
            20                  25

<210> SEQ ID NO 61
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 61

His His His His His His
1               5

<210> SEQ ID NO 62
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Asn Thr Ser Asn Pro Asp Thr Gly Gly Gly Thr His Thr Cys Pro Pro
1               5                   10                  15

Cys

<210> SEQ ID NO 63
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Asn Thr Ser Asn Pro Asp Thr Gly Gly Gly Gly Ser Gly Gly Gly Gly
1               5                   10                  15

Ser Thr His Thr Cys Pro Pro Cys
            20

<210> SEQ ID NO 64
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Asn Thr Ser Asn Pro Asp Thr Gly Gly Gly Gly Ser Gly Gly Gly Gly
1               5                   10                  15

Ser Gly Gly Gly Gly Ser Thr His Thr Cys Pro Pro Cys
            20                  25

<210> SEQ ID NO 65
```

```
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 65

Asn Thr Ser Asn Pro Asp Thr Gly Gly Gly Ser Gly Gly Gly Gly
1               5                   10                  15

Ser Gly Gly Gly Gly Ser Gly Gly Gly Gly Ser Thr His Thr Cys Pro
            20                  25                  30

Pro Cys

<210> SEQ ID NO 66
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Asn Thr Ser Asn Pro Asp Thr Gly Gly Gly Pro Lys Ser Cys Asp Lys
1               5                   10                  15

Thr His Thr Cys Pro Pro Cys
            20
```

TRANSFORMING GROWTH FACTOR BETA RECEPTOR TYPE II FUSION POLYPEPTIDES

CROSS-REFERENCE TO RELATED APPLICATIONS

This application claims the benefit of priority from U.S. Provisional Application No. 62/501,229, filed on May 4, 2017; from U.S. Provisional Application No. 62/510,422, filed on May 24, 2017; and from U.S. Provisional Application No. 62/578,674, filed on Oct. 30, 2017. The foregoing applications are incorporated herein by reference in their entirety.

SEQUENCE LISTING

The instant application contains a Sequence Listing which has been submitted electronically in ASCII format and is hereby incorporated by reference in its entirety. Said ASCII copy, created on Jun. 29, 2018, is named 1848179-0002-121-101_SL.txt and is 113,342 bytes in size.

BACKGROUND OF THE INVENTION

Members of the transforming growth factor-beta (TGFβ) superfamily are pleiotropic cytokines involved in essential cellular functions such as proliferation, differentiation, apoptosis, motility, extracellular matrix production, tissue remodeling, angiogenesis, immune response, cell adhesion, and also play a key role in pathophysiology of disease states as different as chronic inflammatory conditions and cancer. Members of the TGFβ superfamily have been classified into major family groupings, which include TGFβs, bone morphogenetic proteins (BMP), osteogenic proteins (OP), growth and differentiation factors (GDF), inhibins/activins, mullerian inhibitory substances (MIS) and glial derived neurotrophic factors (GDNF).

TGFβ superfamily members transduce their signals across the plasma membrane by inducing the formation of heteromeric complexes of specific type I and type II serine/threonine kinase receptors, which in turn activate a particular subset of SMAD proteins (some inhibitory and some excitatory). The SMAD molecule compounds relay the signals into the nucleus where they direct transcriptional responses in concert with other proteins.

Dysfunctional TGFβ superfamily signaling has been linked to several clinical disorders including cancer, fibrosis, bone diseases, diabetic nephropathy, as well as chronic vascular diseases such as atherosclerosis.

Thus, it is an object of the present disclosure to provide compositions and methods for modulating TGFβ superfamily signaling.

SUMMARY OF THE INVENTION

In part, the disclosure provides TβRII polypeptide fusion proteins and the use of such fusion proteins as selective antagonists for TGFβ1 or TGFβ3. As described herein, polypeptides comprising part or all of the TβRII extracellular domain (ECD), with or without additional mutations, bind to and/or inhibit TGFβ1 or TGFβ3 with varying affinities. In particular, TβRII polypeptides comprising a heterologous portion (e.g., an Fc immunoglobulin domain) and a linker of at least 10 amino acids in length (e.g., a linker having the amino acid sequence of SEQ ID NO: 6) are associated with surprisingly superior TGFβ1 and TGFβ3 binding properties as compared to TβRII polypeptides having a shorter linker. Thus, in certain aspects, the disclosure provides TβRII polypeptides for use in selectively inhibiting TGFβ superfamily associated disorders.

In some embodiments, the disclosure provides for a Transforming Growth Factor-β Receptor II (TβRII) fusion polypeptide comprising: a) an extracellular domain of a TβRII portion; b) a heterologous portion, and c) a linker portion; wherein the linker is at least 10 amino acids in length; and wherein the TβRII extracellular domain portion comprises an amino acid sequence at least 80% identical to: i) a sequence beginning at any of positions 23 to 35 of SEQ ID NO: 1 and ending at any of positions 153 to 159 of SEQ ID NO: 1 or ii) a sequence beginning at any of positions 23 to 60 of SEQ ID NO: 2 and ending at any of positions 178 to 184 of SEQ ID NO: 2. In some embodiments, the TβRII extracellular domain portion comprises an amino acid sequence at least 80% identical to a sequence beginning at any of positions 23 to 35 of SEQ ID NO: 1 and ending at any of positions 153 to 159 of SEQ ID NO: 1. In some embodiments, the TβRII extracellular domain portion comprises an amino acid sequence at least 90% identical to a sequence beginning at any of positions 23 to 35 of SEQ ID NO: 1 and ending at any of positions 153 to 159 of SEQ ID NO: 1. In some embodiments, the TβRII extracellular domain portion comprises an amino acid sequence at least 95% identical to a sequence beginning at any of positions 23 to 35 of SEQ ID NO: 1 and ending at any of positions 153 to 159 of SEQ ID NO: 1. In some embodiments, the TβRII extracellular domain portion comprises an amino acid sequence at least 97% identical to a sequence beginning at any of positions 23 to 35 of SEQ ID NO: 1 and ending at any of positions 153 to 159 of SEQ ID NO: 1. In some embodiments, the TβRII extracellular domain portion comprises an amino acid sequence beginning at any of positions 23 to 35 of SEQ ID NO: 1 and ending at any of positions 153 to 159 of SEQ ID NO: 1. In some embodiments, the TβRII extracellular domain portion comprises an amino acid sequence at least 80% identical to a sequence beginning at any of positions 23 to 60 of SEQ ID NO: 2 and ending at any of positions 178 to 184 of SEQ ID NO: 2. In some embodiments, the TβRII extracellular domain portion comprises an amino acid sequence at least 90% identical to a sequence beginning at any of positions 23 to 60 of SEQ ID NO: 2 and ending at any of positions 178 to 184 of SEQ ID NO: 2. In some embodiments, the TβRII extracellular domain portion comprises an amino acid sequence at least 95% identical to a sequence beginning at any of positions 23 to 60 of SEQ ID NO: 2 and ending at any of positions 178 to 184 of SEQ ID NO: 2. In some embodiments, the TβRII extracellular domain portion comprises an amino acid sequence at least 97% identical to a sequence beginning at any of positions 23 to 60 of SEQ ID NO: 2 and ending at any of positions 178 to 184 of SEQ ID NO: 2. In some embodiments, the TβRII extracellular domain portion comprises an amino acid sequence beginning at any of positions 23 to 60 of SEQ ID NO: 2 and ending at any of positions 178 to 184 of SEQ ID NO: 2. In some embodiments, the TβRII extracellular domain portion comprises an amino acid sequence at least 80% identical to SEQ ID NO: 18. In some embodiments, the TβRII extracellular domain portion comprises an amino acid sequence at least 90% identical to SEQ ID NO: 18. In some embodiments, the TβRII extracellular domain portion comprises an amino acid sequence at least 95% identical to SEQ ID NO: 18. In some embodiments, the TβRII extracellular domain portion comprises an amino acid sequence at least 97% identical to SEQ ID NO: 18. In some embodiments, the TβRII extracellular domain portion comprises the amino acid sequence of SEQ ID NO: 18. In some embodiments, the TβRII extracellular domain portion consists of an amino acid sequence at least 80% identical to a sequence beginning at any of positions 23 to 35 of SEQ ID NO: 1 and ending at any of positions 153 to 159 of SEQ ID NO: 1. In some embodiments, the TβRII extracellular domain portion consists of an amino acid sequence at least 90% identical to a sequence beginning at any of positions 23 to 35 of SEQ ID NO: 1 and ending at any of positions 153 to 159 of SEQ ID NO: 1. In some embodiments, the TβRII extracellular domain portion consists of an amino acid sequence at least 95% identical to a sequence beginning at any of positions 23 to 35 of SEQ ID NO: 1 and ending at any of positions 153 to 159 of SEQ ID NO: 1. In some embodiments, the TβRII extracellular domain portion consists of an amino acid sequence at least 97% identical to a sequence beginning at any of positions 23 to 35 of SEQ ID NO: 1 and ending at any of positions 153 to 159 of SEQ ID NO: 1. In some embodiments, the TβRII extracellular domain portion consists of an amino acid sequence beginning at any of positions 23 to 35 of SEQ ID NO: 1 and ending at any of positions 153 to 159 of SEQ ID NO: 1. In some embodiments, the TβRII extracellular domain portion consists of an amino acid sequence at least 80% identical to a sequence beginning at any of positions 23 to 60 of SEQ ID NO: 2 and ending at any of positions 178 to 184 of SEQ ID NO: 2. In some embodiments, the TβRII extracellular domain portion consists of an amino acid sequence at least 90% identical to a sequence beginning at any of positions 23 to 60 of SEQ ID NO: 2 and ending at any of positions 178 to 184 of SEQ ID NO: 2. In some embodiments, the TβRII extracellular domain portion consists of an amino acid sequence at least 95% identical to a sequence beginning at any of positions 23 to 60 of SEQ ID NO: 2 and ending at any of positions 178 to 184 of SEQ ID NO: 2. In some embodiments, the TβRII extracellular domain portion consists of an amino acid sequence at least 97% identical to a sequence beginning at any of positions 23 to 60 of SEQ ID NO: 2 and ending at any of positions 178 to 184 of SEQ ID NO: 2. In some embodiments, the TβRII extracellular domain portion consists of an amino acid sequence beginning at any of positions 23 to 60 of SEQ ID NO: 2 and ending at any of positions 178 to 184 of SEQ ID NO: 2. In some embodiments, the TβRII extracellular domain portion consists of an amino acid sequence at least 80% identical to SEQ ID NO: 18. In some embodiments, the TβRII extracellular domain portion consists of an amino acid sequence at least 90% identical to SEQ ID NO: 18. In some embodiments, the TβRII extracellular domain portion consists of an amino acid sequence at least 95% identical to SEQ ID NO: 18. In some embodiments, the TβRII extracellular domain portion consists of an amino acid sequence at least 97% identical to SEQ ID NO: 18. In some embodiments, the TβRII extracellular domain portion consists of the amino acid sequence of SEQ ID NO: 18. In some embodiments, the polypeptide comprises an N-terminal leader sequence. In some embodiments, the N-terminal leader sequence comprises the amino acid sequence of any one of SEQ ID NOs: 22-24. In some embodiments, the N-terminal leader sequence comprises the amino acid sequence of SEQ ID NO: 23. In some embodiments, the heterologous portion is an immunoglobulin Fc domain. In some embodiments, the immunoglobulin Fc domain is a human immunoglobulin Fc domain. In some embodiments, the heterologous portion comprises an amino acid sequence that is at least 80% identical to SEQ ID NO: 20. In some embodiments, the heterologous portion comprises an amino acid sequence that is at least 90% identical to SEQ ID NO: 20. In some embodiments, the linker is less than 25 amino acids in length. In some embodiments, the linker is between 10 and 25 amino acids in length. In some embodiments, the linker is between 15 and 25 amino acids in length. In some embodiments, the linker is between 17 and 22 amino acids in length. In some embodiments, the linker is 21 amino acids in length. In some embodiments, the heterologous portion comprises an amino acid sequence that is at least 95% identical to SEQ ID NO: 20. In some embodiments, the heterologous portion comprises an amino acid sequence that is at least 97% identical to SEQ ID NO: 20. In some embodiments, the heterologous portion comprises the amino acid sequence of SEQ ID NO: 20. In some embodiments, the linker comprises (GGGGS)n, wherein n=≥2 (SEQ ID NO: 57). In some embodiments, the linker comprises (GGGGS)n, wherein n=≥3 (SEQ ID NO: 58). In some embodiments, the linker comprises (GGGGS)n, wherein n=≥4 (SEQ ID NO: 59). In some embodiments, the linker comprises (GGGGS)$_n$, wherein n≠≥5 (SEQ ID NO: 60). In some embodiments, the linker comprises the amino acid sequence of SEQ ID NO: 21. In some embodiments, the linker comprises the amino acid sequence of any one of SEQ ID NOs: 4-7. In some embodiments, the linker comprises the amino acid sequence of SEQ ID NO: 6. In some embodiments, the polypeptide comprises an amino acid sequence that is at least 80% identical to the amino acid sequence of SEQ ID NO: 11. In some embodiments, the polypeptide comprises an amino acid sequence that is at least 90% identical to the amino acid sequence of SEQ ID NO: 11. In some embodiments, the polypeptide comprises an amino acid sequence that is at least 95% identical to the amino acid sequence of SEQ ID NO: 11. In some embodiments, the polypeptide comprises the amino acid sequence of SEQ ID NO: 11. In some embodiments, the polypeptide comprises an amino acid sequence that is at least 80% identical to the amino acid sequence of SEQ ID NO: 13. In some embodiments, the polypeptide comprises an amino acid sequence that is at least 90% identical to the amino acid sequence of SEQ ID NO: 13. In some embodiments, the polypeptide comprises an amino acid sequence that is at least 95% identical to the amino acid sequence of SEQ ID NO: 13. In some embodiments, the polypeptide comprises the amino acid sequence of SEQ ID NO: 13. In some embodiments, the polypeptide comprises an amino acid sequence that is at least 80% identical to the amino acid sequence of SEQ ID NO: 50. In some embodiments, the polypeptide comprises an amino acid sequence that is at least 90% identical to the amino acid sequence of SEQ ID NO: 50. In some embodiments, the polypeptide comprises an amino acid sequence that is at least 95% identical to the amino acid sequence of SEQ ID NO: 50. In some embodiments, the polypeptide comprises the amino acid sequence of SEQ ID NO: 50. In some embodiments, the polypeptide comprises an amino acid sequence that is at least 80% identical to the amino acid sequence of SEQ ID NO: 51. In some embodiments, the polypeptide comprises an amino acid sequence that is at least 90% identical to the amino acid sequence of SEQ ID NO: 51. In some embodiments, the polypeptide comprises an amino acid sequence that is at least 95% identical to the amino acid sequence of SEQ ID NO: 51. In some embodiments, the polypeptide comprises the amino acid sequence of SEQ ID NO: 51. In some embodiments, the polypeptide comprises an amino acid sequence that is at least 80% identical to the amino acid sequence of SEQ ID NO: 53. In some embodiments, the polypeptide comprises an amino acid sequence that is at least 90% identical to the amino acid sequence of SEQ ID NO: 53. In some embodiments, the polypeptide comprises an amino acid sequence that is at least 95% identical to the amino acid sequence of SEQ ID NO: 53. In some embodiments, the polypeptide comprises the amino acid sequence of SEQ ID NO: 53. In some embodiments, the polypeptide comprises an amino acid sequence that is at least 80% identical to the amino acid sequence of SEQ ID NO: 56. In some embodiments, the polypeptide comprises an amino acid sequence that is at least 90% identical to the amino acid sequence of SEQ ID NO: 56. In some embodiments, the polypeptide comprises an amino acid sequence that is at least 95% identical to the amino acid sequence of SEQ ID NO: 56. In some embodiments, the polypeptide comprises the amino acid sequence of SEQ ID NO: 56. In some embodiments, the polypeptide comprises an amino acid sequence that is at least 80% identical to the amino acid sequence of SEQ ID NO: 15. In some embodiments, the polypeptide comprises an amino acid sequence that is at least 90% identical to the amino acid sequence of SEQ ID NO: 15. In some embodiments, the polypeptide comprises an amino acid sequence that is at least 95% identical to the amino acid sequence of SEQ ID NO: 15. In some embodiments, the polypeptide comprises the amino acid sequence of SEQ ID NO: 15. In some embodiments, the TβRII polypeptide does not include amino acids 185-592 of SEQ ID NO: 2. In some embodiments, the TβRII polypeptide does not include amino acids 1-22 of SEQ ID NO: 2. In some embodiments, the polypeptide consists of or consists essentially of: a) a TβRII polypeptide portion comprising an amino acid sequence that is at least 85%, 90%, 95%, 97%, or 99% identical to the amino acid sequence of SEQ ID NO: 18 and no more than 10, 9, 8, 7, 6, 5, 4, 3, 2 or 1 additional amino acids; b) a linker portion comprising an amino acid sequence that is at least 85%, 90%, 95%, 97%, or 99% identical to the amino acid sequence of SEQ ID NO: 6 and no more than 5, 4, 3, 2 or 1 additional amino acids; c) a heterologous portion comprising an amino acid sequence that is at least 85%, 90%, 95%, 97%, or 99% identical to the amino acid sequence of SEQ ID NO: 20 and no more than 25, 20, 15, 10, 5, 4, 3, 2, or 1 additional amino acids; and d) optionally a leader sequence (e.g., SEQ ID NO: 23). In some embodiments, the polypeptide consists of or consists essentially of: a) a TβRII polypeptide portion comprising the amino acid sequence of SEQ ID NO: 18 and no more than 10, 9, 8, 7, 6, 5, 4, 3, 2 or 1 additional amino acids; b) a linker portion comprising the amino acid sequence of SEQ ID NO: 6 and no more than 5, 4, 3, 2 or 1 additional amino acids; c) a heterologous portion comprising the amino acid sequence of SEQ ID NO: 20 and no more than 25, 20, 15, 10, 5, 4, 3, 2, or 1 additional amino acids; and d) optionally a leader sequence (e.g., SEQ ID NO: 23). In some embodiments, the polypeptide comprises: a) an extracellular domain of a TβRII portion; wherein the extracellular domain comprises an amino acid sequence that is at least 85%, 90%, 95%, 97%, or 99% identical to the sequence of SEQ ID NO: 18; b) a heterologous portion, wherein the heterologous portion comprises an amino acid sequence that is at least 85%, 90%, 95%, 97%, or 99% identical to the sequence of SEQ ID NO: 20; and c) a linker portion connecting the extracellular domain and the heterologous portion; wherein the linker comprises an amino acid sequence that is at least 85%, 90%, 95%, 97%, or 99% identical to the amino acid sequence of SEQ ID NO: 6. In some embodiments, the polypeptide comprises: a) an extracellular domain of a TβRII portion; wherein the extracellular domain comprises the amino acid sequence of SEQ ID NO: 18; b) a heterologous portion, wherein the heterologous portion comprises the amino acid sequence of SEQ ID NO: 20; and c) a linker portion connecting the extracellular domain and the heterologous portion; wherein the linker comprises the amino acid sequence of SEQ ID NO: 6. In some embodiments, the polypeptide comprises an amino acid sequence that is at least 85%, 90%, 95%, 97%, or 99% identical to the amino acid sequence of SEQ ID NO: 48. In some embodiments, the polypeptide comprises the amino acid sequence of SEQ ID NO: 48. In some embodiments, the polypeptide does not include a leader sequence, or wherein the leader sequence has been removed. In some embodiments, the polypeptide includes one or more modified amino acid residues selected from: a glycosylated amino acid, a PEGylated amino acid, a farnesylated amino acid, an acetylated amino acid, a biotinylated amino acid, an amino acid conjugated to a lipid moiety, and an amino acid conjugated to an organic derivatizing agent. In some embodiments, the polypeptide is glycosylated. In some embodiments, the polypeptide has a glycosylation pattern characteristic of expression of the polypeptide in CHO cells. In some embodiments, the polypeptide binds human TGFβ1 with an equilibrium dissociation constant (KD) less than 100 pM. In some embodiments, the polypeptide binds human TGFβ1 with an equilibrium dissociation constant (KD) less than 75 pM. In some embodiments, the polypeptide binds human TGFβ3 with an equilibrium dissociation constant (KD) less than 60 pM. In some embodiments, the polypeptide binds human TGFβ3 with an equilibrium dissociation constant (KD) less than 50 pM. In some embodiments, the polypeptide inhibits TGFβ1 with an IC50 of less than 1.0 nM, as determined using a reporter gene assay. In some embodiments, the polypeptide inhibits TGFβ1 with an IC50 of less than 0.25 nM, as determined using a reporter gene assay. In some embodiments, the polypeptide inhibits TGFβ1 with an IC50 of less than 0.1 nM, as determined using a reporter gene assay. In some embodiments, the polypeptide inhibits TGFβ1 with an IC50 of less than 0.05 nM, as determined using a reporter gene assay. In some embodiments, the polypeptide inhibits TGFβ3 with an IC50 of less than 0.3 nM, as determined using a reporter gene assay. In some embodiments, the polypeptide inhibits TGFβ3 with an IC50 of less than 0.1 nM, as determined using a reporter gene assay. In some embodiments, the polypeptide inhibits TGFβ3 with an IC50 of less than 0.05 nM, as determined using a reporter gene assay. In some embodiments, the polypeptide inhibits TGFβ3 with an IC50 of less than 0.04 nM, as determined using a reporter gene assay. In some embodiments, the reporter gene assay is a CAGA reporter assay.

In some embodiments, the disclosure provides for a homodimer comprising any two of the polypeptides disclosed herein.

In some embodiments, the disclosure provides for an isolated polynucleotide comprising a coding sequence for any of the polypeptides disclosed herein. In some embodiments, the disclosure provides for a recombinant polynucleotide comprising a promoter sequence operably linked to any of the polynucleotides disclosed herein. In some embodiments, the polynucleotide comprises a nucleotide sequence that is at least 80%, 85%, 90%, 95%, 97% or 100% identical to any one of SEQ ID NOs: 10, 12 or 14.

In some embodiments, the disclosure provides for a cell transformed with any of the polynucleotides disclosed herein. In some embodiments, cell is a mammalian cell. In some embodiments, the cell is a CHO cell or a human cell.

In some embodiments, the disclosure provides for a pharmaceutical preparation comprising pharmaceutically acceptable excipient and any of the polypeptides disclosed herein or any of the homodimers disclosed herein.

In some embodiments, the disclosure provides for a method of modulating the response of a cell to a TGFβ superfamily member, the method comprising exposing the cell to any of the polypeptides disclosed herein or any of the homodimers disclosed herein. In some embodiments, the disclosure provides for a method of treating a disease or condition associated with a TGFβ superfamily member in a patient in need thereof, the method comprising administering to the patient an effective amount of any of the polypeptides disclosed herein or any of the homodimers disclosed herein. In some embodiments, the TGFβ superfamily member is TGFβ1 or TGFβ3. In some embodiments, the disease or condition is a cancer. In some embodiments, the cancer is selected from stomach cancer, intestinal cancer, skin cancer, breast cancer, melanoma, bone cancer and thyroid cancer. In some embodiments, the disease or condition is a fibrotic or sclerotic disease or condition. In some embodiments, the fibrotic or sclerotic disease or condition is selected from scleroderma, lupus erythematosis, pulmonary fibrosis, atherosclerosis, liver fibrosis, diffuse systemic sclerosis, glomerulonephritis, neural scarring, dermal scarring, radiation-induced fibrosis, hepatic fibrosis, idiopathic pulmonary fibrosis and myelofibrosis. In some embodiments, the disease or condition is myelofibrosis. In some embodiments, the disease or condition is selected from the group consisting of primary myelofibrosis, post-polycythemia vera myelofibrosis, and post-essential thrombocythemia myelofibrosis. In some embodiments, the disease or condition is selected from the group consisting of low risk, intermediate-1 risk, intermediate-2 risk, or high-risk myelofibrosis according to the International Prognostic Scoring System (IPSS) or to the to the dynamic IPSS (DIPSS). In some embodiments, the disease or condition is heart disease. In some embodiments, the disease or condition is selected from hereditary hemorrhagic telangiectasia (HHT), Marfan syndrome, Loeys-Dietz syndrome, familial thoracic aortic aneurysm syndrome, arterial tortuosity syndrome, pre-eclampsia, atherosclerosis, restenosis, and hypertrophic cardiomyopathy/congestive heart failure. In some embodiments, the disease or condition is pulmonary hypertension. In some embodiments, the pulmonary hypertension is Class I, Class II, Class III, or Class IV pulmonary hypertension as recognized by the World Health Organization. In some embodiments, the disease or condition is a kidney-associated disease or condition. In some embodiments, the kidney-associated disease or condition is selected from the group consisting of: chronic kidney diseases (or failure), acute kidney diseases (or failure), primary kidney diseases, non-diabetic kidney diseases, glomerulonephritis, interstitial nephritis, diabetic kidney diseases, diabetic nephropathy, glomerulosclerosis, rapid progressive glomerulonephritis, renal fibrosis, Alport syndrome, IDDM nephritis, mesangial proliferative glomerulonephritis, membranoproliferative glomerulonephritis, crescentic glomerulonephritis, renal interstitial fibrosis, focal segmental glomerulosclerosis, membranous nephropathy, minimal change disease, pauci-immune rapid progressive glomerulonephritis, IgA nephropathy, polycystic kidney disease, Dent's disease, nephrocytinosis, Heymann nephritis, autosomal dominant (adult) polycystic kidney disease, autosomal recessive (childhood) polycystic kidney disease, acute kidney injury, nephrotic syndrome, renal ischemia, podocyte diseases or disorders, proteinuria, glomerular diseases, membranous glomerulonephritis, focal segmental glomerulonephritis, pre-eclampsia, eclampsia, kidney lesions, collagen vascular diseases, benign orthostatic (postural) proteinuria, IgM nephropathy, membranous nephropathy, sarcoidosis, diabetes mellitus, kidney damage due to drugs, Fabry's disease, aminoaciduria, Fanconi syndrome, hypertensive nephrosclerosis, interstitial nephritis, Sickle cell disease, hemoglobinuria, myoglobinuria, Wegener's Granulomatosis, Glycogen Storage Disease Type 1, chronic kidney disease, chronic renal failure, low Glomerular Filtration Rate (GFR), nephroangiosclerosis, lupus nephritis, ANCA-positive pauci-immune crescentic glomerulonephritis, chronic allograft nephropathy, nephrotoxicity, renal toxicity, kidney necrosis, kidney damage, glomerular and tubular injury, kidney dysfunction, nephritic syndrome, acute renal failure, chronic renal failure, proximal tubal dysfunction, acute kidney transplant rejection, chronic kidney transplant rejection, non-IgA mesangioproliferative glomerulonephritis, postinfectious glomerulonephritis, vasculitides with renal involvement of any kind, any hereditary renal disease, any interstitial nephritis, renal transplant failure, kidney cancer, kidney disease associated with other conditions (e.g., hypertension, diabetes, and autoimmune disease), Dent's disease, nephrocytinosis, Heymann nephritis, a primary kidney disease, a collapsing glomerulopathy, a dense deposit disease, a cryoglobulinemia-associated glomerulonephritis, an Henoch-Schonlein disease, a postinfectious glomerulonephritis, a bacterial endocarditis, a microscopic polyangitis, a Churg-Strauss syndrome, an anti-GBM-antibody mediated glomerulonephritis, amyloidosis, a monoclonal immunoglobulin deposition disease, a fibrillary glomerulonephritis, an immunotactoid glomerulopathy, ischemic tubular injury, a medication-induced tubulo-interstitial nephritis, a toxic tubulo-interstitial nephritis, an infectious tubulo-interstitial nephritis, a bacterial pyelonephritis, a viral infectious tubulo-interstitial nephritis which results from a polyomavirus infection or an HIV infection, a metabolic-induced tubulo-interstitial disease, a mixed connective disease, a cast nephropathy, a crystal nephropathy which may results from urate or oxalate or drug-induced crystal deposition, an acute cellular tubulo-interstitial allograft rejection, a tumoral infiltrative disease which results from a lymphoma or a post-transplant lymphoproliferative disease, an obstructive disease of the kidney, vascular disease, a thrombotic microangiopathy, a nephroangiosclerosis, an atheroembolic disease, a mixed connective tissue disease, a polyarteritis nodosa, a calcineurin-inhibitor induced-vascular disease, an acute cellular vascular allograft rejection, an acute humoral allograft rejection, early renal function decline (ERFD), end stage renal disease (ESRD), renal vein thrombosis, acute tubular necrosis, acute interstitial nephritis, established chronic kidney disease, renal artery stenosis, ischemic nephropathy, uremia, drug and toxin-induced chronic tubulointerstitial nephritis, reflux nephropathy, kidney stones, Goodpasture's syndrome, normocytic normochromic anemia, renal anemia, diabetic chronic kidney disease, IgG4-related disease, von Hippel-Lindau syndrome, tuberous sclerosis, nephronophthisis, medullary cystic kidney disease, renal cell carcinoma, adenocarcinoma, nephroblastoma, lymphoma, leukemia, hyposialylation disorder, chronic cyclosporine nephropathy, renal reperfusion injury, renal dysplasia, azotemia, bilateral arterial occlusion, acute uric acid nephropathy, hypovolemia, acute bilateral obstructive uropathy, hypercalcemic nephropathy, hemolytic uremic syndrome, acute urinary retention, malignant nephrosclerosis, postpartum glomerulosclerosis, scleroderma, non-Goodpasture's anti-GBM disease, microscopic polyarteritis nodosa, allergic granulomatosis, acute radiation nephritis, post-streptococcal glomerulonephritis, Waldenstrom's macroglobulinemia, analgesic nephropathy, arteriovenous fistula, arteriovenous graft, dialysis, ectopic kidney, medullary sponge kidney, renal osteodystrophy, solitary kidney, hydronephrosis, microalbuminuria, uremia, haematuria, hyperlipidemia, hypoalbuminaemia, lipiduria, acidosis, hyperkalemia, and edema. In some embodiments, the kidney-associated disease or condition is chronic kidney disease.

BRIEF DESCRIPTION OF THE DRAWINGS

The patent or patent application file contains at least one drawing executed in color. Copies of this patent or patent application publication with color drawing(s) will be provided by the Office upon request and payment of the necessary fee.

FIG. 1 shows the amino acid sequence of native precursor for the B (short) isoform of human TGFβ receptor type II (hTβRII) (NP_003233.4). Solid underline indicates the mature extracellular domain (ECD) (residues 23-159), and double underline indicates valine that is replaced in the A (long) isoform. Dotted underline denotes leader (residues 1-22).

FIG. 2 shows the amino acid sequence of native precursor for the A (long) isoform of human TβRII (NP_001020018.1). Solid underline indicates the mature ECD (residues 23-184), and double underline indicates the splice-generated isoleucine substitution. Dotted underline denotes leader (residues 1-22).

FIGS. 4A and 4B show in tabular form the binding affinity between TGFβ1 and TGFβ3 and one of several different TβRII-Fc fusion protein constructs.

FIGS. 5E and 5F provide IC50 data from these same experiments in tabular form.

DETAILED DESCRIPTION OF THE INVENTION

1. Overview

Figure 3:
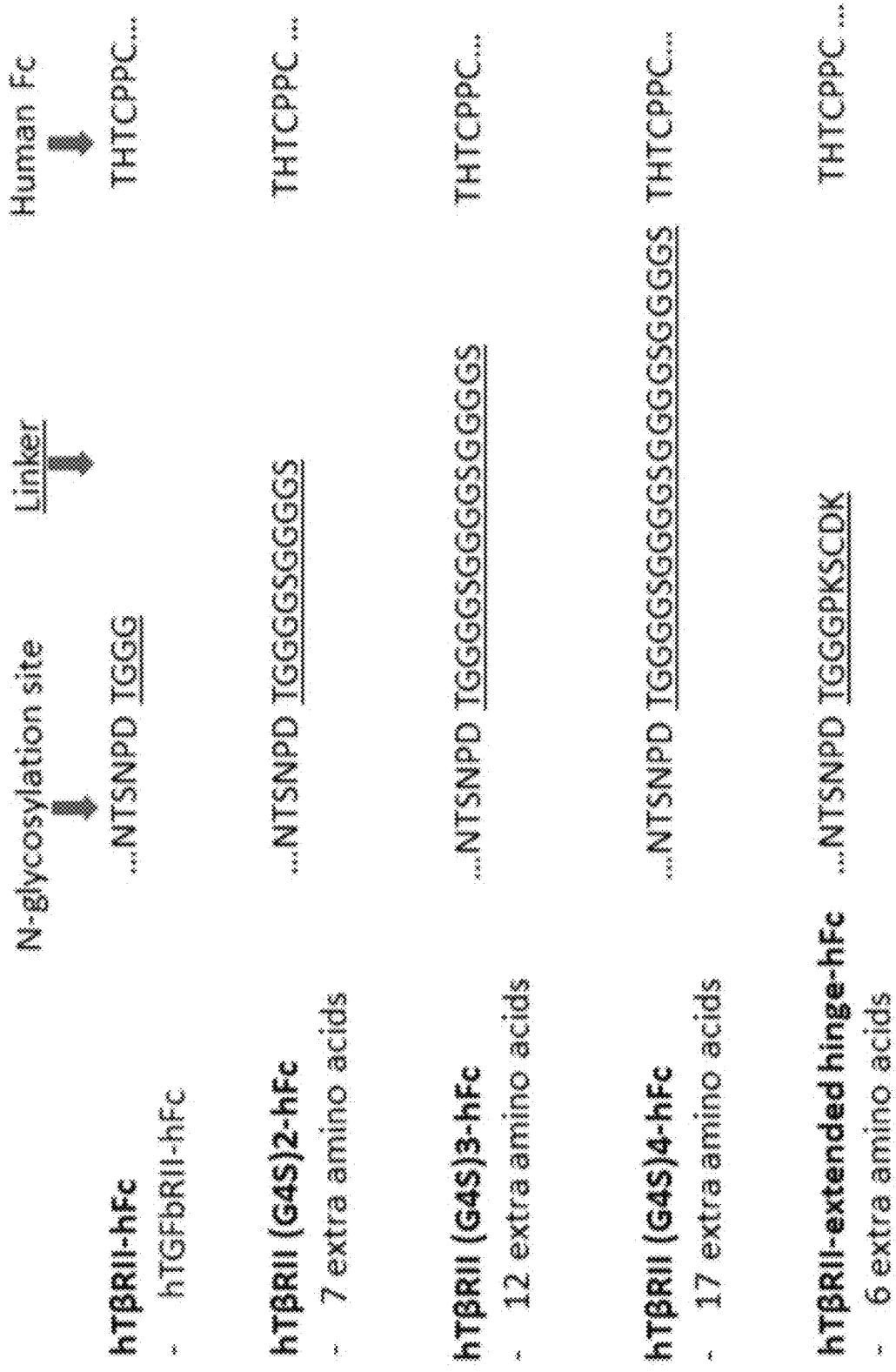
FIG. 3 shows a comparison of the linker sequences of five different TβRII constructs (SEQ ID NOS 62-66, respectively, in order of appearance).

Proteins described herein are the human forms, unless otherwise specified. NCBI references for the proteins are as follows: human TβRII isoform A (hTβRII$_{long}$), NP_001020018.1 and human TβRII isoform B (hTβRII$_{short}$), (NP_003233.4). Sequences of native TβRII proteins from human are set forth in FIGS. 1 and 2. In some embodiments, the TβRII proteins are from non-human animals, such as a mouse, rat, cow or monkey.

The TGFβ superfamily contains a variety of growth factors that share common sequence elements and structural motifs. These proteins are known to exert biological effects on a large variety of cell types in both vertebrates and invertebrates. Members of the superfamily perform important functions during embryonic development in pattern formation and tissue specification and can influence a variety of differentiation processes, including adipogenesis, myogenesis, chondrogenesis, cardiogenesis, hematopoiesis, neurogenesis, and epithelial cell differentiation. By manipulating the activity of a member of the TGFβ family, it is often possible to cause significant physiological changes in an organism. For example, the Piedmontese and Belgian Blue cattle breeds carry a loss-of-function mutation in the GDF8 (also called myostatin) gene that causes a marked increase in muscle mass. Grobet et al., Nat Genet. 1997, 17(1):71-4. Similarly, in humans, inactive alleles of GDF8 are associated with increased muscle mass and, reportedly, exceptional strength. Schuelke et al., N Engl J Med 2004, 350: 2682-8.

TGFβ signals are mediated by heteromeric complexes of type I (e.g. TβRI) and type II (e.g. TβRII) serine/threonine kinase receptors, which phosphorylate and activate downstream SMAD proteins upon ligand stimulation (Massagué, 2000, Nat. Rev. Mol. Cell Biol. 1:169-178). These type I and type II receptors are transmembrane proteins, composed of a ligand-binding extracellular domain with cysteine-rich region, a transmembrane domain, and a cytoplasmic domain with predicted serine/threonine specificity. Type I receptors are essential for signaling; and type II receptors are required for binding ligands and for expression of type I receptors. Type I and II receptors form a stable complex after ligand binding, resulting in phosphorylation of type I receptors by type II receptors. TGFβ has three mammalian isoforms, TGFβ1, TGFβ2 and TGFβ3, each with distinct functions in vivo. The binding of TGFβs to TβRII is a crucial step in initiating activation of the TGFβ signaling pathway, leading to phosphorylation of SMAD2, and translocation of the activated SMAD2/SMAD4 complex to the nucleus to modulate gene expression.

Thus, in certain aspects, the disclosure provides TβRII polypeptides as antagonists of TGFβ1 or TGFβ3 for use in treating various TGFβ1- or TGFβ3-associated disorders. While not wishing to be bound to any particular mechanism of action, it is expected that such polypeptides act by binding to TGFβ1 or TGFβ3 and inhibiting the ability of these ligands to form ternary signaling complexes.

The disclosure provides for fusion proteins comprising TβRII polypeptides and a heterologous portion (e.g., an Fc portion). In particular embodiments, the TβRII portion and the heterologous portion are fused by means of a linker. As described in greater detail below, the disclosure demonstrates that TβRII-Fc fusion proteins comprising linkers of certain lengths (e.g., a linker having 21 amino acids) were surprisingly able to bind TGFβ-1 and TGFβ-3 with stronger affinity than TβRII-Fc fusion proteins having a linker of only four amino acids.

The terms used in this specification generally have their ordinary meanings in the art, within the context of this invention and in the specific context where each term is used. Certain terms are discussed below or elsewhere in the specification, to provide additional guidance to the practitioner in describing the compositions and methods of the invention and how to make and use them. The scope or meaning of any use of a term will be apparent from the specific context in which the term is used.

"Homologous," in all its grammatical forms and spelling variations, refers to the relationship between two proteins that possess a "common evolutionary origin," including proteins from superfamilies in the same species of organism, as well as homologous proteins from different species of organism. Such proteins (and their encoding nucleic acids) have sequence homology, as reflected by their sequence similarity, whether in terms of percent identity or by the presence of specific residues or motifs and conserved positions. The term "sequence similarity," in all its grammatical forms, refers to the degree of identity or correspondence between nucleic acid or amino acid sequences that may or may not share a common evolutionary origin. However, in common usage and in the instant application, the term "homologous," when modified with an adverb such as "highly," may refer to sequence similarity and may or may not relate to a common evolutionary origin.

"Percent (%) sequence identity" or "percent (%) identical" with respect to a reference polypeptide (or nucleotide) sequence is defined as the percentage of amino acid residues (or nucleic acids) in a candidate sequence that are identical to the amino acid residues (or nucleic acids) in the reference polypeptide (nucleotide) sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared. For purposes herein, however, % amino acid (nucleic acid) sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, Calif., or may be compiled from the source code. The ALIGN-2 program should be compiled for use on a UNIX operating system, including digital UNIX V4.0D. All sequence comparison parameters are set by the ALIGN-2 program and do not vary.

"Agonize", in all its grammatical forms, refers to the process of activating a protein and/or gene (e.g., by activating or amplifying that protein's gene expression or by inducing an inactive protein to enter an active state) or increasing a protein's and/or gene's activity.

"Antagonize", in all its grammatical forms, refers to the process of inhibiting a protein and/or gene (e.g., by inhibiting or decreasing that protein's gene expression or by inducing an active protein to enter an inactive state) or decreasing a protein's and/or gene's activity.

The terms "about" and "approximately" as used in connection with a numerical value throughout the specification and the claims denotes an interval of accuracy, familiar and acceptable to a person skilled in the art.

Numeric ranges disclosed herein are inclusive of the numbers defining the ranges.

The terms "a" and "an" include plural referents unless the context in which the term is used clearly dictates otherwise. The terms "a" (or "an"), as well as the terms "one or more," and "at least one" can be used interchangeably herein. Furthermore, "and/or" where used herein is to be taken as specific disclosure of each of the two or more specified features or components with or without the other. Thus, the term "and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following aspects: A, B, and C; A, B, or C; A or C; A or B; B or C; A and C; A and B; B and C; A (alone); B (alone); and C (alone).

Throughout this specification, the word "comprise" or variations such as "comprises" or "comprising" will be understood to imply the inclusion of a stated integer or groups of integers but not the exclusion of any other integer or group of integers. As used herein, the term "comprises" also encompasses the use of the narrower terms "consisting" and "consisting essentially of."

The term "consisting essentially of" is limited to the specified materials or steps and those that do not materially affect the basic and novel characteristics of the invention(s) disclosed herein.

The term "appreciable affinity" as used herein means binding with a dissociation constant ($K_D$) of less than 50 nM.

The terms "polypeptide", "oligopeptide", "peptide" and "protein" are used interchangeably herein to refer to chains of amino acids of any length. The chain may be linear or branched, it may comprise modified amino acids, and/or may be interrupted by non-amino acids. The terms also encompass an amino acid chain that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art. It is understood that the polypeptides can occur as single chains or associated chains.

2. TβRII Polypeptides

Naturally occurring TβRII proteins are transmembrane proteins, with a portion of the protein positioned outside the cell (the extracellular portion) and a portion of the protein positioned inside the cell (the intracellular portion). Aspects of the present disclosure encompass variant TβRII polypeptides comprising mutations within the extracellular domain and/or truncated portions of the extracellular domain of TβRII. As described above, human TβRII occurs naturally in at least two isoforms—A (long) and B (short)—generated by alternative splicing in the extracellular domain (ECD) (FIGS. 1 and 2 and SEQ ID NOS: 1 and 2). SEQ ID NO: 27, which corresponds to residues 23-159 of SEQ ID NO: 1, depicts the native full-length extracellular domain of the short isoform of TβRII. SEQ ID NO: 18, which corresponds to residues 23-184 of SEQ ID NO: 2, depicts the native full-length extracellular domain of the long isoform of TβRII. Unless noted otherwise, amino acid position numbering with regard to variants based on the TβRII short and long isoforms refers to the corresponding position in the native precursors, SEQ ID NO: 1 and SEQ ID NO: 2, respectively.

In certain embodiments, the disclosure provides variant TβRII polypeptides. A TβRII polypeptide of the disclosure may bind to and inhibit the function of a TGFβ superfamily member, such as but not limited to, TGFβ1 or TGFβ3. TβRII polypeptides may include a polypeptide consisting of, or comprising, an amino acid sequence at least 80% identical, and optionally at least 85%, 90%, 95%, 96%, 97%, 98%, 99%, or 100% identical to a truncated ECD domain of a naturally occurring TβRII polypeptide, whose C-terminus occurs at any of amino acids 153-159 of SEQ ID NO: 1. TβRII polypeptides may include a polypeptide consisting of, or comprising, an amino acid sequence at least 80% identical, and optionally at least 85%, 90%, 95%, 96%, 97%, 98%, 99%, or 100% identical to a truncated ECD domain of a naturally occurring TβRII polypeptide, whose C-terminus occurs at any of amino acids 178-184 of SEQ ID NO: 2. In particular embodiments, the TβRII polypeptides comprise an amino acid sequence at least 80% identical, and optionally at least 85%, 90%, 95%, 96%, 97%, 98%, 99%, or 100% identical to the amino acid sequence of SEQ ID NO: 18. Optionally, a TβRII polypeptide does not include more than 5 consecutive amino acids, or more than 10, 20, 30, 40, 50, 52, 60, 70, 80, 90, 100, 150 or 200 or more consecutive amino acids from a sequence consisting of amino acids 160-567 of SEQ ID NO: 1 or from a sequence consisting of amino acids 185-592 of SEQ ID NO: 2. In some embodiments, the TβRII polypeptide does not include amino acids 160-567 of SEQ ID NO: 1. In some embodiments, the TβRII polypeptide does not include amino acids 1-22 of SEQ ID NO: 1. In some embodiments, the TβRII polypeptide does not include amino acids 1-22 and 160-567 of SEQ ID NO: 1. In some embodiments, the TβRII polypeptide does not include amino acids 185-592 of SEQ ID NO: 2. In some embodiments, the TβRII polypeptide does not include amino acids 1-22 of SEQ ID NO: 2. In some embodiments, the TβRII polypeptide does not include amino acids 1-22 and 185-592 of SEQ ID NO: 2. The unprocessed TβRII polypeptide may either include or exclude any signal sequence, as well as any sequence N-terminal to the signal sequence. As elaborated herein, the N-terminus of the mature (processed) TβRII polypeptide may occur at any of amino acids 23-35 of SEQ ID NO: 1 or 23-60 of SEQ ID NO: 2. Examples of mature TβRII polypeptides include, but are not limited to, amino acids 23-159 of SEQ ID NO: 1 (set forth in SEQ ID NO: 27), amino acids 29-159 of SEQ ID NO: 1 (set forth in SEQ ID NO: 28), amino acids 35-159 of SEQ ID NO: 1 (set forth in SEQ ID NO: 29), amino acids 23-153 of SEQ ID NO: 1 (set forth in SEQ ID NO: 30), amino acids 29-153 of SEQ ID NO: 1 (set forth in SEQ ID NO: 31), amino acids 35-153 of SEQ ID NO: 1 (set forth in SEQ ID NO: 32), amino acids 23-184 of SEQ ID NO: 2 (set forth in SEQ ID NO: 18), amino acids 29-184 of SEQ ID NO: 2 (set forth in SEQ ID NO: 33), amino acids 60-184 of SEQ ID NO: 2 (set forth in SEQ ID NO: 29), amino acids 23-178 of SEQ ID NO: 2 (set forth in SEQ ID NO: 34), amino acids 29-178 of SEQ ID NO: 2 (set forth in SEQ ID NO: 35), and amino acids 60-178 of SEQ ID NO: 2 (set forth in SEQ ID NO: 32). It will be understood by one of skill in the art that corresponding variants based on the long isoform of TβRII will include nucleotide sequences encoding the 25-amino acid insertion along with a conservative Val-Ile substitution at the flanking position C-terminal to the insertion. The TβRII polypeptides accordingly may include isolated extracellular portions of TβRII polypeptides, including both the short and the long isoforms, variants thereof (including variants that comprise, for example, no more than 2, 3, 4, 5, 10, 15, 20, 25, 30, or 35 amino acid substitutions in the sequence corresponding to amino acids 23-159 of SEQ ID NO: 1 or amino acids 23-184 of SEQ ID NO: 2), fragments thereof, and fusion proteins comprising any of the foregoing, but in each case preferably any of the foregoing TβRII polypeptides will retain substantial affinity for at least one of, or both of, TGFβ1 or TGFβ3. Generally, a TβRII polypeptide will be designed to be soluble in aqueous solutions at biologically relevant temperatures, pH levels, and osmolarity.

In some embodiments, the variant TβRII polypeptides of the disclosure comprise one or more mutations in the extracellular domain that confer an altered ligand binding profile. A TβRII polypeptide may include one, two, five or more alterations in the amino acid sequence relative to the corresponding portion of a naturally occurring TβRII polypeptide. In some embodiments, the mutation results in a substitution, insertion, or deletion at the position corresponding to position 70 of SEQ ID NO: 1. In some embodiments, the mutation results in a substitution, insertion, or deletion at the position corresponding to position 110 of SEQ ID NO: 1. Examples include, but are not limited to, an N to D substitution or a D to K substitution in the positions corresponding to positions 70 and 110, respectively, of SEQ ID NO: 1. Examples of such variant TβRII polypeptides include, but are not limited to, the sequences set forth in SEQ ID NOs: 36-39. A TβRII polypeptide may comprise a polypeptide or portion thereof that is encoded by any one of SEQ ID NOs: 10, 12, 14 or 16, or silent variants thereof or nucleic acids that hybridize to the complement thereof under stringent hybridization conditions. In particular embodiments, a TβRII polypeptide may comprise a polypeptide or portion thereof that is encoded by any one of SEQ ID NO: 12, or silent variants thereof or nucleic acids that hybridize to the complement thereof under stringent hybridization conditions.

In some embodiments, the variant TβRII polypeptides of the disclosure further comprise an insertion of 36 amino acids (SEQ ID NO: 41) between the pair of glutamate residues (positions 151 and 152 of SEQ ID NO: 1, or positions 176 and 177 of SEQ ID NO: 2) located near the C-terminus of the human TβRII ECD, as occurs naturally in the human TβRII isoform C (Konrad et al., BMC Genomics 8:318, 2007).

The disclosure further demonstrates that TβRII polypeptides can be modified to selectively antagonize TβRII ligands. The N70 residue represents a potential glycosylation site. In some embodiments, the TβRII polypeptides are aglycosylated. In some embodiments, the TβRII polypeptides are aglycosylated or have reduced glycosylation at position Asn157. In some embodiments, the TβRII polypeptides are aglycosylated or have reduced glycosylation at position Asn73.

In certain embodiments, a TβRII polypeptide binds to TGFβ1, and the TβRII polypeptide does not show substantial binding to TGFβ3. In certain embodiments, a TβRII polypeptide binds to TGFβ3, and the TβRII polypeptide does not show substantial binding to TGFβ1. Binding may be assessed using purified proteins in solution or in a surface plasmon resonance system, such as a Biacore™ system.

In certain embodiments, a TβRII polypeptide inhibits TGFβ1 cellular signaling, and the TβRII polypeptide has an intermediate or limited inhibitory effect on TGFβ3 signaling. In certain embodiments, a TβRII polypeptide inhibits TGFβ3 cellular signaling, and the TβRII polypeptide has an intermediate or limited inhibitory effect on TGFβ1 signaling. Inhibitory effect on cell signaling can be assayed by methods known in the art.

Taken together, an active portion of a TβRII polypeptide may comprise amino acid sequences 23-153, 23-154, 23-155, 23-156, 23-157, or 23-158 of SEQ ID NO: 1, as well as variants of these sequences starting at any of amino acids 24-35 of SEQ ID NO: 1. Similarly, an active portion of a TβRII polypeptide may comprise amino acid sequences 23-178, 23-179, 23-180, 23-181, 23-182, or 23-183 of SEQ ID NO: 2, as well as variants of these sequences starting at any of amino acids 24-60 of SEQ ID NO: 2. Exemplary TβRII polypeptides comprise amino acid sequences 29-159, 35-159, 23-153, 29-153 and 35-153 of SEQ ID NO: 1 or amino acid sequences 29-184, 60-184, 23-178, 29-178 and 60-178 of SEQ ID NO: 2. Variants within these ranges are also contemplated, particularly those having at least 80%, 85%, 90%, 95%, or 99% identity to the corresponding portion of SEQ ID NO: 1 or SEQ ID NO: 2. A TβRII polypeptide may be selected that does not include the sequence consisting of amino acids 160-567 of SEQ ID NO: 1 or amino acids 185-592 of SEQ ID NO: 2. In particular embodiments, the TβRII polypeptides comprise an amino acid sequence at least 80% identical, and optionally at least 85%, 90%, 95%, 96%, 97%, 98%, 99%, or 100% identical to the amino acid sequence of SEQ ID NO: 18.

As described above, the disclosure provides TβRII polypeptides sharing a specified degree of sequence identity or similarity to a naturally occurring TβRII polypeptide. To determine the percent identity of two amino acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). The amino acid residues at corresponding amino acid positions are then compared. When a position in the first sequence is occupied by the same amino acid residue as the corresponding position in the second sequence, then the molecules are identical at that position (as used herein amino acid "identity" is equivalent to amino acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity and similarity between two sequences can be accomplished using a mathematical algorithm (Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part 1, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991).

In one embodiment, the percent identity between two amino acid sequences is determined using the Needleman and Wunsch (J Mol. Biol. (48):444-453 (1970)) algorithm which has been incorporated into the GAP program in the GCG software package. In a specific embodiment, the following parameters are used in the GAP program: either a Blosum 62 matrix or a PAM250 matrix, and a gap weight of 16, 14, 12, 10, 8, 6, or 4 and a length weight of 1, 2, 3, 4, 5, or 6. In yet another embodiment, the percent identity between two nucleotide sequences is determined using the GAP program in the GCG software package (Devereux, J., et al., Nucleic Acids Res. 12(1):387 (1984)). Exemplary parameters include using a NWSgapdna.CMP matrix and a gap weight of 40, 50, 60, 70, or 80 and a length weight of 1, 2, 3, 4, 5, or 6. Unless otherwise specified, percent identity between two amino acid sequences is to be determined using the GAP program using a Blosum 62 matrix, a GAP weight of 10 and a length weight of 3, and if such algorithm cannot compute the desired percent identity, a suitable alternative disclosed herein should be selected.

In another embodiment, the percent identity between two amino acid sequences is determined using the algorithm of E. Myers and W. Miller (CABIOS, 4:11-17 (1989)) which has been incorporated into the ALIGN program (version 2.0), using a PAM120 weight residue table, a gap length penalty of 12 and a gap penalty of 4.

Another embodiment for determining the best overall alignment between two amino acid sequences can be determined using the FASTDB computer program based on the algorithm of Brutlag et al. (Comp. App. Biosci., 6:237-245 (1990)). In a sequence alignment the query and subject sequences are both amino acid sequences. The result of said global sequence alignment is presented in terms of percent identity. In one embodiment, amino acid sequence identity is performed using the FASTDB computer program based on the algorithm of Brutlag et al. (Comp. App. Biosci., 6:237-245 (1990)). In a specific embodiment, parameters employed to calculate percent identity and similarity of an amino acid alignment comprise: Matrix=PAM 150, k-tuple=2, Mismatch Penalty=1, Joining Penalty=20, Randomization Group Length=0, Cutoff Score=1, Gap Penalty=5 and Gap Size Penalty=0.05.

TβRII polypeptides may additionally include any of various leader sequences at the N-terminus. Such a sequence would allow the peptides to be expressed and targeted to the secretion pathway in a eukaryotic system. See, e.g., Ernst et al., U.S. Pat. No. 5,082,783 (1992). Alternatively, a native TβRII signal sequence may be used to effect extrusion from the cell. Possible leader sequences include native leaders, tissue plasminogen activator (TPA) and honeybee mellitin (SEQ ID NOs. 22-24, respectively). Examples of TβRII-Fc fusion proteins incorporating a TPA leader sequence include SEQ ID NOs: 11, 13, 15 and 17. Processing of signal peptides may vary depending on the leader sequence chosen, the cell type used and culture conditions, among other variables, and therefore actual N-terminal start sites for mature TβRII polypeptides may shift by 1, 2, 3, 4 or 5 amino acids in either the N-terminal or C-terminal direction. Examples of TβRII-Fc fusion proteins include SEQ ID NOs: 11, 13, 15 and 17. It will be understood by one of skill in the art that corresponding variants based on the long isoform of TβRII will include the 25-amino acid insertion along with a conservative Val-Ile substitution at the flanking position C-terminal to the insertion.

In some embodiments, any of the TβRII polypeptides disclosed herein are at least 80%, 85%, 90%, 92%, 94%, 95%, 97%, 99% or 100% identical to the amino acid sequence of any one of SEQ ID NOs: 18, 27, 30, 34, 36, 37, 38, 39, 48, 49 or 51, but lack one or more N-terminal amino acids as compared to the amino acid sequences of SEQ ID NO: 18, 27, 30, 34, 36, 37, 38, 39, 48, 49 or 51. In some embodiments, the TβRII polypeptide lacks the amino acid corresponding to the first amino acid (threonine) of any one of SEQ ID NOs: 18, 27, 30, 34, 36, 37, 38, 39, 48, 49 or 51. In some embodiments, the TβRII polypeptide lacks the amino acids corresponding to the first and second amino acids (threonine and isoleucine, respectively) of any one of SEQ ID NOs: 18, 27, 30, 34, 36, 37, 38, 39, 48, 49 or 51. In some embodiments, the TβRII polypeptide lacks the amino acids corresponding to the first, second and third amino acids (threonine, isoleucine, and proline, respectively) of any one of SEQ ID NOs: 18, 27, 30, 34, 36, 37, 38, 39, 48, 49 or 51. In some embodiments, the TβRII polypeptide lacks the amino acids corresponding to the first, second, third and fourth amino acids (threonine, isoleucine, proline, proline, respectively) of any one of SEQ ID NOs: 18, 27, 30, 34, 36, 37, 38, 39, 48, 49 or 51.

In some embodiments, any of the TβRII polypeptides disclosed herein are at least 80%, 85%, 90%, 92%, 94%, 95%, 97%, 99% or 100% identical to the amino acid sequence of any one of SEQ ID NOs: 18 or 51, but lack the amino acid corresponding to the first amino acid (threonine) of SEQ ID NO: 18 or 51. In some embodiments, the TβRII polypeptide lacks the amino acids corresponding to the first and second amino acids (threonine and isoleucine, respectively) of SEQ ID NO: 18 or 51. In some embodiments, the TβRII polypeptide lacks the amino acids corresponding to the first, second and third amino acids (threonine, isoleucine, and proline, respectively) of SEQ ID NO: 18 or 51. In some embodiments, the TβRII polypeptide lacks the amino acids corresponding to the first, second, third and fourth amino acids (threonine, isoleucine, proline, proline, respectively) of SEQ ID NO: 18 or 51.

In some embodiments, the disclosure provides for a composition comprising a mixture of TβRII polypeptides, wherein the TβRII polypeptides in the composition each comprise an amino acid sequence that is at least 80%, 85%, 90%, 92%, 94%, 95%, 97%, 99% or 100% identical to the amino acid sequence of any one of SEQ ID NOs: 18, 27, 30, 34, 36, 37, 38, 39, 48, 49 or 51; but wherein at least a portion of the TβRII polypeptides (e.g., at least 1%, 3%, 4%, 5%, 10%, 15%, 20%, 25%, 30%, 40%, 50%, 60%, 70%, 80%, 90%, 95%) in the composition include the amino acids corresponding to the first, second, third and fourth amino acids (threonine, isoleucine, proline and proline, respectively) of any one of SEQ ID NOs: 18, 27, 30, 34, 36, 37, 38, 39, 48, 49 or 51; and wherein at least a portion of the TβRII polypeptides (e.g., at least 1%, 3%, 4%, 5%, 10%, 15%, 20%, 25%, 30%, 40%, 50%, 60%, 70%, 80%, 90%, 95%) in the composition lack one or more of the amino acids corresponding to the first, second, third and fourth amino acids (threonine, isoleucine, proline and proline, respectively) of any one of SEQ ID NOs: 18, 27, 30, 34, 36, 37, 38, 39, 48, 49 or 51. In some embodiments, the disclosure provides for a composition comprising a mixture of TβRII polypeptides, wherein the TβRII polypeptides are at least 80%, 85%, 90%, 92%, 94%, 95%, 97%, 99% or 100% identical to the amino acid sequence of any one of SEQ ID NOs: 18 or 51, but wherein at least 30% to 80% of the TβRII polypeptides in the composition lack the amino acid corresponding to the first amino acid (threonine) of SEQ ID NO: 18 or 51.

In certain embodiments, the present disclosure contemplates specific mutations of the TβRII polypeptides so as to alter the glycosylation of the polypeptide. Such mutations may be selected so as to introduce or eliminate one or more glycosylation sites, such as O-linked or N-linked glycosylation sites. Asparagine-linked glycosylation recognition sites generally comprise a tripeptide sequence, asparagine-X-threonine (or asparagine-X-serine) (where "X" is any amino acid) which is specifically recognized by appropriate cellular glycosylation enzymes. The alteration may also be made by the addition of, or substitution by, one or more serine or threonine residues to the sequence of the wild-type TβRII polypeptide (for O-linked glycosylation sites). A variety of amino acid substitutions or deletions at one or both of the first or third amino acid positions of a glycosylation recognition site (and/or amino acid deletion at the second position) results in non-glycosylation at the modified tripeptide sequence. Another means of increasing the number of carbohydrate moieties on a TβRII polypeptide is by chemical or enzymatic coupling of glycosides to the TβRII polypeptide. Depending on the coupling mode used, the sugar(s) may be attached to (a) arginine and histidine; (b) free carboxyl groups; (c) free sulfhydryl groups such as those of cysteine; (d) free hydroxyl groups such as those of serine, threonine, or hydroxyproline; (e) aromatic residues such as those of phenylalanine, tyrosine, or tryptophan; or (0 the amide group of glutamine. These methods are described in WO 87/05330 published Sep. 11, 1987, and in Aplin and Wriston (1981) CRC Crit. Rev. Biochem., pp. 259-306, incorporated by reference herein. Removal of one or more carbohydrate moieties present on a TβRII polypeptide may be accomplished chemically and/or enzymatically. Chemical deglycosylation may involve, for example, exposure of the TβRII polypeptide to the compound trifluoromethane-sulfonic acid, or an equivalent compound. This treatment results in the cleavage of most or all sugars except the linking sugar (N-acetylglucosamine or N-acetylgalactosamine), while leaving the amino acid sequence intact. Chemical deglycosylation is further described by Hakimuddin et al. (1987) Arch. Biochem. Biophys. 259:52 and by Edge et al. (1981) Anal. Biochem. 118:131. Enzymatic cleavage of carbohydrate moieties on TβRII polypeptides can be achieved by the use of a variety of endo- and exo-glycosidases as described by Thotakura et al. (1987) Meth. Enzymol. 138:350. The sequence of a TβRII polypeptide may be adjusted, as appropriate, depending on the type of expression system used, as mammalian, yeast, insect and plant cells may all introduce differing glycosylation patterns that can be affected by the amino acid sequence of the peptide. In general, TβRII polypeptides for use in humans will be expressed in a mammalian cell line that provides proper glycosylation, such as HEK293 or CHO cell lines, although other mammalian expression cell lines, yeast cell lines with engineered glycosylation enzymes, and insect cells are expected to be useful as well.

This disclosure further contemplates a method of generating mutants, particularly sets of combinatorial mutants of a TβRII polypeptide, as well as truncation mutants; pools of combinatorial mutants are especially useful for identifying functional variant sequences. The purpose of screening such combinatorial libraries may be to generate, for example, TβRII polypeptide variants which can act as either agonists or antagonist, or alternatively, which possess novel activities all together. A variety of screening assays are provided below, and such assays may be used to evaluate variants. For example, a TβRII polypeptide variant may be screened for ability to bind to a TβRII ligand, to prevent binding of a TβRII ligand to a TβRII polypeptide or to interfere with signaling caused by a TβRII ligand. The activity of a TβRII polypeptide or its variants may also be tested in a cell-based or in vivo assay, particularly any of the assays disclosed in the Examples.

Combinatorially-derived variants can be generated which have a selective or generally increased potency relative to a TβRII polypeptide comprising an extracellular domain of a naturally occurring TβRII polypeptide. Likewise, mutagenesis can give rise to variants which have serum half-lives dramatically different than the corresponding wild-type TβRII polypeptide. For example, the altered protein can be rendered either more stable or less stable to proteolytic degradation or other processes which result in destruction of, or otherwise elimination or inactivation of, a native TβRII polypeptide. Such variants, and the genes which encode them, can be utilized to alter TβRII polypeptide levels by modulating the half-life of the TβRII polypeptides. For instance, a short half-life can give rise to more transient biological effects and can allow tighter control of recombinant TβRII polypeptide levels within the patient. In an Fc fusion protein, mutations may be made in the linker (if any) and/or the Fc portion to alter the half-life of the protein.

A combinatorial library may be produced by way of a degenerate library of genes encoding a library of polypeptides which each include at least a portion of potential TβRII polypeptide sequences. For instance, a mixture of synthetic oligonucleotides can be enzymatically ligated into gene sequences such that the degenerate set of potential TβRII polypeptide nucleotide sequences are expressible as individual polypeptides, or alternatively, as a set of larger fusion proteins (e.g., for phage display).

There are many ways by which the library of potential TβRII polypeptide variants can be generated from a degenerate oligonucleotide sequence. Chemical synthesis of a degenerate gene sequence can be carried out in an automatic DNA synthesizer, and the synthetic genes then be ligated into an appropriate vector for expression. The synthesis of degenerate oligonucleotides is well known in the art (see for example, Narang, S A (1983) Tetrahedron 39:3; Itakura et al., (1981) Recombinant DNA, Proc. 3rd Cleveland Sympos. Macromolecules, ed. AG Walton, Amsterdam: Elsevier pp 273-289; Itakura et al., (1984) Annu. Rev. Biochem. 53:323; Itakura et al., (1984) Science 198:1056; Ike et al., (1983) Nucleic Acid Res. 11:477). Such techniques have been employed in the directed evolution of other proteins (see, for example, Scott et al., (1990) Science 249:386-390; Roberts et al., (1992) PNAS USA 89:2429-2433; Devlin et al., (1990) Science 249: 404-406; Cwirla et al., (1990) PNAS USA 87: 6378-6382; as well as U.S. Pat. Nos. 5,223,409, 5,198,346, and 5,096,815).

Alternatively, other forms of mutagenesis can be utilized to generate a combinatorial library. For example, TβRII polypeptide variants can be generated and isolated from a library by screening using, for example, alanine scanning mutagenesis and the like (Ruf et al., (1994) Biochemistry 33:1565-1572; Wang et al., (1994) J. Biol. Chem. 269:3095-3099; Balint et al., (1993) Gene 137:109-118; Grodberg et al., (1993) Eur. J. Biochem. 218:597-601; Nagashima et al., (1993) J. Biol. Chem. 268:2888-2892; Lowman et al., (1991) Biochemistry 30:10832-10838; and Cunningham et al., (1989) Science 244:1081-1085), by linker scanning mutagenesis (Gustin et al., (1993) Virology 193:653-660; Brown et al., (1992) Mol. Cell Biol. 12:2644-2652; McKnight et al., (1982) Science 232:316); by saturation mutagenesis (Meyers et al., (1986) Science 232:613); by PCR mutagenesis (Leung et al., (1989) Method Cell Mol Biol 1:11-19); or by random mutagenesis, including chemical mutagenesis, etc. (Miller et al., (1992) A Short Course in Bacterial Genetics, CSHL Press, Cold Spring Harbor, N.Y.; and Greener et al., (1994) Strategies in Mol Biol 7:32-34). Linker scanning mutagenesis, particularly in a combinatorial setting, is an attractive method for identifying truncated (bioactive) forms of TβRII polypeptides.

A wide range of techniques are known in the art for screening gene products of combinatorial libraries made by point mutations and truncations, and, for that matter, for screening cDNA libraries for gene products having a certain property. Such techniques will be generally adaptable for rapid screening of the gene libraries generated by the combinatorial mutagenesis of TβRII polypeptides. The most widely used techniques for screening large gene libraries typically comprises cloning the gene library into replicable expression vectors, transforming appropriate cells with the resulting library of vectors, and expressing the combinatorial genes under conditions in which detection of a desired activity facilitates relatively easy isolation of the vector encoding the gene whose product was detected. Preferred assays include TβRII ligand binding assays and ligand-mediated cell signaling assays.

In certain embodiments, the TβRII polypeptides of the disclosure may further comprise post-translational modifications in addition to any that are naturally present in the TβRII polypeptides. Such modifications include, but are not limited to, acetylation, carboxylation, glycosylation, phosphorylation, lipidation, pegylation (polyethylene glycol) and acylation. As a result, the modified TβRII polypeptides may contain non-amino acid elements, such as polyethylene glycols, lipids, mono- or poly-saccharides, and phosphates. Effects of such non-amino acid elements on the functionality of a TβRII polypeptide may be tested as described herein for other TβRII polypeptide variants. When a TβRII polypeptide is produced in cells by cleaving a nascent form of the TβRII polypeptide, post-translational processing may also be important for correct folding and/or function of the protein. Different cells (such as CHO, HeLa, MDCK, 293, WI38, NIH-3T3 or HEK-293) have specific cellular machinery and characteristic mechanisms for such post-translational activities and may be chosen to ensure the correct modification and processing of the TβRII polypeptides.

3. Linkers

The disclosure provide for TβRII fusion proteins, and in these embodiments, the TβRII portion is connected to the heterologous portion (e.g., Fc portion) by means of a linker. In some embodiments, the linkers are glycine and serine rich linkers. Other near neutral amino acids, such as, but not limited to, Thr, Asn, Pro and Ala, may also be used in the linker sequence. In some embodiments, the linker comprises various permutations of amino acid sequences containing Gly and Ser. In some embodiments, the linker is greater than 10 amino acids in length. In further embodiments, the linkers have a length of at least 12, 15, 20, 21, 25, 30, 35, 40, 45 or 50 amino acids. In some embodiments, the linker is less than 40, 35, 30, 25, 22 or 20 amino acids. In some embodiments, the linker is 10-50, 10-40, 10-30, 10-25, 10-21, 10-15, 10, 15-25, 17-22, 20, or 21 amino acids in length. In preferred embodiments, the linker comprises the amino acid sequence GlyGlyGlyGlySer (GGGGS) (SEQ ID NO: 19), or repetitions thereof (GGGGS)n, where n≥2 (SEQ ID NO: 57). In particular embodiments n≥3, or n=3-10. The application teaches the surprising finding that proteins comprising a TβRII portion and a heterologous portion fused together by means of a (GGGGS)4 linker (SEQ ID NO: 58) were associated with a stronger affinity for TGFβ1 and TGFβ3 as compared to a TβRII fusion protein where n<4. As such, in preferred embodiments, n≥4, or n=4-10. The application also teaches that proteins comprising (GGGGS)n linkers ('GGGGS' disclosed as SEQ ID NO: 19) in which n>4 had similar inhibitory properties as proteins having the (GGGGS)$_4$ linker (SEQ ID NO: 58). As such, in some embodiments, n is not greater than 4 in a (GGGGS)n linker (SEQ ID NO: 19). In some embodiments, n=4-10, 4-9, 4-8, 4-7, 4-6, 4-5, 5-8, 5-7, or 5-6. In some embodiments, n=3, 4, 5, 6, or 7. In particular embodiments, n=4. In some embodiments, a linker comprising a (GGGGS)n sequence (SEQ ID NO: 19) also comprises an N-terminal threonine. In some embodiments, the linker is any one of the following:

```
                             (SEQ ID NO: 21)
GGGGSGGGGS (SEQ ID NO: 4)
TGGGGSGGGGS (SEQ ID NO: 5)
TGGGGSGGGGSGGGGS (SEQ ID NO: 6)
TGGGGSGGGGSGGGGSGGGGS
```

-continued

TGGGGSGGGGSGGGGSGGGGSGGGGS (SEQ ID NO: 25)

TGGGGSGGGGSGGGGSGGGGSGGGGSGGGGS (SEQ ID NO: 26)
or

TGGGGSGGGGSGGGGSGGGGSGGGGSGGGGSGGGGS. (SEQ ID NO: 40)

In some embodiments, the linker comprises the amino acid sequence of TGGGPKSCDK (SEQ ID NO: 7). In some embodiments, the linker is any one of SEQ ID NOs: 21, 4-7, 25-26 or 40 lacking the N-terminal threonine. In some embodiments, the linker does not comprise the amino acid sequence of SEQ ID NO: 26 or 40.

4. Heterologous Portions

In certain aspects, functional variants or modified forms of the TβRII polypeptides include fusion proteins having at least a portion of the TβRII polypeptides and one or more heterologous portions. Well-known examples of such heterologous portions include, but are not limited to, polyhistidine, Glu-Glu, glutathione S transferase (GST), thioredoxin, protein A, protein G, an immunoglobulin heavy chain constant region (Fc), maltose binding protein (MBP), or human serum albumin. A heterologous portion may be selected so as to confer a desired property. For example, some heterologous portions are particularly useful for isolation of the fusion proteins by affinity chromatography. For the purpose of affinity purification, relevant matrices for affinity chromatography, such as glutathione-, amylase-, and nickel- or cobalt-conjugated resins are used. Many of such matrices are available in "kit" form, such as the Pharmacia GST purification system and the QIAexpress™ system (Qiagen) useful with (HIS$_6$ (SEQ ID NO: 61)) fusion partners. As another example, a heterologous portion may be selected so as to facilitate detection of the TβRII polypeptides. Examples of such detection domains include the various fluorescent proteins (e.g., GFP) as well as "epitope tags," which are usually short peptide sequences for which a specific antibody is available. Well known epitope tags for which specific monoclonal antibodies are readily available include FLAG, influenza virus haemagglutinin (HA), and c-myc tags. In some cases, the heterologous portions have a protease cleavage site, such as for Factor Xa or Thrombin, which allows the relevant protease to partially digest the fusion proteins and thereby liberate the recombinant proteins therefrom. The liberated proteins can then be isolated from the heterologous portion by subsequent chromatographic separation. In certain preferred embodiments, a TβRII polypeptide is fused with a domain that stabilizes the TβRII polypeptide in vivo (a "stabilizer" domain). By "stabilizing" is meant anything that increases serum half life, regardless of whether this is because of decreased destruction, decreased clearance by the kidney, or other pharmacokinetic effect. Fusions with the Fc portion of an immunoglobulin are known to confer desirable pharmacokinetic properties on a wide range of proteins. Likewise, fusions to human serum albumin can confer desirable properties. Other types of heterologous portions that may be selected include multimerizing (e.g., dimerizing, tetramerizing) domains and functional domains.

As specific examples, the present disclosure provides fusion proteins comprising variants of TβRII polypeptides fused to an Fc domain sequence of SEQ ID NO: 20. Optionally, the Fc domain has one or more mutations at residues such as Asp-265, Lys-322, and Asn-434 (numbered in accordance with the corresponding full-length IgG). In certain cases, the mutant Fc domain having one or more of these mutations (e.g., Asp-265 mutation) has reduced ability of binding to the Fcγ receptor relative to a wildtype Fc domain. In other cases, the mutant Fc domain having one or more of these mutations (e.g., Asn-434 mutation) has increased ability of binding to the MHC class I-related Fc-receptor (FcRN) relative to a wildtype Fc domain.

It is understood that different elements of the fusion proteins may be arranged in any manner that is consistent with the desired functionality. For example, a TβRII polypeptide may be placed C-terminal to a heterologous domain, or, alternatively, a heterologous domain may be placed C-terminal to a TβRII polypeptide. The TβRII polypeptide domain and the heterologous domain need not be adjacent in a fusion protein, and additional domains or amino acid sequences may be included C- or N-terminal to either domain or between the domains.

As used herein, the term "immunoglobulin Fc domain" or simply "Fc" is understood to mean the carboxyl-terminal portion of an immunoglobulin chain constant region, preferably an immunoglobulin heavy chain constant region, or a portion thereof. For example, an immunoglobulin Fc region may comprise 1) a CH1 domain, a CH2 domain, and a CH3 domain, 2) a CH1 domain and a CH2 domain, 3) a CH1 domain and a CH3 domain, 4) a CH2 domain and a CH3 domain, or 5) a combination of two or more domains and an immunoglobulin hinge region. In a preferred embodiment the immunoglobulin Fc region comprises at least an immunoglobulin hinge region a CH2 domain and a CH3 domain, and preferably lacks the CH1 domain. In some embodiments, the immunoglobulin Fc region is a human immunoglobulin Fc region.

In one embodiment, the class of immunoglobulin from which the heavy chain constant region is derived is IgG (Igγ) (γ subclasses 1, 2, 3, or 4). Other classes of immunoglobulin, IgA (Igα), IgD (Igδ), IgE (Igε) and IgM (Igμ), may be used. The choice of appropriate immunoglobulin heavy chain constant region is discussed in detail in U.S. Pat. Nos. 5,541,087 and 5,726,044. The choice of particular immunoglobulin heavy chain constant region sequences from certain immunoglobulin classes and subclasses to achieve a particular result is considered to be within the level of skill in the art. The portion of the DNA construct encoding the immunoglobulin Fc region preferably comprises at least a portion of a hinge domain, and preferably at least a portion of a CH3 domain of Fc gamma or the homologous domains in any of IgA, IgD, IgE, or IgM.

Furthermore, it is contemplated that substitution or deletion of amino acids within the immunoglobulin heavy chain constant regions may be useful in the practice of the methods and compositions disclosed herein. One example would be to introduce amino acid substitutions in the upper CH2 region to create an Fc variant with reduced affinity for Fc receptors (Cole et al. (1997) J. Immunol. 159:3613).

In some embodiments, the disclosure provides for TβRII polypeptides fusion proteins comprising an amino acid sequence that is at least 80%, 85%, 90%, 95%, 96%, 97%, 98%, or 99% identical to the amino acid sequence of any one of SEQ ID NOs: 11, 13, 15 and 17, or biologically active fragments thereof. In some embodiments, the TβRII polypeptides fusion proteins comprise an amino acid sequence that is at least 80%, 85%, 90%, 95%, 96%, 97%, 98%, or 99% identical to the amino acid sequence of any one of SEQ ID NOs: 11, 13, and 15, or biologically active fragments thereof. In some embodiments, the TβRII polypeptides fusion proteins comprise an amino acid sequence that is at least 80%, 85%, 90%, 95%, 96%, 97%, 98%, or 99% identical to the amino acid sequence of any one of SEQ ID NO: 13, or a biologically active fragment thereof. In some embodiments, the TβRII polypeptides fusion proteins comprise an amino acid sequence that is at least 80%, 85%, 90%, 95%, 96%, 97%, 98%, or 99% identical to the amino acid sequence of any one of SEQ ID NO: 50, or a biologically active fragment thereof. In some embodiments, the TβRII polypeptides fusion proteins comprise an amino acid sequence that is at least 80%, 85%, 90%, 95%, 96%, 97%, 98%, or 99% identical to the amino acid sequence of any one of SEQ ID NO: 51, or a biologically active fragment thereof. In some embodiments, the TβRII polypeptides fusion proteins comprise an amino acid sequence that is at least 80%, 85%, 90%, 95%, 96%, 97%, 98%, or 99% identical to the amino acid sequence of any one of SEQ ID NO: 52, or a biologically active fragment thereof. In some embodiments, the TβRII polypeptides fusion proteins comprise an amino acid sequence that is at least 80%, 85%, 90%, 95%, 96%, 97%, 98%, or 99% identical to the amino acid sequence of any one of SEQ ID NO: 53, or a biologically active fragment thereof. In some embodiments, the TβRII polypeptides fusion proteins comprise an amino acid sequence that is at least 80%, 85%, 90%, 95%, 96%, 97%, 98%, or 99% identical to the amino acid sequence of any one of SEQ ID NO: 54, or a biologically active fragment thereof. In some embodiments, the TβRII polypeptides fusion proteins comprise an amino acid sequence that is at least 80%, 85%, 90%, 95%, 96%, 97%, 98%, or 99% identical to the amino acid sequence of any one of SEQ ID NO: 55, or a biologically active fragment thereof. In some embodiments, the TβRII polypeptides fusion proteins comprise an amino acid sequence that is at least 80%, 85%, 90%, 95%, 96%, 97%, 98%, or 99% identical to the amino acid sequence of any one of SEQ ID NO: 56, or a biologically active fragment thereof. In some embodiments, the TβRII polypeptides fusion protein comprises an amino acid sequence that is at least 80%, 85%, 90%, 95%, 96%, 97%, 98%, or 99% identical to the amino acid sequence of SEQ ID NO: 20, or a biologically active fragment thereof.

In some embodiments, the fusion proteins described herein have improved binding affinity for TGFβ1 and TGFβ3. In some embodiments, a fusion protein comprising a linker at least 10 amino acids in length (e.g., a fusion protein having the amino acid sequence of any one of SEQ ID NOs: 11, 13, 15, and 50-56) has improved binding affinity for TGFβ1 and TGFβ3 as compared to a reference fusion protein (e.g., a fusion protein having the amino acid sequence of SEQ ID NO: 9). In some embodiments, the fusion protein binds to TGFβ1 with a $K_D$ of less than 200 pM, less than 150 pM, less than 100 pM, less than 75 pM, less than 50 pM or less than 25 pM. In some embodiments, the fusion protein binds to TGFβ3 with a $K_D$ of less than 75 pM, less than 70 pM, less than 60 pM, less than 50 pM, less than 40 pM, less than 35 pM, less than 25 pM, less than 15, less than 10, or less than 5 pM.

In some embodiments any of the polypeptides disclosed herein inhibits TGFβ1 and/or TGFβ3 in a measurable assay. In some embodiments, the polypeptide inhibits TGFβ1 with an IC50 of less than 1.0, 0.9, 0.8. 0.7, 0.6, 0.5, 0.4, 0.3, 0.2, 0.1, 0.08, 0.09, 0.07, 0.06, 0.05, 0.04, 0.03, or 0.02 nM, as determined using a reporter gene assay. In some embodiments, the polypeptide inhibits TGFβ3 with an IC50 of less than 1.0, 0.9, 0.8. 0.7, 0.6, 0.5, 0.4, 0.3, 0.2, 0.1, 0.09, 0.08, 0.07, 0.06, 0.05, 0.04, 0.03, or 0.02 nM, as determined using a reporter gene assay. In some embodiments, the reporter gene assay is a CAGA reporter assay. In some embodiments, the CAGA assay is based on a human lung carcinoma cell line transfected with a pGL3(CAGA)12 reporter plasmid (Dennler et al, 1998, EMBO 17: 3091-3100) as well as a *Renilla* reporter plasmid (pRLCMV) to control for transfection efficiency. The CAGA motif is present in the promoters of TGFβ-responsive genes (for example, PAI-1), so this vector is of general use for factors signaling through SMAD2 and SMAD3. See, e.g., Example 2.

5. Fusion Polypeptides

In some embodiments, the disclosure provides for TβRII-containing fusion polypeptides. The fusion polypeptides may be prepared according to any of the methods disclosed herein or that are known in the art.

In some embodiments, any of the fusion polypeptides disclosed herein comprises the following components: a) any of the TβRII polypeptides disclosed herein ("A"), b) any of the linkers disclosed herein ("B"), c) any of the heterologous portions disclosed herein ("C"), and optionally a linker ("X"). In such embodiments, the fusion polypeptide may be arranged in a manner as follows (N-terminus to C-terminus): A-B-C or C-B-A. In such embodiments, the fusion polypeptide may be arranged in a manner as follows (N-terminus to C-terminus): X-A-B-C or X-C-B-A. In some embodiments, the fusion polypeptide comprises each of A, B and C (and optionally a leader sequence such as the amino acid sequence of SEQ ID NO: 23), and comprises no more than 100, 90, 80, 70, 60, 50, 40, 30, 20, 10, 5, 4, 3, 2 or 1 additional amino acids (but which may include further post-translational modifications, such as PEGylation).

In some embodiments, the fusion polypeptide comprises a leader sequence (e.g., SEQ ID NO: 23) positioned in a manner as follows (N-terminus to C-terminus): X-A-B-C, and the fusion polypeptide comprises 1, 2, 3, 4, or 5 amino acids between X and A. In some embodiments, the fusion polypeptide comprises a leader sequence (e.g., SEQ ID NO: 23) positioned in a manner as follows (N-terminus to C-terminus): X-C-B-A, and the fusion polypeptide comprises 1, 2, 3, 4, or 5 amino acids between X and C. In some embodiments, the fusion polypeptide comprises a leader sequence (e.g., SEQ ID NO: 23) positioned in a manner as follows (N-terminus to C-terminus): X-A-B-C, and the fusion polypeptide comprises an alanine between X and A. In some embodiments, the fusion polypeptide comprises a leader sequence (e.g., SEQ ID NO: 23) positioned in a manner as follows (N-terminus to C-terminus): X-C-B-A, and the fusion polypeptide comprises an alanine between X and C. In some embodiments, the fusion polypeptide comprises a leader sequence (e.g., SEQ ID NO: 23) positioned in a manner as follows (N-terminus to C-terminus): X-A-B-C, and the fusion polypeptide comprises a glycine and an alanine between X and A. In some embodiments, the fusion polypeptide comprises a leader sequence (e.g., SEQ ID NO: 23) positioned in a manner as follows (N-terminus to C-terminus): X-C-B-A, and the fusion polypeptide comprises a glycine and an alanine between X and C. In some embodiments, the fusion polypeptide comprises a leader sequence (e.g., SEQ ID NO: 23) positioned in a manner as follows (N-terminus to C-terminus): X-A-B-C, and the fusion polypeptide comprises a threonine between X and A. In some embodiments, the fusion polypeptide comprises a leader sequence (e.g., SEQ ID NO: 23) positioned in a manner as follows (N-terminus to C-terminus): X-C-B-A, and the fusion polypeptide comprises a threonine between X and C.

In some embodiments, the fusion polypeptide comprises an amino acid sequence that is at least 85%, 90%, 95%, 97%, or 99% identical to any of the TβRII polypeptide amino acid sequences disclosed herein (e.g., SEQ ID NO: 18), wherein the TβRII polypeptide portion of the fusion polypeptide comprises no more than 10, 9, 8, 7, 6, 5, 4, 3, 2 or 1 additional amino acids (but which may include further post-translational modifications, such as PEGylation). In some embodiments, the fusion polypeptide comprises an amino acid sequence that is at least 85%, 90%, 95%, 97%, or 99% identical to any of the linker sequences disclosed herein (e.g., SEQ ID NO: 6), wherein the linker portion of the fusion polypeptide comprises no more than 5, 4, 3, 2 or 1 additional amino acids (but which may include further post-translational modifications, such as PEGylation). In some embodiments, the fusion polypeptide comprises an amino acid sequence that is at least 85%, 90%, 95%, 97%, or 99% identical to any of the heterologous portion sequences disclosed herein (e.g., SEQ ID NO: 20), wherein the heterologous portion of the fusion polypeptide comprises no more than 25, 20, 15, 10, 5, 4, 3, 2, or 1 additional amino acids (but which may include further post-translational modifications, such as PEGylation). In some embodiments, the fusion polypeptide comprises any of the TβRII polypeptide amino acid sequences disclosed herein (e.g., SEQ ID NO: 18), wherein the TβRII polypeptide portion of the fusion polypeptide comprises no more than 10, 9, 8, 7, 6, 5, 4, 3, 2 or 1 additional amino acids (but which may include further post-translational modifications, such as PEGylation). In some embodiments, the fusion polypeptide comprises any of the linker sequences disclosed herein (e.g., SEQ ID NO: 6), wherein the linker portion of the fusion polypeptide comprises no more than 5, 4, 3, 2 or 1 additional amino acids (but which may include further post-translational modifications, such as PEGylation). In some embodiments, the fusion polypeptide comprises any of the heterologous portion sequences disclosed herein (e.g., SEQ ID NO: 20), wherein the heterologous portion of the fusion polypeptide comprises no more than 25, 20, 15, 10, 5, 4, 3, 2, or 1 additional amino acids (but which may include further post-translational modifications, such as PEGylation).

In some embodiments, the disclosure provides for a fusion polypeptide, wherein the fusion polypeptide consists or consists essentially of (and not necessarily in the following order): a) an amino acid sequence that is at least 85%, 90%, 95%, 97%, or 99% identical to any of the TβRII polypeptide amino acid sequences disclosed herein (e.g., SEQ ID NO: 18), wherein the TβRII polypeptide portion of the fusion polypeptide comprises no more than 10, 9, 8, 7, 6, 5, 4, 3, 2 or 1 additional amino acids (but which may include further post-translational modifications, such as PEGylation); b) an amino acid sequence that is at least 85%, 90%, 95%, 97%, or 99% identical to any of the linker sequences disclosed herein (e.g., SEQ ID NO: 6), wherein the linker portion of the fusion polypeptide comprises no more than 5, 4, 3, 2 or 1 additional amino acids (but which may include further post-translational modifications, such as PEGylation); and c) an amino acid sequence that is at least 85%, 90%, 95%, 97%, or 99% identical to any of the heterologous portion sequences disclosed herein (e.g., SEQ ID NO: 20), wherein the heterologous portion of the fusion polypeptide comprises no more than 25, 20, 15, 10, 5, 4, 3, 2, or 1 additional amino acids (but which may include further post-translational modifications, such as PEGylation); and d) optionally a leader sequence (e.g., SEQ ID NO: 23). In some embodiments, the disclosure provides for a fusion polypeptide, wherein the fusion polypeptide consists or consists essentially of (and not necessarily in the following order): a) any of the TβRII polypeptide amino acid sequences disclosed herein (e.g., SEQ ID NO: 18), wherein the TβRII polypeptide portion of the fusion polypeptide comprises no more than 10, 9, 8, 7, 6, 5, 4, 3, 2 or 1 additional amino acids (but which may include further post-translational modifications, such as PEGylation); b) any of the linker sequences disclosed herein (e.g., SEQ ID NO: 6), wherein the linker portion of the fusion polypeptide comprises no more than 5, 4, 3, 2 or 1 additional amino acids (but which may include further post-translational modifications, such as PEGylation); and c) any of the heterologous portion sequences disclosed herein (e.g., SEQ ID NO: 20), wherein the heterologous portion of the fusion polypeptide comprises no more than 25, 20, 15, 10, 5, 4, 3, 2, or 1 additional amino acids (but which may include further post-translational modifications, such as PEGylation); and d) optionally a leader sequence (e.g., SEQ ID NO: 23).

In some embodiments, the disclosure provides for a fusion polypeptide consisting of or consisting essentially of (and not necessarily in the following order): a) a TβRII polypeptide portion consisting of an amino acid sequence that is at least 85%, 90%, 95%, 97%, or 99% identical to the amino acid sequence of SEQ ID NO: 18 and no more than 10, 9, 8, 7, 6, 5, 4, 3, 2 or 1 additional amino acids (but which may include further post-translational modifications, such as PEGylation); b) a linker portion consisting of an amino acid sequence that is at least 85%, 90%, 95%, 97%, or 99% identical to the amino acid sequence of SEQ ID NO: 6 and no more than 5, 4, 3, 2 or 1 additional amino acids (but which may include further post-translational modifications, such as PEGylation); and c) a heterologous portion consisting of an amino acid sequence that is at least 85%, 90%, 95%, 97%, or 99% identical to the amino acid sequence of SEQ ID NO: 20 and no more than 25, 20, 15, 10, 5, 4, 3, 2, or 1 additional amino acids (but which may include further post-translational modifications, such as PEGylation); and d) optionally a leader sequence (e.g., SEQ ID NO: 23). In some embodiments, the disclosure provides for a fusion polypeptide consisting or consisting essentially of (and not necessarily in the following order): a) a TβRII polypeptide portion consisting of the amino acid sequence of SEQ ID NO: 18 and no more than 10, 9, 8, 7, 6, 5, 4, 3, 2 or 1 additional amino acids (but which may include further post-translational modifications, such as PEGylation); b) a linker portion consisting of the amino acid sequence of SEQ ID NO: 6 and no more than 5, 4, 3, 2 or 1 additional amino acids (but which may include further post-translational modifications, such as PEGylation); and c) a heterologous portion consisting of the amino acid sequence of SEQ ID NO: 20 and no more than 25, 20, 15, 10, 5, 4, 3, 2, or 1 additional amino acids (but which may include further post-translational modifications, such as PEGylation); and d) optionally a leader sequence (e.g., SEQ ID NO: 23).

In some embodiments, the fusion protein does not comprise a leader sequence. In some embodiments, the fusion protein comprises an amino acid sequence that is at least 85%, 90%, 92%, 95%, 96%, 97%, 99%, or 100% identical to the amino acid sequence of SEQ ID NO: 48.

(SEQ ID NO: 48)
TIPPHVQKSDVEMEAQKDEIICPSCNRTAHPLRHINNDMIVTDNNGAVKF

PQLCKFCDVRFSTCDNQKSCMSNCSITSICEKPQEVCVAVWRKNDENITL

```
-continued
ETVCHDPKLPYHDFILEDAASPKCIMKEKKKPGETFFMCSCSSDECNDNI

IFSEEYNTSNPDTGGGGSGGGGSGGGGSGGGGSTHTCPPCPAPELLGGPS

VFLFPPKPKDTLMISRTPEVTCVVVDVSHEDPEVKFNWYVDGVEVHNAKT

KPREEQYNSTYRVVSVLTVLHQDWLNGKEYKCKVSNKALPAPIEKTISKA

KGQPREPQVYTLPPSREEMTKNQVSLTCLVKGFYPSDIAVEWESNGQPEN

NYKTTPPVLDSDGSFFLYSKLTVDKSRWQQGNVFSCSVMHEALHNHYTQK

SLSLSPGK.
```

In some embodiments, the disclosure provides for a TβRII fusion polypeptide wherein the polypeptide does not comprise an antibody or antigen-binding portion thereof. In some embodiments, the polypeptide does not bind with appreciable affinity to a cytokine other than a transforming growth factor beta superfamily ligand (e.g., TGFβ1, TGFβ2 and/or TGFβ3). In some embodiments, the polypeptide does not bind with appreciable affinity to a cytokine other than TGFβ1, TGFβ2 and/or TGFβ3. In some embodiments, the polypeptide does not bind with appreciable affinity to a cytokine other than TGFβ1 and/or TGFβ3. In some embodiments, the polypeptide does not bind with appreciable affinity to CD4, CD8, CD25, CTLA-4, IL-10, TGFβ Receptor, PD-1, PD-L1, PD-L2, RANK, RANKL, HER2/neu, EGFR1, CD20, VEGF, TNF-α, TNFR2, FoxP3, CD80, CD86, IFN-α, IFN-β, IFN-γ, GITR, 4-1BB, OX-40, TLR1-10, ErbB-1, HER1, ErbB-3/HER3, ErbB-4/HER4, IGFR, IGFBP, IGF-1R, PDGFR, FGFR, VEGFR, HGFR, TRK receptor, ephrin receptors, AXL receptors, LTK receptors, TIE receptors, angiopoietinl, 2, ROR receptor, DDR receptor, RET receptor, KLG receptor, RYK receptor, MuSK receptor, ILβR, IIαR, TNTRSF, TRAIL receptor, ARTC1, alpha-actinin-4, Bcr-abl, B-RAF, caspases, beta-catenin, fibronectin, GPNMB, GDP-L, LDLR, HLA-A2, MLA-A11, HSP70, KIAA205, MART2, MUM-1, 2, 3, PAP, neo-PAP, NFYC, OGT, OS-9, pml-RARalpha fusion protein, PRDX5, PTPRK, KRAS2, NRAS, HRAS, RBAF600, SIRT2. SNRPD1, SYT-SSX1 or -SSX2 fusion protein, Triosephosphate Isomerase, BAGE, BAGE-1. BAGE-2, 3, 4, 5 GAGE-1, 2, 3, 4, 5, 6, 7, 8, GnT-V, HERV-K MEL, KK-LC, LAGE, LAGE-1, CAMEL, MAGE-1, MAGE-A2, MAGE-A3, MAGE-A4, MAGE-AS, MAGE-A6, MAGE-A8, MAGE-A9, MAGE-A10. MAGE-A11, MAGE-A12, MAGE-3, MAGE-B1, MAGE-B2, MAGE-B5. MAGE-B6, MAGE-C1, MAGE-C2, mucin 1 (MUC1), MART-1/ Melan-A (MLANA), gp100, gp100/Pme117 (S1LV), tyrosinase (TYR), TRP-1, HAGE, NA-88, NY-ESO-1, NY-ESO-1/LAGE-2, SAGE, Sp17. SSX-1, 2, 3, 4, TRP2-1NT2, carcino-embryonic antigen (CEA), Kallikfein 4, mammaglobm-A, OA1, prostate specific antigen (PSA), prostate specific membrane antigen, TRP-1/, 75. TRP-2, AIM-2. BING-4, CPSF, cyclin D1, Ep-CAM, EpbA3, FGF-5, gp250, iCE), AFP, M-CSF, mdm-2, MUCI, p53 (TP53), PBF, FRAME, PSMA, RAGE-1. RNF43, RU2AS, SOX10, STEAP1, survivin (BIRCS), hTERT, telomerase, WT1, SYCP1, BRDT, SPANX, XAGE, ADAM2, PAGE-5, LIP1, CTAGE-1, CSAGE, MMA1, CAGE, BORIS, HOM-TES-85, AF15q14, HCA66I, LDHC, MORC, SGY-1a, SPO11, TPX1, NY-SAR-35, FTHLI7, NXF2 TDRD1, TEX 15, FATE, TPTE, estrogen receptors (ER), androgen receptors (AR), CD40, CD30, CD20, CD19, CD33, CD4, CD25, CD3, CA 72-4, CA 15-3, CA 27-29, CA 125, CA 19-9, beta-human chorionic gonadotropin, 1-2 microglobulin, squamous cell carcinoma antigen, neuron-specific enoJase, heat shock protein gp96, GM2, sargramostim, CTLA-4, 707-AP, ART-4, CAP-1, CLCA2, Cyp-B, HST-2, HPV proteins, EBV proteins, Hepatitis B or C virus proteins, and/or HIV proteins.

In some embodiments, the disclosure provides for a TβRII fusion polypeptide wherein the polypeptide does not comprise an additional ligand binding domain in addition to the TβRII domain. In some embodiments, the polypeptide comprises a linear amino acid sequence comprising a TβRII domain and a heterologous portion (e.g., an Fc portion), but the linear amino acid sequence does not comprise any additional ligand binding domains. In some embodiments, the polypeptide comprises a linear amino acid sequence comprising a TβRII domain and an Fc portion, but the linear amino acid sequence does not comprise any additional ligand binding domains. In some embodiments, the disclosure provides for a TβRII fusion polypeptide wherein the polypeptide does not comprise multiple ligand binding domains in a single linear amino acid sequence. In some embodiments, the disclosure provides for a TβRII fusion polypeptide wherein the polypeptide does not comprise more than one continuous linker sequence in a single linear amino acid sequence. In some embodiments, the polypeptide does not comprise multiple continuous glycine and/or serine linkers (e.g., a linker comprising (GGGGS)n, wherein n=≥4 (SEQ ID NO: 59)) in a single linear amino acid sequence. In some embodiments, the disclosure provides for a TβRII fusion polypeptide wherein the heterologous portion is an Fc domain, and wherein only one continuous linker is covalently bound to the Fc domain. In some embodiments, the only one continuous linker comprises or consists of a (GGGGS)n linker, wherein n=≥4 (SEQ ID NO: 59).

6. Nucleic Acids and Methods of Manufacture

In certain embodiments, the present disclosure makes available isolated and/or purified forms of the TβRII polypeptides fusion proteins, which are isolated from, or otherwise substantially free of (e.g., at least 80%, 90%, 95%, 96%, 97%, 98%, or 99% free of), other proteins and/or other TβRII polypeptide species. TβRII polypeptides will generally be produced by expression from recombinant nucleic acids.

In certain embodiments, the disclosure includes nucleic acids encoding soluble TβRII polypeptides comprising the coding sequence for an extracellular portion of a TβRII protein. In further embodiments, this disclosure also pertains to a host cell comprising such nucleic acids. The host cell may be any prokaryotic or eukaryotic cell. For example, a polypeptide of the present disclosure may be expressed in bacterial cells such as E. coli, insect cells (e.g., using a baculovirus expression system), yeast, or mammalian cells. Other suitable host cells are known to those skilled in the art. Accordingly, some embodiments of the present disclosure further pertain to methods of producing the TβRII polypeptides.

In certain aspects, the disclosure provides isolated and/or recombinant nucleic acids encoding any of the TβRII polypeptides, including fragments, functional variants and fusion proteins disclosed herein. SEQ ID NOs: 10, 12 and 14 encode variants of TβRII extracellular domain fused to an IgG Fc domain. The subject nucleic acids may be single-stranded or double stranded. Such nucleic acids may be DNA or RNA molecules. These nucleic acids may be used, for example, in methods for making TβRII polypeptides or as direct therapeutic agents (e.g., in an antisense, RNAi or gene therapy approach).

In certain aspects, the subject nucleic acids encoding TβRII polypeptides are further understood to include nucleic acids that are variants of SEQ ID NOs: 10, 12 and 14. Variant nucleotide sequences include sequences that differ by one or more nucleotide substitutions, additions or deletions, such as allelic variants.

In certain embodiments, the disclosure provides isolated or recombinant nucleic acid sequences that are at least 80%, 85%, 90%, 95%, 96%, 97%, 98%, 99% or 100% identical to SEQ ID NOs: 10, 12 and 14. In particular embodiments, the disclosure provides isolated or recombinant nucleic acid sequences that are at least 80%, 85%, 90%, 95%, 96%, 97%, 98%, 99% or 100% identical to SEQ ID NO: 12, or fragments thereof. One of ordinary skill in the art will appreciate that nucleic acid sequences complementary to SEQ ID NOs: 10, 12 and 14, and variants of SEQ ID NOs: 10, 12 and 14 are also within the scope of this disclosure. In further embodiments, the nucleic acid sequences of the disclosure can be isolated, recombinant, and/or fused with a heterologous nucleotide sequence, or in a DNA library.

In other embodiments, nucleic acids of the disclosure also include nucleotide sequences that hybridize under highly stringent conditions to the nucleotide sequences designated in SEQ ID NOs: 10, 12 and 14 complement sequences of SEQ ID NOs: 10, 12 and 14, or fragments thereof. As discussed above, one of ordinary skill in the art will understand readily that appropriate stringency conditions which promote DNA hybridization can be varied. For example, one could perform the hybridization at 6.0× sodium chloride/sodium citrate (SSC) at about 45° C., followed by a wash of 2.0×SSC at 50° C. For example, the salt concentration in the wash step can be selected from a low stringency of about 2.0×SSC at 50° C. to a high stringency of about 0.2×SSC at 50° C. In addition, the temperature in the wash step can be increased from low stringency conditions at room temperature, about 22° C., to high stringency conditions at about 65° C. Both temperature and salt may be varied, or temperature or salt concentration may be held constant while the other variable is changed. In some embodiments, the disclosure provides nucleic acids which hybridize under low stringency conditions of 6×SSC at room temperature followed by a wash at 2×SSC at room temperature.

Isolated nucleic acids which differ from the nucleic acids as set forth in SEQ ID NOs: 10, 12 and 14 due to degeneracy in the genetic code are also within the scope of the disclosure. For example, a number of amino acids are designated by more than one triplet. Codons that specify the same amino acid, or synonyms (for example, CAU and CAC are synonyms for histidine) may result in "silent" mutations which do not affect the amino acid sequence of the protein. However, it is expected that DNA sequence polymorphisms that do lead to changes in the amino acid sequences of the subject proteins will exist among mammalian cells. One skilled in the art will appreciate that these variations in one or more nucleotides (up to about 3-5% of the nucleotides) of the nucleic acids encoding a particular protein may exist among individuals of a given species due to natural allelic variation. Any and all such nucleotide variations and resulting amino acid polymorphisms are within the scope of this disclosure.

It will be appreciated by one of skill in the art that corresponding variants based on the long isoform of TβRII will include nucleotide sequences encoding the 25-amino acid insertion along with a conservative Val-Ile substitution at the flanking position C-terminal to the insertion. It will also be appreciated that corresponding variants based on either the long (A) or short (B) isoforms of TβRII will include variant nucleotide sequences comprising an insertion of 108 nucleotides, encoding a 36-amino-acid insertion (SEQ ID NO: 41), at the same location described for naturally occurring TβRII isoform C.

In certain embodiments, the recombinant nucleic acids of the disclosure may be operably linked to one or more regulatory nucleotide sequences in an expression construct. Regulatory nucleotide sequences will generally be appropriate to the host cell used for expression. Numerous types of appropriate expression vectors and suitable regulatory sequences are known in the art for a variety of host cells. Typically, said one or more regulatory nucleotide sequences may include, but are not limited to, promoter sequences, leader or signal sequences, ribosomal binding sites, transcriptional start and termination sequences, translational start and termination sequences, and enhancer or activator sequences. Constitutive or inducible promoters as known in the art are contemplated by the disclosure. The promoters may be either naturally occurring promoters, or hybrid promoters that combine elements of more than one promoter. An expression construct may be present in a cell on an episome, such as a plasmid, or the expression construct may be inserted in a chromosome. In a preferred embodiment, the expression vector contains a selectable marker gene to allow the selection of transformed host cells. Selectable marker genes are well known in the art and will vary with the host cell used.

In certain aspects disclosed herein, the subject nucleic acid is provided in an expression vector comprising a nucleotide sequence encoding a TβRII polypeptide and operably linked to at least one regulatory sequence. Regulatory sequences are art-recognized and are selected to direct expression of the TβRII polypeptide. Accordingly, the term regulatory sequence includes promoters, enhancers, and other expression control elements. Exemplary regulatory sequences are described in Goeddel; *Gene Expression Technology: Methods in Enzymology*, Academic Press, San Diego, Calif. (1990). For instance, any of a wide variety of expression control sequences that control the expression of a DNA sequence when operatively linked to it may be used in these vectors to express DNA sequences encoding a TβRII polypeptide. Such useful expression control sequences, include, for example, the early and late promoters of SV40, tet promoter, adenovirus or cytomegalovirus immediate early promoter, RSV promoters, the lac system, the trp system, the TAC or TRC system, T7 promoter whose expression is directed by T7 RNA polymerase, the major operator and promoter regions of phage lambda, the control regions for fd coat protein, the promoter for 3-phosphoglycerate kinase or other glycolytic enzymes, the promoters of acid phosphatase, e.g., Pho5, the promoters of the yeast α-mating factors, the polyhedron promoter of the baculovirus system and other sequences known to control the expression of genes of prokaryotic or eukaryotic cells or their viruses, and various combinations thereof. It should be understood that the design of the expression vector may depend on such factors as the choice of the host cell to be transformed and/or the type of protein desired to be expressed. Moreover, the vector's copy number, the ability to control that copy number and the expression of any other protein encoded by the vector, such as antibiotic markers, should also be considered.

A recombinant nucleic acid included in the disclosure can be produced by ligating the cloned gene, or a portion thereof, into a vector suitable for expression in either prokaryotic cells, eukaryotic cells (yeast, avian, insect or mammalian), or both. Expression vehicles for production of a recombinant TβRII polypeptide include plasmids and other vectors. For instance, suitable vectors include plasmids of the types: pBR322-derived plasmids, pEMBL-derived plasmids, pEX-derived plasmids, pBTac-derived plasmids and pUC-derived plasmids for expression in prokaryotic cells, such as E. coli.

Some mammalian expression vectors contain both prokaryotic sequences to facilitate the propagation of the vector in bacteria, and one or more eukaryotic transcription units that are expressed in eukaryotic cells. The pcDNAI/amp, pcDNAI/neo, pRc/CMV, pSV2gpt, pSV2neo, pSV2-dhfr, pTk2, pRSVneo, pMSG, pSVT7, pko-neo and pHyg derived vectors are examples of mammalian expression vectors suitable for transfection of eukaryotic cells. Some of these vectors are modified with sequences from bacterial plasmids, such as pBR322, to facilitate replication and drug resistance selection in both prokaryotic and eukaryotic cells. Alternatively, derivatives of viruses such as the bovine papilloma virus (BPV-1), or Epstein-Barr virus (pHEBo, pREP-derived and p205) can be used for transient expression of proteins in eukaryotic cells. Examples of other viral (including retroviral) expression systems can be found below in the description of gene therapy delivery systems. The various methods employed in the preparation of the plasmids and in transformation of host organisms are well known in the art. For other suitable expression systems for both prokaryotic and eukaryotic cells, as well as general recombinant procedures, see *Molecular Cloning A Laboratory Manual,* 3rd Ed., ed. by Sambrook, Fritsch and Maniatis (Cold Spring Harbor Laboratory Press, 2001). In some instances, it may be desirable to express the recombinant polypeptides by the use of a baculovirus expression system. Examples of such baculovirus expression systems include pVL-derived vectors (such as pVL1392, pVL1393 and pVL941), pAcUW-derived vectors (such as pAcUW1), and pBlueBac-derived vectors (such as the β-gal containing pBlueBac III).

In certain embodiments, a vector will be designed for production of the subject TβRII polypeptides in CHO cells, such as a Pcmv-Script vector (Stratagene, La Jolla, Calif.), pcDN4 vectors (Invitrogen, Carlsbad, Calif.) and pCI-neo vectors (Promega, Madison, Wis.). In a preferred embodiment, a vector will be designed for production of the subject TβRII polypeptides in HEK-293 cells. As will be apparent, the subject gene constructs can be used to cause expression of the subject TβRII polypeptides in cells propagated in culture, e.g., to produce proteins, including fusion proteins or variant proteins, for purification.

This disclosure also pertains to a host cell transfected with a recombinant gene including a coding sequence (e.g., SEQ ID NOs: 10, 12, or 14) for one or more of the subject TβRII polypeptides. The host cell may be any prokaryotic or eukaryotic cell. For example, a TβRII polypeptide disclosed herein may be expressed in bacterial cells such as E. coli, insect cells (e.g., using a baculovirus expression system), yeast, or mammalian cells. Other suitable host cells are known to those skilled in the art.

Accordingly, the present disclosure further pertains to methods of producing the subject TβRII polypeptides. For example, a host cell transfected with an expression vector encoding a TβRII polypeptide can be cultured under appropriate conditions to allow expression of the TβRII polypeptide to occur. The TβRII polypeptide may be secreted and isolated from a mixture of cells and medium containing the TβRII polypeptide. Alternatively, the TβRII polypeptide may be retained cytoplasmically or in a membrane fraction and the cells harvested, lysed and the protein isolated. A cell culture includes host cells, and media. Suitable media for cell culture are well known in the art. The subject TβRII polypeptides can be isolated from cell culture medium, host cells, or both, using techniques known in the art for purifying proteins, including ion-exchange chromatography, gel filtration chromatography, ultrafiltration, electrophoresis, immunoaffinity purification with antibodies specific for particular epitopes of the TβRII polypeptides and affinity purification with an agent that binds to a domain fused to the TβRII polypeptide (e.g., a protein A column may be used to purify an TβRII-Fc fusion). In a preferred embodiment, the TβRII polypeptide is a fusion protein containing a domain which facilitates its purification. As an example, purification may be achieved by a series of column chromatography steps, including, for example, three or more of the following, in any order: protein A chromatography, Q sepharose chromatography, phenylsepharose chromatography, size exclusion chromatography, and cation exchange chromatography. The purification could be completed with viral filtration and buffer exchange.

In another embodiment, a fusion gene coding for a purification leader sequence, such as a poly-(His)/enterokinase cleavage site sequence at the N-terminus of the desired portion of the recombinant TβRII polypeptide, can allow purification of the expressed fusion protein by affinity chromatography using a $Ni^{2+}$ metal resin. The purification leader sequence can then be subsequently removed by treatment with enterokinase to provide the purified TβRII polypeptide (e.g., see Hochuli et al., (1987) *J. Chromatography* 411:177; and Janknecht et al., *PNAS USA* 88:8972).

Techniques for making fusion genes are well known. Essentially, the joining of various DNA fragments coding for different polypeptide sequences is performed in accordance with conventional techniques, employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed to generate a chimeric gene sequence (see, for example, *Current Protocols in Molecular Biology,* eds. Ausubel et al., John Wiley & Sons: 1992).

7. Alterations in Fe-Fusion Proteins

The application further provides TβRII-Fc fusion proteins with engineered or variant Fc regions. Such antibodies and Fc fusion proteins may be useful, for example, in modulating effector functions, such as, antigen-dependent cytotoxicity (ADCC) and complement-dependent cytotoxicity (CDC). Additionally, the modifications may improve the stability of the antibodies and Fc fusion proteins. Amino acid sequence variants of the antibodies and Fc fusion proteins are prepared by introducing appropriate nucleotide changes into the DNA, or by peptide synthesis. Such variants include, for example, deletions from, and/or insertions into and/or substitutions of, residues within the amino acid sequences of the antibodies and Fc fusion proteins disclosed herein. Any combination of deletion, insertion, and substitution is made to arrive at the final construct, provided that the final construct possesses the desired characteristics. The amino acid changes also may alter post-translational processes of the antibodies and Fc fusion proteins, such as changing the number or position of glycosylation sites.

Antibodies and Fc fusion proteins with reduced effector function may be produced by introducing changes in the amino acid sequence, including, but are not limited to, the Ala-Ala mutation described by Bluestone et al. (see WO 94/28027 and WO 98/47531; also see Xu et al. 2000 Cell Immunol 200; 16-26). Thus, in certain embodiments, Fc fusion proteins of the disclosure with mutations within the constant region including the Ala-Ala mutation may be used to reduce or abolish effector function. According to these embodiments, antibodies and Fc fusion proteins may comprise a mutation to an alanine at position 234 or a mutation to an alanine at position 235, or a combination thereof. In one embodiment, the antibody or Fc fusion protein comprises an IgG4 framework, wherein the Ala-Ala mutation would describe a mutation(s) from phenylalanine to alanine at position 234 and/or a mutation from leucine to alanine at position 235. In another embodiment, the antibody or Fc fusion protein comprises an IgG1 framework, wherein the Ala-Ala mutation would describe a mutation(s) from leucine to alanine at position 234 and/or a mutation from leucine to alanine at position 235. The antibody or Fc fusion protein may alternatively or additionally carry other mutations, including the point mutation K322A in the CH2 domain (Hezareh et al. 2001 J Virol. 75: 12161-8).

In particular embodiments, the antibody or Fc fusion protein may be modified to either enhance or inhibit complement dependent cytotoxicity (CDC). Modulated CDC activity may be achieved by introducing one or more amino acid substitutions, insertions, or deletions in an Fc region (see, e.g., U.S. Pat. No. 6,194,551). Alternatively or additionally, cysteine residue(s) may be introduced in the Fc region, thereby allowing interchain disulfide bond formation in this region. The homodimeric antibody thus generated may have improved or reduced internalization capability and/or increased or decreased complement-mediated cell killing. See Caron et al., J. Exp Med. 176:1191-1195 (1992) and Shopes, B. J. Immunol. 148:2918-2922 (1992), WO99/51642, Duncan & Winter Nature 322: 738-40 (1988); U.S. Pat. Nos. 5,648,260; 5,624,821; and WO94/29351.

8. Screening Assays

In certain aspects, the present invention relates to the use of TβRII polypeptides (e.g., soluble TβRII polypeptides) to identify compounds (agents) which are agonist or antagonists of the TGFβ1, TGFβ3 and TβRII signaling pathway. Compounds identified through this screening can be tested to assess their ability to modulate TGFβ1 and TGFβ3 signaling activity in vitro. Optionally, these compounds can further be tested in animal models to assess their ability to modulate tissue growth in vivo.

There are numerous approaches to screening for therapeutic agents for modulating tissue growth by targeting TGFβ1, TGFβ3 and TβRII polypeptides. In certain embodiments, high-throughput screening of compounds can be carried out to identify agents that perturb TGFβ1, TGFβ3 or TβRII-mediated cell signaling. In certain embodiments, the assay is carried out to screen and identify compounds that specifically inhibit or reduce binding of a TβRII polypeptide to TGFβ1 or TGFβ3. Alternatively, the assay can be used to identify compounds that enhance binding of a TβRII polypeptide to TGFβ1 or TGFβ3. In a further embodiment, the compounds can be identified by their ability to interact with a TGFβ1, TGFβ3 or TβRII polypeptide.

A variety of assay formats will suffice and, in light of the present disclosure, those not expressly described herein will nevertheless be comprehended by one of ordinary skill in the art. As described herein, the test compounds (agents) of the invention may be created by any combinatorial chemical method. Alternatively, the subject compounds may be naturally occurring biomolecules synthesized in vivo or in vitro. Compounds (agents) to be tested for their ability to act as modulators of tissue growth can be produced, for example, by bacteria, yeast, plants or other organisms (e.g., natural products), produced chemically (e.g., small molecules, including peptidomimetics), or produced recombinantly. Test compounds contemplated by the present invention include non-peptidyl organic molecules, peptides, polypeptides, peptidomimetics, sugars, hormones, and nucleic acid molecules. In a specific embodiment, the test agent is a small organic molecule having a molecular weight of less than about 2,000 daltons.

The test compounds of the invention can be provided as single, discrete entities, or provided in libraries of greater complexity, such as made by combinatorial chemistry. These libraries can comprise, for example, alcohols, alkyl halides, amines, amides, esters, aldehydes, ethers and other classes of organic compounds. Presentation of test compounds to the test system can be in either an isolated form or as mixtures of compounds, especially in initial screening steps. Optionally, the compounds may be optionally derivatized with other compounds and have derivatizing groups that facilitate isolation of the compounds. Non-limiting examples of derivatizing groups include biotin, fluorescein, digoxygenin, green fluorescent protein, isotopes, polyhistidine, magnetic beads, glutathione S transferase (GST), photoactivatible crosslinkers or any combinations thereof.

In many drug screening programs which test libraries of compounds and natural extracts, high throughput assays are desirable in order to maximize the number of compounds surveyed in a given period of time. Assays which are performed in cell-free systems, such as may be derived with purified or semi-purified proteins, are often preferred as "primary" screens in that they can be generated to permit rapid development and relatively easy detection of an alteration in a molecular target which is mediated by a test compound. Moreover, the effects of cellular toxicity or bioavailability of the test compound can be generally ignored in the in vitro system, the assay instead being focused primarily on the effect of the drug on the molecular target as may be manifest in an alteration of binding affinity between a TβRII polypeptide and TGFβ1 or TGFβ3.

Merely to illustrate, in an exemplary screening assay of the present invention, the compound of interest is contacted with an isolated and purified TβRII polypeptide which is ordinarily capable of binding to TGFβ1 or TGFβ3. To the mixture of the compound and TβRII polypeptide is then added a composition containing a TβRII ligand. Detection and quantification of TβRII/TGFβ1 or TβRII/TGFβ3 complexes provides a means for determining the compound's efficacy at inhibiting (or potentiating) complex formation between the TβRII polypeptide and TGFβ1 or TGFβ3. The efficacy of the compound can be assessed by generating dose response curves from data obtained using various concentrations of the test compound. Moreover, a control assay can also be performed to provide a baseline for comparison. For example, in a control assay, isolated and a purified TGFβ1 or TGFβ3 is added to a composition containing the TβRII polypeptide, and the formation of TβRII/TGFβ1 or TβRII/TGFβ3 complex is quantitated in the absence of the test compound. It will be understood that, in general, the order in which the reactants may be admixed can be varied, and can be admixed simultaneously. Moreover, in place of purified proteins, cellular extracts and lysates may be used to render a suitable cell-free assay system.

Complex formation between the TβRII polypeptide and TGFβ1 or TGFβ3 may be detected by a variety of techniques. For instance, modulation of the formation of complexes can be quantitated using, for example, detectably labeled proteins such as radiolabeled (e.g., $^{32}$P, $^{35}$S, $^{14}$C or $^{3}$H), fluorescently labeled (e.g., FITC), or enzymatically labeled TβRII polypeptide or TGFβ1 or TGFβ3, by immunoassay, or by chromatographic detection.

In certain embodiments, the present invention contemplates the use of fluorescence polarization assays and fluorescence resonance energy transfer (FRET) assays in measuring, either directly or indirectly, the degree of interaction between a TβRII polypeptide and its binding protein. Further, other modes of detection, such as those based on optical waveguides (PCT Publication WO 96/26432 and U.S. Pat. No. 5,677,196), surface plasmon resonance (SPR), surface charge sensors, and surface force sensors, are compatible with many embodiments of the invention.

Moreover, the present invention contemplates the use of an interaction trap assay, also known as the "two hybrid assay," for identifying agents that disrupt or potentiate interaction between a TβRII polypeptide and its binding protein. See for example, U.S. Pat. No. 5,283,317; Zervos et al. (1993) Cell 72:223-232; Madura et al. (1993) J Biol Chem 268:12046-12054; Bartel et al. (1993) Biotechniques 14:920-924; and Iwabuchi et al. (1993) Oncogene 8:1693-1696). In a specific embodiment, the present invention contemplates the use of reverse two hybrid systems to identify compounds (e.g., small molecules or peptides) that dissociate interactions between a TβRII polypeptide and its binding protein. See for example, Vidal and Legrain, (1999) Nucleic Acids Res 27:919-29; Vidal and Legrain, (1999) Trends Biotechnol 17:374-81; and U.S. Pat. Nos. 5,525,490; 5,955,280; and 5,965,368.

In certain embodiments, the subject compounds are identified by their ability to interact with a TβRII or TGFβ1 or TGFβ3 polypeptide of the invention. The interaction between the compound and the TβRII or TGFβ1 or TGFβ3 polypeptide may be covalent or non-covalent. For example, such interaction can be identified at the protein level using in vitro biochemical methods, including photo-crosslinking, radiolabeled ligand binding, and affinity chromatography (Jakoby W B et al., 1974, Methods in Enzymology 46: 1). In certain cases, the compounds may be screened in a mechanism based assay, such as an assay to detect compounds which bind to a TGFβ1 or TGFβ3 or TβRII polypeptide. This may include a solid-phase or fluid-phase binding event. Alternatively, the gene encoding a TGFβ1 or TGFβ3 or TβRII polypeptide can be transfected with a reporter system (e.g., β-galactosidase, luciferase, or green fluorescent protein) into a cell and screened against the library preferably by a high-throughput screening or with individual members of the library. Other mechanism-based binding assays may be used, for example, binding assays which detect changes in free energy. Binding assays can be performed with the target fixed to a well, bead or chip or captured by an immobilized antibody or resolved by capillary electrophoresis. The bound compounds may be detected usually using colorimetric or fluorescence or surface plasmon resonance.

In certain aspects, the present invention provides methods and agents for modulating (stimulating or inhibiting) TGFβ1- or TGFβ3-mediated cell signaling. Therefore, any compound identified can be tested in whole cells or tissues, in vitro or in vivo, to confirm their ability to modulate TGFβ1 or TGFβ3 signaling. Various methods known in the art can be utilized for this purpose.

9. Exemplary Therapeutic Uses

As used herein, a therapeutic that "prevents" a disorder or condition refers to a compound that, in a statistical sample, reduces the occurrence of the disorder or condition in the treated sample relative to an untreated control sample, or delays the onset or reduces the severity of one or more symptoms of the disorder or condition relative to the untreated control sample.

The terms "treatment", "treating", "alleviation" and the like are used herein to generally mean obtaining a desired pharmacologic and/or physiologic effect, and may also be used to refer to improving, alleviating, and/or decreasing the severity of one or more symptoms of a condition being treated. The effect may be prophylactic in terms of completely or partially delaying the onset or recurrence of a disease, condition, or symptoms thereof, and/or may be therapeutic in terms of a partial or complete cure for a disease or condition and/or adverse effect attributable to the disease or condition. "Treatment" as used herein covers any treatment of a disease or condition of a mammal, particularly a human, and includes: (a) preventing the disease or condition from occurring in a subject which may be predisposed to the disease or condition but has not yet been diagnosed as having it; (b) inhibiting the disease or condition (e.g., arresting its development); or (c) relieving the disease or condition (e.g., causing regression of the disease or condition, providing improvement in one or more symptoms).

The terms "patient", "subject", or "individual" are used interchangeably herein and refer to either a human or a non-human animal. These terms include mammals, such as humans, non-human primates, laboratory animals, livestock animals (including bovines, porcines, camels, etc.), companion animals (e.g., canines, felines, other domesticated animals, etc.) and rodents (e.g., mice and rats). In particular embodiments, the patient, subject or individual is a human.

The disclosure provides methods of treating or preventing a disease or condition associated with a TGFβ superfamily member by administering to a subject an effective amount of a TβRII polypeptide, including a TβRII-Fc fusion protein of the foregoing, hereafter collectively referred to as "therapeutic agents". In some embodiments the disease or condition is associated with dysregulated TGFβ1 or TGFβ3 signaling. Also provided are methods and compositions for treating certain cardiovascular or vascular disorders. In addition, the disclosure provides methods and compositions for treating or preventing cancer. In addition, the disclosure provides methods and compositions for treating or preventing fibrotic disorders and conditions.

In particular, polypeptide therapeutic agents of the present disclosure are useful for treating or preventing chronic vascular or cardiovascular diseases. Exemplary disorders of this kind include, but are not limited to, heart disease (including myocardial disease, myocardial infarct, angina pectoris, and heart valve disease); renal disease (including chronic glomerular inflammation, diabetic renal failure, and lupus-related renal inflammation); disorders associated with atherosclerosis or other types of arteriosclerosis (including stroke, cerebral hemorrhage, subarachnoid hemorrhage, angina pectoris, and renal arteriosclerosis); thrombotic disorders (including cerebral thrombosis, thrombotic intestinal necrosis); complications of diabetes (including diabetes-related retinal disease, cataracts, diabetes-related renal disease, diabetes-related neuropathology, diabetes-related gangrene, and diabetes-related chronic infection); vascular inflammatory disorders (systemic lupus erythematosus, joint rheumatism, joint arterial inflammation, large-cell arterial inflammation, Kawasaki disease, Takayasu arteritis, Churg-Strauss syndrome, and Henoch-Schoenlein purpura); diabetic vasculopathies; and cardiac disorders such as congenital heart disease, cardiomyopathy (e.g., dilated, hypertrophic, restrictive cardiomyopathy), and congestive heart failure. Exemplary disorders further include, but are not limited to, hereditary hemorrhagic telangiectasia (HHT), Marfan syndrome, Loeys-Dietz syndrome, familial thoracic aortic aneurysm syndrome, arterial tortuosity syndrome, pre-eclampsia, and restenosis.

The TβRII polypeptide can be administered to the subject alone, or in combination with one or more agents or therapeutic modalities, e.g., therapeutic agents, which are useful for treating TGFβ associated cardiovascular disorders and/or conditions. In certain embodiments, the second agent or therapeutic modality is chosen from one or more of: angioplasty, beta blockers, anti-hypertensives, cardiotonics, anti-thrombotics, vasodilators, hormone antagonists, endothelin antagonists, calcium channel blockers, phosphodiesterase inhibitors, angiotensin type 2 antagonists and/or cytokine blockers/inhibitors In particular, polypeptide therapeutic agents of the present disclosure are useful for treating or preventing a cancer (tumor). The terms "cancer" and "cancerous" refer to or describe, the physiological condition in mammals that is typically characterized by unregulated cell growth/proliferation. Examples of cancer, or neoplastic disorders, include but are not limited to, carcinoma, lymphoma, blastoma, sarcoma, and leukemia. More particular examples of such cancers include squamous cell cancer, cancer of the peritoneum, hepatocellular cancer, gastrointestinal cancer, pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney cancer, prostate cancer, vulval cancer, thyroid cancer, hepatic carcinoma, stomach cancer, intestinal cancer, skin cancer, bone cancer, gastric cancer, melanoma, and various types of head and neck cancer, including squamous cell head and neck cancer. Other examples of neoplastic disorders and related conditions include esophageal carcinomas, thecomas, arrhenoblastomas, endometrial hyperplasia, endometriosis, fibrosarcomas, choriocarcinoma, nasopharyngeal carcinoma, laryngeal carcinomas, hepatoblastoma, Kaposi's sarcoma, skin carcinomas, hemangioma, cavernous hemangioma, hemangioblastoma, retinoblastoma, astrocytoma, glioblastoma, Schwannoma, oligodendroglioma, medulloblastoma, neuroblastomas, rhabdomyosarcoma, osteogenic sarcoma, leiomyosarcomas, urinary tract carcinomas, Wilm's tumor, renal cell carcinoma, prostate carcinoma, abnormal vascular proliferation associated with phakomatoses, and Meigs' syndrome. A cancer that is particularly amenable to treatment with the therapeutic agents described herein may be characterized by one or more of the following: the cancer has elevated TβRII levels detectable in the tumor or the serum, increased TGFβ1 or TGFβ3 expression levels or biological activity, is metastatic or at risk of becoming metastatic, or any combination thereof.

In certain embodiments of such methods, one or more polypeptide therapeutic agents can be administered, together (simultaneously) or at different times (sequentially). In addition, polypeptide therapeutic agents can be administered with another type of compounds for treating cancer or for inhibiting angiogenesis.

In certain embodiments, the subject methods of the disclosure can be used alone. Alternatively, the subject methods may be used in combination with other conventional anti-cancer therapeutic approaches directed to treatment or prevention of proliferative disorders (e.g., tumor). For example, such methods can be used in prophylactic cancer prevention, prevention of cancer recurrence and metastases after surgery, and as an adjuvant of other conventional cancer therapy. The present disclosure recognizes that the effectiveness of conventional cancer therapies (e.g., chemotherapy, radiation therapy, phototherapy, immunotherapy, and surgery) can be enhanced through the use of a subject polypeptide therapeutic agent.

A wide array of conventional compounds have been shown to have anti-neoplastic or anti-cancer activities. These compounds have been used as pharmaceutical agents in chemotherapy to shrink solid tumors, prevent metastases and further growth, or decrease the number of malignant cells in leukemic or bone marrow malignancies. Although chemotherapy has been effective in treating various types of malignancies, many anti-neoplastic compounds induce undesirable side effects. It has been shown that when two or more different treatments are combined, the treatments may work synergistically and allow reduction of dosage of each of the treatments, thereby reducing the detrimental side effects exerted by each compound at higher dosages. In other instances, malignancies that are refractory to a treatment may respond to a combination therapy of two or more different treatments.

When a therapeutic agent disclosed herein is administered in combination with another conventional anti-neoplastic agent, either concomitantly or sequentially, such therapeutic agent may enhance the therapeutic effect of the anti-neoplastic agent or overcome cellular resistance to such anti-neoplastic agent. This allows decrease of dosage of an anti-neoplastic agent, thereby reducing the undesirable side effects, or restores the effectiveness of an anti-neoplastic agent in resistant cells.

According to the present disclosure, the polypeptide therapeutic agents described herein may be used in combination with other compositions and procedures for the treatment of diseases. For example, a tumor may be treated conventionally with surgery, radiation or chemotherapy combined with the TβRII polypeptide, and then the TβRII polypeptide may be subsequently administered to the patient to extend the dormancy of micrometastases and to stabilize any residual primary tumor.

In certain aspects of the invention, other therapeutic agents useful for combination tumor therapy with a TβRII polypeptide include other cancer therapies: e.g., surgery, cytotoxic agents, radiological treatments involving irradiation or administration of radioactive substances, chemotherapeutic agents, anti-hormonal agents, growth inhibitory agents, anti-neoplastic compositions, and treatment with anti-cancer agents listed herein and known in the art, or combinations thereof.

The term "cytotoxic agent" as used herein refers to a substance that inhibits or prevents the function of cells and/or causes destruction of cells. The term is intended to include radioactive isotopes (e.g., $At^{211}$, $I^{131}$, $I^{125}$, $Y^{90}$, $Re^{186}$, $Re^{188}$, $Sm^{153}$, $Bi^{212}$, $P^{32}$ and radioactive isotopes of Lu), chemotherapeutic agents e.g. methotrexate, adriamicin, vinca alkaloids (vincristine, vinblastine, etoposide), doxorubicin, melphalan, mitomycin C, chlorambucil, daunorubicin or other intercalating agents, enzymes and fragments thereof such as nucleolytic enzymes, antibiotics, and toxins such as small molecule toxins or enzymatically active toxins of bacterial, fungal, plant or animal origin, including fragments and/or variants thereof, and the various antitumor or anticancer agents disclosed below. Other cytotoxic agents are described below. A tumoricidal agent causes destruction of tumor cells.

A "chemotherapeutic agent" is a chemical compound useful in the treatment of cancer. Examples of chemotherapeutic agents include alkylating agents such as thiotepa and CYTOXAN® cyclophosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); delta-9-tetrahydrocannabinol (dronabinol, MARINOL®); beta-lapachone; lapachol; colchicines; betulinic acid; a camptothecin (including the synthetic analogue topotecan (HYCAMTIN®), CPT-11 (irinotecan, CAMPTOSAR®), acetylcamptothecin, scopolectin, and 9-aminocamptothecin); bryostatin; callystatin; CC-1065 (including its adozelesin, carzelesin and bizelesin synthetic analogues); podophyllotoxin; podophyllinic acid; teniposide; cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cyclophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gammaII and calicheamicin omegaII (see, e.g., Agnew, Chem Intl. Ed. Engl., 33: 183-186 (1994)); dynemicin, including dynemicin A; an esperamicin; as well as neocarzinostatin chromophore and related chromoprotein enediyne antiobiotic chromophores), aclacinomysins, actinomycin, authramycin, azaserine, bleomycins, cactinomycin, carabicin, carminomycin, carzinophilin, chromomycinis, dactinomycin, daunorubicin, detorubicin, 6-diazo-5-oxo-L-norleucine, ADRIAMYCIN® doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as folinic acid; aceglatone; aldophosphamide glycoside; aminolevulinic acid; eniluracil; amsacrine; bestrabucil; bisantrene; edatraxate; demecolcine; diaziquone; elfornithine; elliptinium acetate; an epothilone; etoglucid; gallium nitrate; hydroxyurea; lentinan; lonidamine; maytansinoids such as maytansine and ansamitocins; mitoguazone; mitoxantrone; mopidanmol; nitraerine; pentostatin; phenamet; pirarubicin; losoxantrone; 2-ethylhydrazide; procarbazine; PSK® polysaccharide complex (JHS Natural Products, Eugene, Oreg.); razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine (ELDISINE®, FILDESIN®); dacarbazine; mannomustine; mitobronitol; mitolactol; pipobroman; gacytosine; arabinoside ("Ara-C"); thiotepa; taxoids, e.g., TAXOL® paclitaxel (Bristol-Myers Squibb Oncology, Princeton, N.J.), ABRAXANE™ Cremophor-free, albumin-engineered nanoparticle formulation of paclitaxel (American Pharmaceutical Partners, Schaumberg, Ill.), and TAXOTERE® doxetaxel (Rhone-Poulenc Rorer, Antony, France); chlorambucil; gemcitabine (GEMZAR®); 6-thioguanine; mercaptopurine; methotrexate; platinum analogs such as cisplatin and carboplatin; vinblastine (VELBAN®); platinum; etoposide (VP-16); ifosfamide; mitoxantrone; vincristine (ONCOVIN®); oxaliplatin; leucovovin; vinorelbine (NAVELBINE®); novantrone; edatrexate; daunomycin; aminopterin; ibandronate; topoisomerase inhibitor RFS 2000; difluoromethylornithine (DMFO); retinoids such as retinoic acid; capecitabine (XELODA®); pharmaceutically acceptable salts, acids or derivatives of any of the above; as well as combinations of two or more of the above such as CHOP, an abbreviation for a combined therapy of cyclophosphamide, doxorubicin, vincristine, and prednisolone, and FOLFOX, an abbreviation for a treatment regimen with oxaliplatin (ELOXATIN™) combined with 5-FU and leucovovin.

Also included in this definition are anti-hormonal agents that act to regulate, reduce, block, or inhibit the effects of hormones that can promote the growth of cancer, and are often in the form of systemic, or whole-body treatment. They may be hormones themselves. Examples include anti-estrogens and selective estrogen receptor modulators (SERMs), including, for example, tamoxifen (including NOLVADEX® tamoxifen), EVISTA® raloxifene, droloxifene, 4-hydroxytamoxifen, trioxifene, keoxifene, LY1 17018, onapristone, and FARESTON® toremifene; anti-progesterones; estrogen receptor down-regulators (ERDs); agents that function to suppress or shut down the ovaries, for example, luteinizing hormone-releasing hormone (LHRH) agonists such as LUPRON® and ELIGARD® leuprolide acetate, goserelin acetate, buserelin acetate and tripterelin; other anti-androgens such as flutamide, nilutamide and bicalutamide; and aromatase inhibitors that inhibit the enzyme aromatase, which regulates estrogen production in the adrenal glands, such as, for example, 4(5)-imidazoles, aminoglutethimide, MEGASE® megestrol acetate, AROMASIN® exemestane, formestane, fadrozole, RIVIS OR® vorozole, FEMARA® letrozole, and ARIMIDEX® anastrozole. In addition, such definition of chemotherapeutic agents includes bisphosphonates such as clodronate (for example, BONEFOS® or OSTAC®), DIDROC AL® etidronate, NE-58095, ZOMET zoledronic acid/zoledronate, FOSAMAX® alendronate, AREDIA® pamidronate, SKELID® tiludronate, or ACTONEL® risedronate; as well as troxacitabine (a 1,3-dioxolane nucleoside cytosine analog); antisense oligonucleotides, particularly those that inhibit expression of genes in signaling pathways implicated in aberrant cell proliferation, such as, for example, PKC-alpha, Raf, H-Ras, and epidermal growth factor receptor (EGF-R); vaccines such as THERATOPE® vaccine and gene therapy vaccines, for example, ALLOVECTIN® vaccine, LEUVECTIN® vaccine, and VAXID® vaccine; LURTOTE- CAN® topoisomerase 1 inhibitor; ABARELIX® rmRH; lapatinib ditosylate (an ErbB-2 and EGFR dual tyrosine kinase small-molecule inhibitor also known as GW572016); and pharmaceutically acceptable salts, acids or derivatives of any of the above.

A "growth inhibitory agent" when used herein refers to a compound or composition which inhibits growth of a cell either in vitro or in vivo. Thus, the growth inhibitory agent may be one which significantly reduces the percentage of cells in S phase. Examples of growth inhibitory agents include agents that block cell cycle progression (at a place other than S phase), such as agents that induce Gl arrest and M-phase arrest. Classical M-phase blockers include the vincas (vincristine and vinblastine), taxanes, and topoisomerase II inhibitors such as doxorubicin, epirubicin, daunorubicin, etoposide, and bleomycin. Those agents that arrest Gl also spill over into S-phase arrest, for example, DNA alkylating agents such as tamoxifen, prednisone, dacarbazine, mechlorethamine, cisplatin, methotrexate, 5-fluorouracil, and ara-C. Further information can be found in The Molecular Basis of Cancer, Mendelsohn and Israel, eds., Chapter 1, entitled "Cell cycle regulation, oncogenes, and antineoplastic drugs" by Murakami et al. (WB Saunders: Philadelphia, 1995), especially p. 13. The taxanes (paclitaxel and docetaxel) are anticancer drugs both derived from the yew tree. Docetaxel (TAXOTERE®, Rhone-Poulenc Rorer), derived from the European yew, is a semisynthetic analogue of paclitaxel (TAXOL®, Bristol-Myers Squibb). Paclitaxel and docetaxel promote the assembly of microtubules from tubulin dimers and stabilize microtubules by preventing depolymerization, which results in the inhibition of mitosis in cells.

In still other embodiments, TβRII polypeptides may be useful in the treatment or prevention of fibrosis. As used herein, the term "fibrosis" refers to the aberrant formation or development of excess fibrous connective tissue by cells in an organ or tissue. Although processes related to fibrosis can occur as part of normal tissue formation or repair, dysregulation of these processes can lead to altered cellular composition and excess connective tissue deposition that progressively impairs to tissue or organ function. The formation of fibrous tissue can result from a reparative or reactive process. Fibrotic disorders or conditions include, but are not limited to, fibroproliferative disorders associated with vascular diseases, such as cardiac disease, cerebral disease, and peripheral vascular disease, as well as tissues and organ systems including the heart, skin, kidney, peritoneum, gut, and liver (as disclosed in, e.g., Wynn, 2004, Nat Rev 4:583-594, incorporated herein by reference). Exemplary disorders that can be treated include, but are not limited to, renal fibrosis, including nephropathies associated with injury/fibrosis, e.g., chronic nephropathies associated with diabetes (e.g., diabetic nephropathy), lupus, scleroderma, glomerular nephritis, focal segmental glomerular sclerosis, and IgA nephropathy; gut fibrosis, e.g., scleroderma, and radiation-induced gut fibrosis; liver fibrosis, e.g., cirrhosis, alcohol-induced liver fibrosis, biliary duct injury, primary biliary cirrhosis, infection or viral-induced liver fibrosis, congenital hepatic fibrosis and autoimmune hepatitis; and other fibrotic conditions, such as cystic fibrosis, endomyocardial fibrosis, mediastinal fibrosis, sarcoidosis, scleroderma, spinal cord injury/fibrosis, myelofibrosis, vascular restenosis, atherosclerosis, injection fibrosis (which can occur as a complication of intramuscular injections, especially in children), endomyocardial fibrosis, retroperitoneal fibrosis, and nephrogenic systemic fibrosis.

As used herein, the terms "fibrotic disorder", "fibrotic condition," and "fibrotic disease," are used interchangeably to refer to a disorder, condition or disease characterized by fibrosis. Examples of fibrotic disorders include, but are not limited to lupus, sclerotic disorders (e.g., scleroderma, atherosclerosis, and systemic scleroisis including, e.g., diffuse systemic sclerosis and progressive systemic sclerosis), vascular fibrosis, pancreatic fibrosis, liver fibrosis (e.g., cirrhosis), renal fibrosis, musculoskeletal fibrosis, cardiac fibrosis (e.g., endomyocardial fibrosis, idiopathic myocardiopathy), skin fibrosis (e.g., scleroderma, post-traumatic, operative cutaneous scarring, keloids and cutaneous keloid formation), eye fibrosis (e.g., glaucoma, sclerosis of the eyes, conjunctival and corneal scarring, and pterygium), myelofibrosis, chronic graft-versus-host disease, Peyronie's disease, post-cystoscopic urethral stenosis, idiopathic and pharmacologically induced retroperitoneal fibrosis, mediastinal fibrosis, proliferative fibrosis, neoplastic fibrosis, Dupuytren's disease, strictures, neural scarring, dermal scarring, idiopathic pulmonary fibrosis and radiation induced fibrosis.

In some embodiments, any of the polypeptides disclosed herein (e.g., a polypeptide having the amino acid sequence of any one of SEQ ID NOs: 13 and 50-56) may be used, alone or in combination with one or more supportive therapies or active agents, to treat, prevent, or reduce the progression rate and/or severity of an interstitial lung disease (e.g., idiopathic pulmonary fibrosis). In some embodiments, the interstitial lung disease is pulmonary fibrosis. In some embodiments, the interstitial lung disease is caused by any one of the following: silicosis, asbestosis, berylliosis, hypersensitivity pneumonitis, drug use (e.g., antibiotics, chemotherapeutic drugs, antiarrhythmic agents, statins), systemic sclerosis, polymyositis, dermatomyositis, systemic lupus erythematosus, rheumatoid arthritis, an infection (e.g., atypical pneumonia, pneumocystis pneumonia, tuberculosis, *Chlamydia trachomatis*, and/or respiratory syncytial virus), lymphangitic carcinomatosis, cigarette smoking, or developmental disorders. In some embodiments, the interstitial lung disease is idiopathic (e.g., sarcoidosis, idiopathic pulmonary fibrosis, Hamman-Rich syndrome, and/or antisynthetase syndrome). In particular embodiments, the interstitial lung disease is idiopathic pulmonary fibrosis. In some embodiments, the treatment for idiopathic pulmonary fibrosis is administered in combination with an additional therapeutic agent. In some embodiments, the additional therapeutic agent is selected from the group consisting of: pirfenidone, N-acetylcysteine, prednisone, azathioprine, nintedanib, derivatives thereof and combinations thereof.

In some embodiments, any of the polypeptides disclosed herein (e.g., a polypeptide having the amino acid sequence of any one of SEQ ID NOs: 13 and 50-56) may be used, alone or in combination with one or more supportive therapies or active agents, to treat, prevent, or reduce the progression rate and/or severity of a kidney-associated disease or condition. As used herein, "kidney-associated disease or condition" can refer to any disease, disorder, or condition that affects the kidneys or the renal system. Examples of kidney-associated diseases or conditions include, but are not limited to, chronic kidney diseases (or failure), acute kidney diseases (or failure), primary kidney diseases, non-diabetic kidney diseases, glomerulonephritis, interstitial nephritis, diabetic kidney diseases, diabetic nephropathy, glomerulosclerosis, rapid progressive glomerulonephritis, renal fibrosis, Alport syndrome, IDDM nephritis, mesangial proliferative glomerulonephritis, membranoproliferative glomerulonephritis, crescentic glomerulonephritis, renal interstitial fibrosis, focal segmental glomerulosclerosis, membranous nephropathy, minimal change disease, pauci-immune rapid progressive glomerulonephritis, IgA nephropathy, polycystic kidney disease, Dent's disease, nephrocytinosis, Heymann nephritis, autosomal dominant (adult) polycystic kidney disease, autosomal recessive (childhood) polycystic kidney disease, acute kidney injury, nephrotic syndrome, renal ischemia, podocyte diseases or disorders, proteinuria, glomerular diseases, membranous glomerulonephritis, focal segmental glomerulonephritis, pre-eclampsia, eclampsia, kidney lesions, collagen vascular diseases, benign orthostatic (postural) proteinuria, IgM nephropathy, membranous nephropathy, sarcoidosis, diabetes mellitus, kidney damage due to drugs, Fabry's disease, aminoaciduria, Fanconi syndrome, hypertensive nephrosclerosis, interstitial nephritis, Sickle cell disease, hemoglobinuria, myoglobinuria, Wegener's Granulomatosis, Glycogen Storage Disease Type 1, chronic kidney disease, chronic renal failure, low Glomerular Filtration Rate (GFR), nephroangiosclerosis, lupus nephritis, ANCA-positive pauci-immune crescentic glomerulonephritis, chronic allograft nephropathy, nephrotoxicity, renal toxicity, kidney necrosis, kidney damage, glomerular and tubular injury, kidney dysfunction, nephritic syndrome, acute renal failure, chronic renal failure, proximal tubal dysfunction, acute kidney transplant rejection, chronic kidney transplant rejection, non-IgA mesangioproliferative glomerulonephritis, postinfectious glomerulonephritis, vasculitides with renal involvement of any kind, any hereditary renal disease, any interstitial nephritis, renal transplant failure, kidney cancer, kidney disease associated with other conditions (e.g., hypertension, diabetes, and autoimmune disease), Dent's disease, nephrocytinosis, Heymann nephritis, a primary kidney disease, a collapsing glomerulopathy, a dense deposit disease, a cryoglobulinemia-associated glomerulonephritis, an Henoch-Schonlein disease, a postinfectious glomerulonephritis, a bacterial endocarditis, a microscopic polyangitis, a Churg-Strauss syndrome, an anti-GBM-antibody mediated glomerulonephritis, amyloidosis, a monoclonal immunoglobulin deposition disease, a fibrillary glomerulonephritis, an immunotactoid glomerulopathy, ischemic tubular injury, a medication-induced tubulo-interstitial nephritis, a toxic tubulo-interstitial nephritis, an infectious tubulo-interstitial nephritis, a bacterial pyelonephritis, a viral infectious tubulo-interstitial nephritis which results from a polyomavirus infection or an HIV infection, a metabolic-induced tubulo-interstitial disease, a mixed connective disease, a cast nephropathy, a crystal nephropathy which may results from urate or oxalate or drug-induced crystal deposition, an acute cellular tubulo-interstitial allograft rejection, a tumoral infiltrative disease which results from a lymphoma or a post-transplant lymphoproliferative disease, an obstructive disease of the kidney, vascular disease, a thrombotic microangiopathy, a nephroangiosclerosis, an atheroembolic disease, a mixed connective tissue disease, a polyarteritis nodosa, a calcineurin-inhibitor induced-vascular disease, an acute cellular vascular allograft rejection, an acute humoral allograft rejection, early renal function decline (ERFD), end stage renal disease (ESRD), renal vein thrombosis, acute tubular necrosis, acute interstitial nephritis, established chronic kidney disease, renal artery stenosis, ischemic nephropathy, uremia, drug and toxin-induced chronic tubulointerstitial nephritis, reflux nephropathy, kidney stones, Goodpasture's syndrome, normocytic normochromic anemia, renal anemia, diabetic chronic kidney disease, IgG4-related disease, von Hippel-Lindau syndrome, tuberous sclerosis, nephronophthisis, medullary cystic kidney disease, renal cell carcinoma, adenocarcinoma, nephroblastoma, lymphoma, leukemia, hyposialylation disorder, chronic cyclosporine nephropathy, renal reperfusion injury, renal dysplasia, azotemia, bilateral arterial occlusion, acute uric acid nephropathy, hypovolemia, acute bilateral obstructive uropathy, hypercalcemic nephropathy, hemolytic uremic syndrome, acute urinary retention, malignant nephrosclerosis, postpartum glomerulosclerosis, scleroderma, non-Goodpasture's anti-GBM disease, microscopic polyarteritis nodosa, allergic granulomatosis, acute radiation nephritis, post-streptococcal glomerulonephritis, Waldenstrom's macroglobulinemia, analgesic nephropathy, arteriovenous fistula, arteriovenous graft, dialysis, ectopic kidney, medullary sponge kidney, renal osteodystrophy, solitary kidney, hydronephrosis, microalbuminuria, uremia, haematuria, hyperlipidemia, hypoalbuminaemia, lipiduria, acidosis, hyperkalemia, and edema.

In some embodiments, any of the polypeptides disclosed herein (e.g., a polypeptide having the amino acid sequence of any one of SEQ ID NOs: 13 and 50-56) may be used, alone or in combination with one or more supportive therapies or active agents, to treat, prevent, or reduce the progression rate and/or severity of chronic kidney disease (e.g., tissue damage, inflammation, and/or fibrosis). Chronic kidney disease (CKD), also known as chronic renal disease, is a progressive loss in renal function over a period of months or years. The symptoms of worsening kidney function may include feeling generally unwell and experiencing a reduced appetite. Often, chronic kidney disease is diagnosed as a result of screening of people known to be at risk of kidney problems, such as those with high blood pressure or diabetes and those with a blood relative with CKD. This disease may also be identified when it leads to one of its recognized complications, such as cardiovascular disease, anemia, or pericarditis. Recent professional guidelines classify the severity of CKD in five stages, with stage 1 being the mildest and usually causing few symptoms and stage 5 being a severe illness with poor life expectancy if untreated. Stage 5 CKD is often called end-stage kidney disease, end-stage renal disease, or end-stage kidney failure, and is largely synonymous with the now outdated terms chronic renal failure or chronic kidney failure; and usually means the patient requires renal replacement therapy, which may involve a form of dialysis, but ideally constitutes a kidney transplant. CKD is initially without specific symptoms and is generally only detected as an increase in serum creatinine or protein in the urine. As the kidney function decreases, various symptoms may manifest as described below. Blood pressure may be increased due to fluid overload and production of vasoactive hormones created by the kidney via the renin-angiotensin system, increasing one's risk of developing hypertension and/or suffering from congestive heart failure. Urea may accumulate, leading to azotemia and ultimately uremia (symptoms ranging from lethargy to pericarditis and encephalopathy). Due to its high systemic circulation, urea is excreted in eccrine sweat at high concentrations and crystallizes on skin as the sweat evaporates ("uremic frost"). Potassium may accumulate in the blood (hyperkalemia with a range of symptoms including malaise and potentially fatal cardiac arrhythmias). Hyperkalemia usually does not develop until the glomerular filtration rate falls to less than 20-25 ml/min/1.73 m2, at which point the kidneys have decreased ability to excrete potassium. Hyperkalemia in CKD can be exacerbated by acidemia (which leads to extracellular shift of potassium) and from lack of insulin. Erythropoietin synthesis may be decreased causing anemia. Fluid volume overload symptoms may occur, ranging from mild edema to life-threatening pulmonary edema. Hyperphosphatemia, due to reduced phosphate excretion, may occur generally following the decrease in glomerular filtration. Hyperphosphatemia is associated with increased cardiovascular risk, being a direct stimulus to vascular calcification. Hypocalcemia may manifest, which is generally caused by stimulation of fibroblast growth factor-23. Osteocytes are responsible for the increased production of FGF23, which is a potent inhibitor of the enzyme 1-alpha-hydroxylase (responsible for the conversion of 25-hydroxycholecalciferol into 1,25 dihydroxyvitamin D3). Later, this progresses to secondary hyperparathyroidism, renal osteodystrophy, and vascular calcification that further impairs cardiac function. Metabolic acidosis (due to accumulation of sulfates, phosphates, uric acid etc.) may occur and cause altered enzyme activity by excess acid acting on enzymes; and also increased excitability of cardiac and neuronal membranes by the promotion of hyperkalemia due to excess acid (acidemia). Acidosis is also due to decreased capacity to generate enough ammonia from the cells of the proximal tubule. Iron deficiency anemia, which increases in prevalence as kidney function decreases, is especially prevalent in those requiring haemodialysis. It is multifactoral in cause, but includes increased inflammation, reduction in erythropoietin, and hyperuricemia leading to bone marrow suppression. People with CKD suffer from accelerated atherosclerosis and are more likely to develop cardiovascular disease than the general population. Patients afflicted with CKD and cardiovascular disease tend to have significantly worse prognoses than those suffering only from the latter. In some embodiments, the chronic kidney disease is a chronic kidney disease mineral bone disorder, a broad syndrome of interrelated skeletal, cardiovascular, and mineral-metabolic disorders arising from kidney disease. CKD-MBD encompasses various skeletal pathologies often referred to as renal osteodystrophy (ROD), which is a preferred embodiment for treatment with any of the polypeptides disclosed herein, or combinations with one or more supportive therapies or active agents. Depending on the relative contribution of different pathogenic factors, ROD is manifested as diverse pathologic patterns of bone remodeling (Hruska et al., 2008, Chronic kidney disease mineral bone disorder (CKD-MBD); in Rosen et al. (ed) Primer on the Metabolic Bone Diseases and Disorders of Mineral Metabolism, 7th ed. American Society for Bone and Mineral Research, Washington D.C., pp 343-349). At one end of the spectrum is ROD with uremic osteodystrophy and low bone turnover, characterized by a low number of active remodeling sites, profoundly suppressed bone formation, and low bone resorption. At the other extreme is ROD with hyperparathyroidism, high bone turnover, and osteitis fibrosa.

In certain aspects, any of the polypeptides (e.g., a polypeptide having the amino acid sequence of SEQ ID NOs: 13 and 50-56) disclosed herein may be used, alone or in combination with one or more supportive therapies or active agents, to treat, prevent, or reduce the progression rate and/or severity of myelofibrosis (e.g., primary myelofibrosis, post-polycythemia vera myelofibrosis, and post-essential thrombocythemia myelofibrosis). In particular, ActRIIB antagonists may be used, alone or in combination with one or more supportive therapies or active agents, to treat, prevent, or reduce the progression rate and/or severity of one or more complications of myelofibrosis including, for example, ineffective hematopoiesis, anemia, inflammation, fibrosis (e.g., bone marrow fibrosis, spleen fibrosis, and liver fibrosis), pancytopenia, thrombocytopenia, extramedullary hematopoiesis (e.g., splenic extramedullary hematopoiesis, hepatic extramedullary hematopoiesis, pulmonary extramedullary hematopoiesis, and lymphatic extramedullary hematopoiesis), hepatomegaly, splenomegaly, osteosclerosis, osteomyelofibrosis, poikilocytosis, fatigue, weight loss, night sweats, fever, pruritus, bone pain, early satiety, abdominal pain or discomfort, arthralgias, myalgias, parasthesias, cachexia, splenic infarct, and bleeding.

As used herein, inhibition of the fibrotic response of a cell, includes, but is not limited to the inhibition of the fibrotic response of one or more cells within the liver (or liver tissue); one or more cells within the kidney (or renal tissue); one or more cells within muscle tissue; one or more cells within the heart (or cardiac tissue); one or more cells within the pancreas; one or more cells within the skin; one or more cells within the bone, one or more cells within the vasculature, one or more stem cells, or one or more cells within the eye.

In some embodiments, any of the TβRII polypeptides of the disclosure may be used for treating an autoimmune disease or disorder. In some embodiments, the autoimmune disease or disorder is selected from the group consisting of: spondyloarthropathies; ankylosing spondylitis, arthritis, psoriatic arthritis/spondylitis, enteropathic arthritis, reactive arthritis, Reiter's syndrome, undifferentiated spondyloarthropathies; reactive arthritis, rheumatism, inflammatory bowel syndrome, Crohns Disease, rheumatoid arthritis, rheumatoid spondylitis, osteoarthritis, gouty arthritis, allergy, multiple sclerosis, autoimmune diabetes, autoimmune uveitis and nephrotic syndrome.

In some embodiments, any of the TβRII polypeptides of the disclosure may be used for treating a metabolic disorder. In some embodiments, the metabolic disorder is obesity or diabetes (e.g., Type I or Type II diabetes), fatty liver disease, diabetic neuropathy, peripheral neuropathy, diabetic retinopathy, diabetic ulcerations, retinopathy ulcerations, diabetic macrovasculopathy.

In some embodiments, any of the TβRII polypeptides of the disclosure may be used for treating an infectious disease or following an organ or tissue transplantation.

In some embodiments, any of the TβRII polypeptides of the disclosure may be used for treating chronic obstructive pulmonary disease (COPD), chronic obstructive airway disorder, idiopathic pulmonary fibrosis and/or asthma. In part, the disclosure also relates to methods of treating pulmonary hypertension (e.g., pulmonary arterial hypertension) comprising administering to a patient in need thereof an effective amount of a TβRII polypeptide (e.g., a polypeptide comprising the amino acid sequence of any one of SEQ ID NOs: 13 and 50-56). In some embodiments, the disclosure contemplates methods of treating one or more complications of pulmonary hypertension (e.g., smooth muscle and/or endothelial cell proliferation in the pulmonary artery, angiogenesis in the pulmonary artery, dyspnea, chest pain, pulmonary vascular remodeling, right ventricular hypertrophy, and pulmonary fibrosis) comprising administering to a patient in need thereof an effective amount of a TβRII polypeptide. In some embodiments, the disclosure contemplates methods of preventing one or more complications of pulmonary hypertension comprising administering to a patient in need thereof an effective amount of a TβRII polypeptide. In some embodiments, the disclosure contemplates methods of reducing the progression rate of pulmonary hypertension comprising administering to a patient in need thereof an effective amount of a TβRII polypeptide. In some embodiments, the disclosure contemplates methods of reducing the progression rate of one or more complications of pulmonary hypertension comprising administering to a patient in need thereof an effective amount of a TβRII polypeptide. In some embodiments, the disclosure contemplates methods of reducing the severity of pulmonary hypertension comprising administering to a patient in need thereof an effective amount of a TβRII polypeptide. In some embodiments, the disclosure contemplates methods of reducing the severity of one or more complications of pulmonary hypertension comprising administering to a patient in need thereof an effective amount of a TβRII polypeptide. Optionally, methods disclosed herein for treating, preventing, or reducing the progression rate and/or severity of pulmonary hypertension, particularly treating, preventing, or reducing the progression rate and/or severity of one or more complications of pulmonary hypertension, may further comprise administering to the patient one or more supportive therapies or additional active agents for treating pulmonary hypertension.

The present invention contemplates the use of TβRII polypeptides in combination with one or more other therapeutic modalities. Thus, in addition to the use of TβRII polypeptides, one may also administer to the subject one or more "standard" therapies for treating fibrotic disorders. For example, the TβRII polypeptides can be administered in combination with (i.e., together with) cytotoxins, immunosuppressive agents, radiotoxic agents, and/or therapeutic antibodies. Particular co-therapeutics contemplated by the present invention include, but are not limited to, steroids (e.g., corticosteroids, such as Prednisone), immune-suppressing and/or anti-inflammatory agents (e.g., gamma-interferon, cyclophosphamide, azathioprine, methotrexate, penicillamine, cyclosporine, colchicine, antithymocyte globulin, mycophenolate mofetil, and hydroxychloroquine), cytotoxic drugs, calcium channel blockers (e.g., nifedipine), angiotensin converting enzyme inhibitors (ACE) inhibitors, para-aminobenzoic acid (PABA), dimethyl sulfoxide, transforming growth factor beta (TGFβ) inhibitors, interleukin-5 (IL-5) inhibitors, and pan caspase inhibitors.

Additional anti-fibrotic agents that may be used in combination with TβRII polypeptides include, but are not limited to, lectins (as described in, for example, U.S. Pat. No. 7,026,283, the entire contents of which is incorporated herein by reference), as well as the anti-fibrotic agents described by Wynn et al (2007, J Clin Invest 117:524-529, the entire contents of which is incorporated herein by reference). For example, additional anti-fibrotic agents and therapies include, but are not limited to, various anti-inflammatory/immunosuppressive/cytotoxic drugs (including colchicine, azathioprine, cyclophosphamide, prednisone, thalidomide, pentoxifylline and theophylline), TGFβ signaling modifiers (including relaxin, SMAD7, HGF, and BMP7, as well as TGFβ1, TβRI, EGR-I, and CTGF inhibitors), cytokine and cytokine receptor antagonists (inhibitors of IL-1β, IL-5, IL-6, IL-13, IL-21, IL-4R, IL-13Rα1, GM-CSF, TNF-α, oncostatin M, W1SP-I, and PDGFs), cytokines and chemokines (IFN-γ, IFN-α/β, IL-12, IL-10, HGF, CXCL10, and CXCL11), chemokine antagonists (inhibitors of CXCL1, CXCL2, CXCL12, CCL2, CCL3, CCL6, CCL17, and CCL18), chemokine receptor antagonists (inhibitors of CCR2, CCR3, CCR5, CCR7, CXCR2, and CXCR4), TLR antagonists (inhibitors of TLR3, TLR4, and TLR9), angiogenesis antagonists (VEGF-specific antibodies and adenosine deaminase replacement therapy), antihypertensive drugs (beta blockers and inhibitors of ANG 11, ACE, and aldosterone), vasoactive substances (ET-1 receptor antagonists and bosetan), inhibitors of the enzymes that synthesize and process collagen (inhibitors of prolyl hydroxylase), B cell antagonists (rituximab), integrin/adhesion molecule antagonists (molecules that block α1β1 and αvβ6 integrins, as well as inhibitors of integrin-linked kinase, and antibodies specific for ICAM-I and VCAM-I), proapoptotic drugs that target myofibroblasts, MMP inhibitors (inhibitors of MMP2, MMP9, and MMP12), and T1MP inhibitors (antibodies specific for TIMP-1).

The TβRII polypeptide and the co-therapeutic agent or co-therapy can be administered in the same formulation or separately. In the case of separate administration, the TβRII polypeptide can be administered before, after, or concurrently with the co-therapeutic or co-therapy. One agent may precede or follow administration of the other agent by intervals ranging from minutes to weeks. In embodiments where two or more different kinds of therapeutic agents are applied separately to a subject, one would generally ensure that a significant period of time did not expire between the time of each delivery, such that these different kinds of agents would still be able to exert an advantageously combined effect on the target tissues or cells.

10. Pharmaceutical Compositions

The therapeutic agents described herein (e.g., TβRII fusion polypeptides) may be formulated into pharmaceutical compositions. Pharmaceutical compositions for use in accordance with the present disclosure may be formulated in conventional manner using one or more physiologically acceptable carriers or excipients. Such formulations will generally be substantially pyrogen-free, in compliance with most regulatory requirements.

In certain embodiments, the therapeutic method of the disclosure includes administering the composition systemically, or locally as an implant or device. When administered, the therapeutic composition for use in this disclosure is in a pyrogen-free, physiologically acceptable form. Therapeutically useful agents other than the TβRII signaling antagonists which may also optionally be included in the composition as described above, may be administered simultaneously or sequentially with the subject compounds (e.g., TβRII polypeptides) in the methods disclosed herein.

Typically, protein therapeutic agents disclosed herein will be administered parentally, and particularly intravenously or subcutaneously. Pharmaceutical compositions suitable for parenteral administration may comprise one or more TβRII polypeptides in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents. Examples of suitable aqueous and nonaqueous carriers which may be employed in the pharmaceutical compositions of the disclosure include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

The compositions and formulations may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration Further, the composition may be encapsulated or injected in a form for delivery to a target tissue site. In certain embodiments, compositions of the present invention may include a matrix capable of delivering one or more therapeutic compounds (e.g., TβRII polypeptides) to a target tissue site, providing a structure for the developing tissue and optimally capable of being resorbed into the body. For example, the matrix may provide slow release of the TβRII polypeptides. Such matrices may be formed of materials presently in use for other implanted medical applications.

The choice of matrix material is based on biocompatibility, biodegradability, mechanical properties, cosmetic appearance and interface properties. The particular application of the subject compositions will define the appropriate formulation. Potential matrices for the compositions may be biodegradable and chemically defined calcium sulfate, tricalcium phosphate, hydroxyapatite, polylactic acid and polyanhydrides. Other potential materials are biodegradable and biologically well defined, such as bone or dermal collagen. Further matrices are comprised of pure proteins or extracellular matrix components. Other potential matrices are non-biodegradable and chemically defined, such as sintered hydroxyapatite, bioglass, aluminates, or other ceramics. Matrices may be comprised of combinations of any of the above mentioned types of material, such as polylactic acid and hydroxyapatite or collagen and tricalcium phosphate. The bioceramics may be altered in composition, such as in calcium-aluminate-phosphate and processing to alter pore size, particle size, particle shape, and biodegradability.

In certain embodiments, methods of the invention can be administered for orally, e.g., in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of an agent as an active ingredient. An agent may also be administered as a bolus, electuary or paste.

In solid dosage forms for oral administration (capsules, tablets, pills, dragees, powders, granules, and the like), one or more therapeutic compounds of the present invention may be mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose, and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

Liquid dosage forms for oral administration include pharmaceutically acceptable emulsions, microemulsions, solutions, suspensions, syrups, and elixirs. In addition to the active ingredient, the liquid dosage forms may contain inert diluents commonly used in the art, such as water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor, and sesame oils), glycerol, tetrahydrofuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, coloring, perfuming, and preservative agents.

Suspensions, in addition to the active compounds, may contain suspending agents such as ethoxylated isostearyl alcohols, polyoxyethylene sorbitol, and sorbitan esters, microcrystalline cellulose, aluminum metahydroxide, bentonite, agar-agar and tragacanth, and mixtures thereof.

The compositions of the invention may also contain adjuvants, such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption, such as aluminum monostearate and gelatin.

It is understood that the dosage regimen will be determined by the attending physician considering various factors which modify the action of the subject compounds of the invention (e.g., TβRII fusion polypeptides). The various factors include, but are not limited to, the patient's age, sex, and diet, the severity disease, time of administration, and other clinical factors. Optionally, the dosage may vary with the type of matrix used in the reconstitution and the types of compounds in the composition. The addition of other known growth factors to the final composition, may also affect the dosage. Progress can be monitored by periodic assessment of bone growth and/or repair, for example, X-rays (including DEXA), histomorphometric determinations, and tetracycline labeling.

In certain embodiments, the present invention also provides gene therapy for the in vivo production of TβRII fusion polypeptides. Such therapy would achieve its therapeutic effect by introduction of the TβRII polynucleotide sequences into cells or tissues having the disorders as listed above. Delivery of TβRII polynucleotide sequences can be achieved using a recombinant expression vector such as a chimeric virus or a colloidal dispersion system. Preferred for therapeutic delivery of TβRII polynucleotide sequences is the use of targeted liposomes.

Various viral vectors which can be utilized for gene therapy as taught herein include adenovirus, herpes virus, vaccinia, or, preferably, an RNA virus such as a retrovirus. Preferably, the retroviral vector is a derivative of a murine or avian retrovirus. Examples of retroviral vectors in which a single foreign gene can be inserted include, but are not limited to: Moloney murine leukemia virus (MoMuLV), Harvey murine sarcoma virus (HaMuSV), murine mammary tumor virus (MuMTV), and Rous Sarcoma Virus (RSV). A number of additional retroviral vectors can incorporate multiple genes. All of these vectors can transfer or incorporate a gene for a selectable marker so that transduced cells can be identified and generated. Retroviral vectors can be made target-specific by attaching, for example, a sugar, a glycolipid, or a protein. Preferred targeting is accomplished by using an antibody. Those of skill in the art will recognize that specific polynucleotide sequences can be inserted into the retroviral genome or attached to a viral envelope to allow target specific delivery of the retroviral vector containing the TβRII polynucleotide. In a preferred embodiment, the vector is targeted to bone or cartilage.

Alternatively, tissue culture cells can be directly transfected with plasmids encoding the retroviral structural genes gag, pol and env, by conventional calcium phosphate transfection. These cells are then transfected with the vector plasmid containing the genes of interest. The resulting cells release the retroviral vector into the culture medium.

Another targeted delivery system for TβRII polynucleotides is a colloidal dispersion system. Colloidal dispersion systems include macromolecule complexes, nanocapsules, microspheres, beads, and lipid-based systems including oil-in-water emulsions, micelles, mixed micelles, and liposomes. The preferred colloidal system of this invention is a liposome. Liposomes are artificial membrane vesicles which are useful as delivery vehicles in vitro and in vivo. RNA, DNA and intact virions can be encapsulated within the aqueous interior and be delivered to cells in a biologically active form (see e.g., Fraley, et al., Trends Biochem. Sci., 6:77, 1981). Methods for efficient gene transfer using a liposome vehicle, are known in the art, see e.g., Mannino, et al., Biotechniques, 6:682, 1988. The composition of the liposome is usually a combination of phospholipids, usually in combination with steroids, especially cholesterol. Other phospholipids or other lipids may also be used. The physical characteristics of liposomes depend on pH, ionic strength, and the presence of divalent cations.

Examples of lipids useful in liposome production include phosphatidyl compounds, such as phosphatidylglycerol, phosphatidylcholine, phosphatidylserine, phosphatidylethanolamine, sphingolipids, cerebrosides, and gangliosides. Illustrative phospholipids include egg phosphatidylcholine, dipalmitoylphosphatidylcholine, and distearoylphosphatidylcholine. The targeting of liposomes is also possible based on, for example, organ-specificity, cell-specificity, and organelle-specificity and is known in the art.

The disclosure provides formulations that may be varied to include acids and bases to adjust the pH; and buffering agents to keep the pH within a narrow range.

EXEMPLIFICATION

The invention now being generally described, it will be more readily understood by reference to the following examples, which are included merely for purposes of illustration of certain embodiments of the present invention, and are not intended to limit the invention.

Example 1. Generation of Receptor Fusion Protein Variants

TβRII ECD Variants

TβRII fusion proteins comprising a soluble extracellular portion of human TβRII and a humanFc portion were generated. For each fusion protein, a TβRII amino acid sequence having the amino acid sequence of SEQ ID NO: 18 was fused to an IgG Fc portion having the amino acid sequence of SEQ ID NO: 20 by means of one of several different linkers. Each of the fusion proteins also included a TPA leader sequence having the amino acid sequence of SEQ ID NO: 23 (below).

```
Tissue plasminogen activator (TPA):
                                    (SEQ ID NO: 23)
MDAMKRGLCCVLLLCGAVFVSP
```

An illustration summary of several of the constructs designed is provided as FIG. 3. A table detailing the sequences for the different constructs tested in the Exemplification section is provided below:

| Construct Name | Construct Amino Acid Sequence | Linker Sequence |
|---|---|---|
| hTβRII-hFc | SEQ ID NO: 9 | TGGG (SEQ ID NO: 3) |
| hTβRII (G4S)2-hFc | SEQ ID NO: 15 | TGGGGSGGGGS (SEQ ID NO: 4) |
| hTβRII (G4S)3-hFc | SEQ ID NO: 11 | TGGGGSGGGGSGGGGS (SEQ ID NO: 5) |
| hTβRII (G4S)4-hFc | SEQ ID NO: 13 | TGGGGSGGGGSGGGGSGGGGS (SEQ ID NO: 6) |
| hTβRII extended hinge-hFc | SEQ ID NO: 17 | TGGGPKSCDK (SEQ ID NO: 7) |
| hTβRII (G4S)5-hFc | SEQ ID NO: 44 | TGGGGSGGGGSGGGGSGGGGSGGGGS (SEQ ID NO: 25) |
| hTβRII (G4S)6-hFc | SEQ ID NO: 45 | TGGGGSGGGGSGGGGSGGGGSGGGGSGGGGS (SEQ ID NO: 26) |

The amino acid sequences for the construct components and each of the constructs, along with the nucleic acid sequence used to express these constructs, are provided below.

TβRII Portion: Amino Acid Sequence
(SEQ ID NO: 18)

```
  1 TIPPHVQKSD VEMEAQKDEI ICPSCNRTAH PLRHINNDMI VTDNNGAVKF

51 PQLCKFCDVR FSTCDNQKSC MSNCSITSIC EKPQEVCVAV WRKNDENITL

101 ETVCHDPKLP YHDFILEDAA SPKCIMKEKK KPGETFFMCS CSSDECNDNI

151 IFSEEYNTSN PD
```

Fc Portion: Amino Acid Sequence
(SEQ ID NO: 20)

```
  1 THTCPPCPAP ELLGGPSVFL FPPKPKDTLM ISRTPEVTCV VVDVSHEDPE

51 VKFNWYVDGV EVHNAKTKPR EEQYNSTYRV VSVLTVLHQD WLNGKEYKCK

101 VSNKALPAPI EKTISKAKGQ PREPQVYTLP PSREEMTKNQ VSLTCLVKGF

151 YPSDIAVEWE SNGQPENNYK TTPPVLDSDG SFFLYSKLTV DKSRWQQGNV

201 FSCSVMHEAL HNHYTQKSLS LSPGK
``` hTβRII-hFc: Nucleic Acid Sequence
(SEQ ID NO: 8)

```
   1 ATGGATGCAA TGAAGAGAGG GCTCTGCTGT GTGCTGCTGC TGTGTGGAGC

51 AGTCTTCGTT TCGCCCGGCG CCACGATCCC ACCGCACGTT CAGAAGTCGG

101 ATGTGGAAAT GGAGGCCCAG AAAGATGAAA TCATCTGCCC CAGCTGTAAT

151 AGGACTGCCC ATCCACTGAG ACATATTAAT AACGACATGA TAGTCACTGA

201 CAACAACGGT GCAGTCAAGT TTCCACAACT GTGTAAATTT TGTGATGTGA

251 GATTTTCCAC CTGTGACAAC CAGAAATCCT GCATGAGCAA CTGCAGCATC

301 ACCTCCATCT GTGAGAAGCC ACAGGAAGTC TGTGTGGCTG TATGGAGAAA

351 GAATGACGAG AACATAACAC TAGAGACAGT TTGCCATGAC CCCAAGCTCC

401 CCTACCATGA CTTTATTCTG GAAGATGCTG CTTCTCCAAA GTGCATTATG

451 AAGGAAAAAA AAAAGCCTGG TGAGACTTTC TTCATGTGTT CCTGTAGCTC

501 TGATGAGTGC AATGACAACA TCATCTTCTC AGAAGAATAT AACACCAGCA

551 ATCCTGACAC CGGTGGTGGA ACTCACACAT GCCCACCGTG CCCAGCACCT

601 GAACTCCTGG GGGGACCGTC AGTCTTCCTC TTCCCCCCAA AACCCAAGGA

651 CACCCTCATG ATCTCCCGGA CCCCTGAGGT CACATGCGTG GTGGTGGACG

701 TGAGCCACGA AGACCCTGAG GTCAAGTTCA ACTGGTACGT GGACGGCGTG

751 GAGGTGCATA ATGCCAAGAC AAAGCCGCGG GAGGAGCAGT ACAACAGCAC

801 GTACCGTGTG GTCAGCGTCC TCACCGTCCT GCACCAGGAC TGGCTGAATG

851 GCAAGGAGTA CAAGTGCAAG GTCTCCAACA AAGCCCTCCC AGCCCCCATC

901 GAGAAAACCA TCTCCAAAGC CAAAGGGCAG CCCCGAGAAC CACAGGTGTA

951 CACCCTGCCC CCATCCCGGG AGGAGATGAC CAAGAACCAG GTCAGCCTGA

1001 CCTGCCTGGT CAAAGGCTTC TATCCCAGCG ACATCGCCGT GGAGTGGGAG

1051 AGCAATGGGC AGCCGGAGAA CAACTACAAG ACCACGCCTC CCGTGCTGGA

1101 CTCCGACGGC TCCTTCTTCC TCTATAGCAA GCTCACCGTG GACAAGAGCA

1151 GGTGGCAGCA GGGGAACGTC TTCTCATGCT CCGTGATGCA TGAGGCTCTG

1201 CACAACCACT ACACGCAGAA GAGCCTCTCC CTGTCTCCGG GTAAATGA
``` hTβRII-hFc: Amino Acid Sequence
(SEQ ID NO: 9)

```
  1 MDAMKRGLCC VLLLCGAVFV SPGATIPPHV QKSDVEMEAQ KDEIICPSCN
 51 RTAHPLRHIN NDMIVTDNNG AVKFPQLCKF CDVRFSTCDN QKSCMSNCSI
101 TSICEKPQEV CVAVWRKNDE NITLETVCHD PKLPYHDFIL EDAASPKCIM
151 KEKKKPGETF FMCSCSSDEC NDNIIFSEEY NTSNPDTGGG THTCPPCPAP
201 ELLGGPSVFL FPPKPKDTLM ISRTPEVTCV VVDVSHEDPE VKFNWYVDGV
251 EVHNAKTKPR EEQYNSTYRV VSVLTVLHQD WLNGKEYKCK VSNKALPAPI
301 EKTISKAKGQ PREPQVYTLP PSREEMTKNQ VSLTCLVKGF YPSDIAVEWE
351 SNGQPENNYK TTPPVLDSDG SFFLYSKLTV DKSRWQQGNV FSCSVMHEAL
401 HNHYTQKSLS LSPGK
``` hTβRII (G4S)3-hFc: Nucleic Acid Sequence
(SEQ ID NO: 10)

```
   1 ATGGATGCAA TGAAGAGAGG GCTCTGCTGT GTGCTGCTGC TGTGTGGAGC
  51 AGTCTTCGTT TCGCCCGGCG CCACGATCCC ACCGCACGTT CAGAAGTCGG
 101 ATGTGGAAAT GGAGGCCCAG AAAGATGAAA TCATCTGCCC CAGCTGTAAT
 151 AGGACTGCCC ATCCACTGAG ACATATTAAT AACGACATGA TAGTCACTGA
 201 CAACAACGGT GCAGTCAAGT TTCCACAACT GTGTAAATTT TGTGATGTGA
 251 GATTTTCCAC CTGTGACAAC CAGAAATCCT GCATGAGCAA CTGCAGCATC
 301 ACCTCCATCT GTGAGAAGCC ACAGGAAGTC TGTGTGGCTG TATGGAGAAA
 351 GAATGACGAG AACATAACAC TAGAGACAGT TTGCCATGAC CCCAAGCTCC
 401 CCTACCATGA CTTTATTCTG GAAGATGCTG CTTCTCCAAA GTGCATTATG
 451 AAGGAAAAAA AAAAGCCTGG TGAGACTTTC TTCATGTGTT CCTGTAGCTC
 501 TGATGAGTGC AATGACAACA TCATCTTCTC AGAAGAATAT AACACCAGCA
 551 ATCCTGACAC CGGTGGTGGA GGAAGTGGTG GAGGTGGTTC TGGAGGTGGT
 601 GGAAGTACTC ACACATGCCC ACCGTGCCCA GCACCTGAAC TCCTGGGGGG
 651 ACCGTCAGTC TTCCTCTTCC CCCCAAAACC CAAGGACACC CTCATGATCT
 701 CCCGGACCCC TGAGGTCACA TGCGTGGTGG TGGACGTGAG CCACGAAGAC
 751 CCTGAGGTCA AGTTCAACTG GTACGTGGAC GGCGTGGAGG TGCATAATGC
 801 CAAGACAAAG CCGCGGGAGG AGCAGTACAA CAGCACGTAC CGTGTGGTCA
 851 GCGTCCTCAC CGTCCTGCAC CAGGACTGGC TGAATGGCAA GGAGTACAAG
 901 TGCAAGGTCT CCAACAAAGC CCTCCCAGCC CCCATCGAGA AAACCATCTC
 951 CAAAGCCAAA GGGCAGCCCC GAGAACCACA GGTGTACACC CTGCCCCCAT
1001 CCCGGGAGGA GATGACCAAG AACCAGGTCA GCCTGACCTG CCTGGTCAAA
1051 GGCTTCTATC CCAGCGACAT CGCCGTGGAG TGGGAGAGCA ATGGGCAGCC
1101 GGAGAACAAC TACAAGACCA CGCCTCCCGT GCTGGACTCC GACGGCTCCT
1151 TCTTCCTCTA TAGCAAGCTC ACCGTGGACA AGAGCAGGTG GCAGCAGGGG
1201 AACGTCTTCT CATGCTCCGT GATGCATGAG GCTCTGCACA ACCACTACAC
1251 GCAGAAGAGC CTCTCCCTGT CTCCGGGTAA ATGA
``` hTβRII (G4S)3-hFc: Amino Acid Sequence
(SEQ ID NO: 11)

```
  1 MDAMKRGLCC VLLLCGAVFV SPGATIPPHV QKSDVEMEAQ KDEIICPSCN
 51 RTAHPLRHIN NDMIVTDNNG AVKFPQLCKF CDVRFSTCDN QKSCMSNCSI
```

```
101 TSICEKPQEV CVAVWRKNDE NITLETVCHD PKLPYHDFIL EDAASPKCIM

151 KEKKKPGETF FMCSCSSDEC NDNIIFSEEY NTSNPDTGGG GSGGGGSGGG

201 GSTHTCPPCP APELLGGPSV FLFPPKPKDT LMISRTPEVT CVVVDVSHED

251 PEVKFNWYVD GVEVHNAKTK PREEQYNSTY RVVSVLTVLH QDWLNGKEYK

301 CKVSNKALPA PIEKTISKAK GQPREPQVYT LPPSREEMTK NQVSLTCLVK

351 GFYPSDIAVE WESNGQPENN YKTTPPVLDS DGSFFLYSKL TVDKSRWQQG

401 NVFSCSVMHE ALHNHYTQKS LSLSPGK
``` hTβRII (G4S)4-hFc: Nucleic Acid Sequence
(SEQ ID NO: 12)

```
   1 ATGGATGCAA TGAAGAGAGG GCTCTGCTGT GTGCTGCTGC TGTGTGGAGC

51 AGTCTTCGTT TCGCCCGGCG CCACGATCCC ACCGCACGTT CAGAAGTCGG

101 ATGTGGAAAT GGAGGCCCAG AAAGATGAAA TCATCTGCCC CAGCTGTAAT

151 AGGACTGCCC ATCCACTGAG ACATATTAAT AACGACATGA TAGTCACTGA

201 CAACAACGGT GCAGTCAAGT TTCCACAACT GTGTAAATTT TGTGATGTGA

251 GATTTTCCAC CTGTGACAAC CAGAAATCCT GCATGAGCAA CTGCAGCATC

301 ACCTCCATCT GTGAGAAGCC ACAGGAAGTC TGTGTGGCTG TATGGAGAAA

351 GAATGACGAG AACATAACAC TAGAGACAGT TTGCCATGAC CCCAAGCTCC

401 CCTACCATGA CTTTATTCTG GAAGATGCTG CTTCTCCAAA GTGCATTATG

451 AAGGAAAAAA AAAAGCCTGG TGAGACTTTC TTCATGTGTT CCTGTAGCTC

501 TGATGAGTGC AATGACAACA TCATCTTCTC AGAAGAATAT AACACCAGCA

551 ATCCTGACAC CGGTGGTGGA GGTTCTGGAG GTGGAGGAAG TGGTGGAGGT

601 GGTTCTGGAG GTGGTGGAAG TACTCACACA TGCCCACCGT GCCCAGCACC

651 TGAACTCCTG GGGGGACCGT CAGTCTTCCT CTTCCCCCCA AAACCCAAGG

701 ACACCCTCAT GATCTCCCGG ACCCCTGAGG TCACATGCGT GGTGGTGGAC

751 GTGAGCCACG AAGACCCTGA GGTCAAGTTC AACTGGTACG TGGACGGCGT

801 GGAGGTGCAT AATGCCAAGA CAAAGCCGCG GGAGGAGCAG TACAACAGCA

851 CGTACCGTGT GGTCAGCGTC CTCACCGTCC TGCACCAGGA CTGGCTGAAT

901 GGCAAGGAGT ACAAGTGCAA GGTCTCCAAC AAAGCCCTCC CAGCCCCCAT

951 CGAGAAAACC ATCTCCAAAG CCAAAGGGCA GCCCCGAGAA CCACAGGTGT

1001 ACACCCTGCC CCCATCCCGG GAGGAGATGA CCAAGAACCA GGTCAGCCTG

1051 ACCTGCCTGG TCAAAGGCTT CTATCCCAGC GACATCGCCG TGGAGTGGGA

1101 GAGCAATGGG CAGCCGGAGA ACAACTACAA GACCACGCCT CCCGTGCTGG

1151 ACTCCGACGG CTCCTTCTTC CTCTATAGCA AGCTCACCGT GGACAAGAGC

1201 AGGTGGCAGC AGGGGAACGT CTTCTCATGC TCCGTGATGC ATGAGGCTCT

1251 GCACAACCAC TACACGCAGA AGAGCCTCTC CCTGTCTCCG GGTAAATGA
``` hTβRII (G4S)4-hFc: Amino Acid Sequence
(SEQ ID NO: 13)

```
   1 MDAMKRGLCC VLLLCGAVFV SPGATIPPHV QKSDVEMEAQ KDEIICPSCN

51 RTAHPLRHIN NDMIVTDNNG AVKFPQLCKF CDVRFSTCDN QKSCMSNCSI

101 TSICEKPQEV CVAVWRKNDE NITLETVCHD PKLPYHDFIL EDAASPKCIM

151 KEKKKPGETF FMCSCSSDEC NDNIIFSEEY NTSNPDTGGG GSGGGGSGGG

201 GSGGGGSTHT CPPCPAPELL GGPSVFLFPP KPKDTLMISR TPEVTCVVVD

251 VSHEDPEVKF NWYVDGVEVH NAKTKPREEQ YNSTYRVVSV LTVLHQDWLN
```

```
301  GKEYKCKVSN KALPAPIEKT ISKAKGQPRE PQVYTLPPSR EEMTKNQVSL

351  TCLVKGFYPS DIAVEWESNG QPENNYKTTP PVLDSDGSFF LYSKLTVDKS

401  RWQQGNVFSC SVMHEALHNH YTQKSLSLSP GK
``` hTβRII (G4S)4-hFc: Amino Acid Sequence lacking
leader sequence
(SEQ ID NO: 50)
```
  1  GATIPPHVQK SDVEMEAQKD EIICPSCNRT AHPLRHINND MIVTDNNGAV

51  KFPQLCKFCD VRFSTCDNQK SCMSNCSITS ICEKPQEVCV AVWRKNDENI

101  TLETVCHDPK LPYHDFILED AASPKCIMKE KKKPGETFFM CSCSSDECND

151  NIIFSEEYNT SNPDTGGGGS GGGGSGGGGS GGGGSTHTCP PCPAPELLGG

201  PSVFLFPPKP KDTLMISRTP EVTCVVVDVS HEDPEVKFNW YVDGVEVHNA

251  KTKPREEQYN STYRVVSVLT VLHQDWLNGK EYKCKVSNKA LPAPIEKTIS

301  KAKGQPREPQ VYTLPPSREE MTKNQVSLTC LVKGFYPSDI AVEWESNGQP

351  ENNYKTTPPV LDSDGSFFLY SKLTVDKSRW QQGNVFSCSV MHEALHNHYT

401  QKSLSLSPGK
``` hTβRII (G4S)4-hFc: Amino Acid Sequence lacking leader
sequence and lacking glycine prior to hTβRII portion
(SEQ ID NO: 52)
```
  1  ATIPPHVQKS DVEMEAQKDE IICPSCNRTA HPLRHINNDM IVTDNNGAVK

51  FPQLCKFCDV RFSTCDNQKS CMSNCSITSI CEKPQEVCVA VWRKNDENIT

101  LETVCHDPKL PYHDFILEDA ASPKCIMKEK KKPGETFFMC SCSSDECNDN

151  IIFSEEYNTS NPDTGGGGSG GGGSGGGGSG GGSTHTCPPC PAPELLGGP

201  SVFLFPPKPK DTLMISRTPE VTCVVVDVSH EDPEVKFNWY VDGVEVHNAK

251  TKPREEQYNS TYRVVSVLTV LHQDWLNGKE YKCKVSNKAL PAPIEKTISK

301  AKGQPREPQV YTLPPSREEM TKNQVSLTCL VKGFYPSDIA VEWESNGQPE

351  NNYKTTPPVL DSDGSFFLYS KLTVDKSRWQ QGNVFSCSVM HEALHNHYTQ

401  KSLSLSPGK
``` hTβRII (G4S)4-hFc: Amino Acid Sequence lacking leader
sequence and lacking glycine and alanine prior
to hTβRII portion
(SEQ ID NO: 51)
```
  1  TIPPHVQKSD VEMEAQKDEI ICPSCNRTAH PLRHINNDMI VTDNNGAVKF

51  PQLCKFCDVR FSTCDNQKSC MSNCSITSIC EKPQEVCVAV WRKNDENITL

101  ETVCHDPKLP YHDFILEDAA SPKCIMKEKK KPGETFFMCS CSSDECNDNI

151  IFSEEYNTSN PDTGGGGSGG GGSGGGGSGG GSTHTCPPC PAPELLGGPS

201  VFLFPPKPKD TLMISRTPEV TCVVVDVSHE DPEVKFNWYV DGVEVHNAKT

251  KPREEQYNST YRVVSVLTVL HQDWLNGKEY KCKVSNKALP APIEKTISKA

301  KGQPREPQVY TLPPSREEMT KNQVSLTCLV KGFYPSDIAV EWESNGQPEN

351  NYKTTPPVLD SDGSFFLYSK LTVDKSRWQQ GNVFSCSVMH EALHNHYTQK

401  SLSLSPGK
``` hTβRII (G4S)4-hFc: Amino Acid Sequence lacking leader
sequence and lacking glycine, alanine, and threonine
prior to hTβRII portion
(SEQ ID NO: 53)
```
  1  IPPHVQKSDV EMEAQKDEII CPSCNRTAHP LRHINNDMIV TDNNGAVKFP

51  QLCKFCDVRF STCDNQKSCM SNCSITSICE KPQEVCVAVW RKNDENITLE

101  TVCHDPKLPY HDFILEDAAS PKCIMKEKKK PGETFFMCSC SSDECNDNII
```

```
151  FSEEYNTSNP DTGGGGSGGG GSGGGGSGGG GSTHTCPPCP APELLGGPSV

201  FLFPPKPKDT LMISRTPEVT CVVVDVSHED PEVKFNWYVD GVEVHNAKTK

251  PREEQYNSTY RVVSVLTVLH QDWLNGKEYK CKVSNKALPA PIEKTISKAK

301  GQPREPQVYT LPPSREEMTK NQVSLTCLVK GFYPSDIAVE WESNGQPENN

351  YKTTPPVLDS DGSFFLYSKL TVDKSRWQQG NVFSCSVMHE ALHNHYTQKS

401  LSLSPGK
``` hTβRII (G4S)4-hFc: Amino Acid Sequence lacking leader sequence and lacking glycine, alanine, threonine, and isoleucine prior to hTβRII portion
(SEQ ID NO: 54)

```
  1  PPHVQKSDVE MEAQKDEIIC PSCNRTAHPL RHINNDMIVT DNNGAVKFPQ

51  LCKFCDVRFS TCDNQKSCMS NCSITSICEK PQEVCVAVWR KNDENITLET

101  VCHDPKLPYH DFILEDAASP KCIMKEKKKP GETFFMCSCS SDECNDNIIF

151  SEEYNTSNPD TGGGGSGGGG SGGGGSGGGG STHTCPPCPA PELLGGPSVF

201  LFPPKPKDTL MISRTPEVTC VVVDVSHEDP EVKFNWYVDG VEVHNAKTKP

251  REEQYNSTYR VVSVLTVLHQ DWLNGKEYKC KVSNKALPAP IEKTISKAKG

301  QPREPQVYTL PPSREEMTKN QVSLTCLVKG FYPSDIAVEW ESNGQPENNY

351  KTTPPVLDSD GSFFLYSKLT VDKSRWQQGN VFSCSVMHEA LHNHYTQKSL

401  SLSPGK
``` hTβRII (G4S)4-hFc: Amino Acid Sequence lacking leader sequence and lacking glycine, alanine, threonine, isoleucine, and proline prior to hTβRII portion
(SEQ ID NO: 55)

```
  1  PHVQKSDVEM EAQKDEIICP SCNRTAHPLR HINNDMIVTD NNGAVKFPQL

51  CKFCDVRFST CDNQKSCMSN CSITSICEKP QEVCVAVWRK NDENITLETV

101  CHDPKLPYHD FILEDAASPK CIMKEKKKPG ETFFMCSCSS DECNDNIIFS

151  EEYNTSNPDT GGGGSGGGGS GGGGSGGGGS THTCPPCPAP ELLGGPSVFL

201  FPPKPKDTLM ISRTPEVTCV VVDVSHEDPE VKFNWYVDGV EVHNAKTKPR

251  EEQYNSTYRV VSVLTVLHQD WLNGKEYKCK VSNKALPAPI EKTISKAKGQ

301  PREPQVYTLP PSREEMTKNQ VSLTCLVKGF YPSDIAVEWE SNGQPENNYK

351  TTPPVLDSDG SFFLYSKLTV DKSRWQQGNV FSCSVMHEAL HNHYTQKSLS

401  LSPGK
``` hTβRII (G4S)4-hFc: Amino Acid Sequence lacking leader sequence and lacking glycine, alanine, threonine, isoleucine, proline, and proline prior to hTβRII portion
(SEQ ID NO: 56)

```
  1  HVQKSDVEME AQKDEIICPS CNRTAHPLRH INNDMIVTDN NGAVKFPQLC

51  KFCDVRFSTC DNQKSCMSNC SITSICEKPQ EVCVAVWRKN DENITLETVC

101  HDPKLPYHDF ILEDAASPKC IMKEKKKPGE TFFMCSCSSD ECNDNIIFSE

151  EYNTSNPDTG GGGSGGGGSG GGGSGGGGST HTCPPCPAPE LLGGPSVFLF

201  PPKPKDTLMI SRTPEVTCVV VDVSHEDPEV KFNWYVDGVE VHNAKTKPRE

251  EQYNSTYRVV SVLTVLHQDW LNGKEYKCKV SNKALPAPIE KTISKAKGQP

301  REPQVYTLPP SREEMTKNQV SLTCLVKGFY PSDIAVEWES NGQPENNYKT

351  TPPVLDSDGS FFLYSKLTVD KSRWQQGNVF SCSVMHEALH NHYTQKSLSL

401  SPGK
```

-continued hTβRII (G4S)2-hFc: Nucleic Acid Sequence
(SEQ ID NO: 14)

```
   1 ATGGATGCAA TGAAGAGAGG GCTCTGCTGT GTGCTGCTGC TGTGTGGAGC
  51 AGTCTTCGTT TCGCCCGGCG CCACGATCCC ACCGCACGTT CAGAAGTCGG
 101 ATGTGGAAAT GGAGGCCCAG AAAGATGAAA TCATCTGCCC CAGCTGTAAT
 151 AGGACTGCCC ATCCACTGAG ACATATTAAT AACGACATGA TAGTCACTGA
 201 CAACAACGGT GCAGTCAAGT TTCCACAACT GTGTAAATTT TGTGATGTGA
 251 GATTTTCCAC CTGTGACAAC CAGAAATCCT GCATGAGCAA CTGCAGCATC
 301 ACCTCCATCT GTGAGAAGCC ACAGGAAGTC TGTGTGGCTG TATGGAGAAA
 351 GAATGACGAG AACATAACAC TAGAGACAGT TTGCCATGAC CCCAAGCTCC
 401 CCTACCATGA CTTTATTCTG GAAGATGCTG CTTCTCCAAA GTGCATTATG
 451 AAGGAAAAAA AAAAGCCTGG TGAGACTTTC TTCATGTGTT CCTGTAGCTC
 501 TGATGAGTGC AATGACAACA TCATCTTCTC AGAAGAATAT AACACCAGCA
 551 ATCCTGACAC CGGTGGAGGT GGTTCTGGAG GTGGTGGAAG TACTCACACA
 601 TGCCCACCGT GCCCAGCACC TGAACTCCTG GGGGGACCGT CAGTCTTCCT
 651 CTTCCCCCCA AAACCCAAGG ACACCCTCAT GATCTCCCGG ACCCCTGAGG
 701 TCACATGCGT GGTGGTGGAC GTGAGCCACG AAGACCCTGA GGTCAAGTTC
 751 AACTGGTACG TGGACGGCGT GGAGGTGCAT AATGCCAAGA CAAAGCCGCG
 801 GGAGGAGCAG TACAACAGCA CGTACCGTGT GGTCAGCGTC CTCACCGTCC
 851 TGCACCAGGA CTGGCTGAAT GGCAAGGAGT ACAAGTGCAA GGTCTCCAAC
 901 AAAGCCCTCC CAGCCCCCAT CGAGAAAACC ATCTCCAAAG CCAAAGGGCA
 951 GCCCCGAGAA CCACAGGTGT ACACCCTGCC CCCATCCCGG GAGGAGATGA
1001 CCAAGAACCA GGTCAGCCTG ACCTGCCTGG TCAAAGGCTT CTATCCCAGC
1051 GACATCGCCG TGGAGTGGGA GAGCAATGGG CAGCCGGAGA ACAACTACAA
1101 GACCACGCCT CCCGTGCTGG ACTCCGACGG CTCCTTCTTC CTCTATAGCA
1151 AGCTCACCGT GGACAAGAGC AGGTGGCAGC AGGGGAACGT CTTCTCATGC
1201 TCCGTGATGC ATGAGGCTCT GCACAACCAC TACACGCAGA AGAGCCTCTC
1251 CCTGTCTCCG GGTAAATGA
``` hTβRII (G4S)2-hFc: Amino Acid Sequence
(SEQ ID NO: 15)

```
   1 MDAMKRGLCC VLLLCGAVFV SPGATIPPHV QKSDVEMEAQ KDEIICPSCN
  51 RTAHPLRHIN NDMIVTDNNG AVKFPQLCKF CDVRFSTCDN QKSCMSNCSI
 101 TSICEKPQEV CVAVWRKNDE NITLETVCHD PKLPYHDFIL EDAASPKCIM
 151 KEKKKPGETF FMCSCSSDEC NDNIIFSEEY NTSNPDTGGG GSGGGGSTHT
 201 CPPCPAPELL GGPSVFLFPP KPKDTLMISR TPEVTCVVVD VSHEDPEVKF
 251 NWYVDGVEVH NAKTKPREEQ YNSTYRVVSV LTVLHQDWLN GKEYKCKVSN
 301 KALPAPIEKT ISKAKGQPRE PQVYTLPPSR EEMTKNQVSL TCLVKGFYPS
 351 DIAVEWESNG QPENNYKTTP PVLDSDGSFF LYSKLTVDKS RWQQGNVFSC
 401 SVMHEALHNH YTQKSLSLSP GK
``` hTβRII extended hinge-hFc: Nucleic Acid Sequence
(SEQ ID NO: 16)

```
   1 ATGGATGCAA TGAAGAGAGG GCTCTGCTGT GTGCTGCTGC TGTGTGGAGC
  51 AGTCTTCGTT TCGCCCGGCG CCACGATCCC ACCGCACGTT CAGAAGTCGG
```

-continued

```
 101 ATGTGGAAAT GGAGGCCCAG AAAGATGAAA TCATCTGCCC CAGCTGTAAT

151 AGGACTGCCC ATCCACTGAG ACATATTAAT AACGACATGA TAGTCACTGA

201 CAACAACGGT GCAGTCAAGT TTCCACAACT GTGTAAATTT TGTGATGTGA

251 GATTTTCCAC CTGTGACAAC CAGAAATCCT GCATGAGCAA CTGCAGCATC

301 ACCTCCATCT GTGAGAAGCC ACAGGAAGTC TGTGTGGCTG TATGGAGAAA

351 GAATGACGAG AACATAACAC TAGAGACAGT TTGCCATGAC CCCAAGCTCC

401 CCTACCATGA CTTTATTCTG GAAGATGCTG CTTCTCCAAA GTGCATTATG

451 AAGGAAAAAA AAAAGCCTGG TGAGACTTTC TTCATGTGTT CCTGTAGCTC

501 TGATGAGTGC AATGACAACA TCATCTTCTC AGAAGAATAT AACACCAGCA

551 ATCCTGACAC CGGTGGTGGA CCCAAATCTT GTGACAAAAC TCACACATGC

601 CCACCGTGCC CAGCACCTGA ACTCCTGGGG GGACCGTCAG TCTTCCTCTT

651 CCCCCCAAAA CCCAAGGACA CCCTCATGAT CTCCCGGACC CCTGAGGTCA

701 CATGCGTGGT GGTGGACGTG AGCCACGAAG ACCCTGAGGT CAAGTTCAAC

751 TGGTACGTGG ACGGCGTGGA GGTGCATAAT GCCAAGACAA AGCCGCGGGA

801 GGAGCAGTAC AACAGCACGT ACCGTGTGGT CAGCGTCCTC ACCGTCCTGC

851 ACCAGGACTG GCTGAATGGC AAGGAGTACA AGTGCAAGGT CTCCAACAAA

901 GCCCTCCCAG CCCCCATCGA GAAAACCATC TCCAAAGCCA AGGGCAGCC

951 CCGAGAACCA CAGGTGTACA CCCTGCCCCC ATCCCGGGAG GAGATGACCA

1001 AGAACCAGGT CAGCCTGACC TGCCTGGTCA AAGGCTTCTA TCCCAGCGAC

1051 ATCGCCGTGG AGTGGGAGAG CAATGGGCAG CCGGAGAACA ACTACAAGAC

1101 CACGCCTCCC GTGCTGGACT CCGACGGCTC CTTCTTCCTC TATAGCAAGC

1151 TCACCGTGGA CAAGAGCAGG TGGCAGCAGG GAACGTCTT CTCATGCTCC

1201 GTGATGCATG AGGCTCTGCA CAACCACTAC ACGCAGAAGA GCCTCTCCCT

1251 GTCCCCGGGT AAATGA
``` hTβRII extended hinge-hFc: Amino Acid Sequence
(SEQ ID NO: 17)

```
  1 MDAMKRGLCC VLLLCGAVFV SPGATIPPHV QKSDVEMEAQ KDEIICPSCN

51 RTAHPLRHIN NDMIVTDNNG AVKFPQLCKF CDVRFSTCDN QKSCMSNCSI

101 TSICEKPQEV CVAVWRKNDE NITLETVCHD PKLPYHDFIL EDAASPKCIM

151 KEKKKPGETF FMCSCSSDEC NDNIIFSEEY NTSNPDTGGG PKSCDKTHTC

201 PPCPAPELLG GPSVFLFPPK PKDTLMISRT PEVTCVVVDV SHEDPEVKFN

251 WYVDGVEVHN AKTKPREEQY NSTYRVVSVL TVLHQDWLNG KEYKCKVSNK

301 ALPAPIEKTI SKAKGQPREP QVYTLPPSRE EMTKNQVSLT CLVKGFYPSD

351 IAVEWESNGQ PENNYKTTPP VLDSDGSFFL YSKLTVDKSR WQQGNVFSCS

401 VMHEALHNHY TQKSLSLSPG K
``` hTβRII (G4S)5-hFc: Amino Acid Sequence
(SEQ ID NO: 44)

```
  1 MDAMKRGLCC VLLLCGAVFV SPGATIPPHV QKSDVEMEAQ KDEIICPSCN

51 RTAHPLRHIN NDMIVTDNNG AVKFPQLCKF CDVRFSTCDN QKSCMSNCSI

101 TSICEKPQEV CVAVWRKNDE NITLETVCHD PKLPYHDFIL EDAASPKCIM

151 KEKKKPGETF FMCSCSSDEC NDNIIFSEEY NTSNPDTGGG GSGGGGSGGG

201 GSGGGGSGGG GSTHTCPPCP APELLGGPSV FLFPPKPKDT LMISRTPEVT

251 CVVVDVSHED PEVKFNWYVD GVEVHNAKTK PREEQYNSTY RVVSVLTVLH
```

```
301 QDWLNGKEYK CKVSNKALPA PIEKTISKAK GQPREPQVYT LPPSREEMTK

351 NQVSLTCLVK GFYPSDIAVE WESNGQPENN YKTTPPVLDS DGSFFLYSKL

401 TVDKSRWQQG NVFSCSVMHE ALHNHYTQKS LSLSPGK
``` hTβRII (G4S)6-hFc: Amino Acid Sequence
(SEQ ID NO: 45)
```
  1 MDAMKRGLCC VLLLCGAVFV SPGATIPPHV QKSDVEMEAQ KDEIICPSCN

51 RTAHPLRHIN NDMIVTDNNG AVKFPQLCKF CDVRFSTCDN QKSCMSNCSI

101 TSICEKPQEV CVAVWRKNDE NITLETVCHD PKLPYHDFIL EDAASPKCIM

151 KEKKKPGETF FMCSCSSDEC NDNIIFSEEY NTSNPDTGGG GSGGGGSGGG

201 GSGGGGSGGG GSGGGGSTHT CPPCPAPELL GGPSVFLFPP KPKDTLMISR

251 TPEVTCVVVD VSHEDPEVKF NWYVDGVEVH NAKTKPREEQ YNSTYRVVSV

301 LTVLHQDWLN GKEYKCKVSN KALPAPIEKT ISKAKGQPRE PQVYTLPPSR

351 EEMTKNQVSL TCLVKGFYPS DIAVEWESNG QPENNYKTTP PVLDSDGSFF

401 LYSKLTVDKS RWQQGNVFSC SVMHEALHNH YTQKSLSLSP GK
``` hTβRII (G4S)5-hFc: Nucleotide Sequence
(SEQ ID NO: 46)
```
   1 ATGGATGCAA TGAAGAGAGG GCTCTGCTGT GTGCTGCTGC TGTGTGGAGC

51 AGTCTTCGTT TCGCCCGGCG CCACGATCCC ACCGCACGTT CAGAAGTCGG

101 ATGTGGAAAT GGAGGCCCAG AAAGATGAAA TCATCTGCCC CAGCTGTAAT

151 AGGACTGCCC ATCCACTGAG ACATATTAAT AACGACATGA TAGTCACTGA

201 CAACAACGGT GCAGTCAAGT TTCCACAACT GTGTAAATTT TGTGATGTGA

251 GATTTTCCAC CTGTGACAAC CAGAAATCCT GCATGAGCAA CTGCAGCATC

301 ACCTCCATCT GTGAGAAGCC ACAGGAAGTC TGTGTGGCTG TATGGAGAAA

351 GAATGACGAG AACATAACAC TAGAGACAGT TTGCCATGAC CCCAAGCTCC

401 CCTACCATGA CTTTATTCTG GAAGATGCTG CTTCTCCAAA GTGCATTATG

451 AAGGAAAAAA AAAAGCCTGG TGAGACTTTC TTCATGTGTT CCTGTAGCTC

501 TGATGAGTGC AATGACAACA TCATCTTCTC AGAAGAATAT AACACCAGCA

551 ATCCTGACAC CGGTGGAGGA GGTTCTGGTG GTGGAGGTTC TGGAGGTGGA

601 GGAAGTGGTG GAGGTGGTTC TGGAGGTGGT GGAAGTACTC ACACATGCCC

651 ACCGTGCCCA GCACCTGAAC TCCTGGGGGG ACCGTCAGTC TTCCTCTTCC

701 CCCCAAAACC CAAGGACACC CTCATGATCT CCCGGACCCC TGAGGTCACA

751 TGCGTGGTGG TGGACGTGAG CCACGAAGAC CCTGAGGTCA AGTTCAACTG

801 GTACGTGGAC GGCGTGGAGG TGCATAATGC CAAGACAAAG CCGCGGGAGG

851 AGCAGTACAA CAGCACGTAC CGTGTGGTCA GCGTCCTCAC CGTCCTGCAC

901 CAGGACTGGC TGAATGGCAA GGAGTACAAG TGCAAGGTCT CCAACAAAGC

951 CCTCCCAGCC CCCATCGAGA AAACCATCTC CAAAGCCAAA GGGCAGCCCC

1001 GAGAACCACA GGTGTACACC CTGCCCCCAT CCCGGGAGGA GATGACCAAG

1051 AACCAGGTCA GCCTGACCTG CCTGGTCAAA GGCTTCTATC CAGCGACAT
``` hTβRII (G4S)6-hFc: Nucleotide Sequence (SEQ ID NO: 47)

```
   1 ATGGATGCAA TGAAGAGAGG GCTCTGCTGT GTGCTGCTGC TGTGTGGAGC
  51 AGTCTTCGTT TCGCCCGGCG CCACGATCCC ACCGCACGTT CAGAAGTCGG
 101 ATGTGGAAAT GGAGGCCCAG AAAGATGAAA TCATCTGCCC CAGCTGTAAT
 151 AGGACTGCCC ATCCACTGAG ACATATTAAT AACGACATGA TAGTCACTGA
 201 CAACAACGGT GCAGTCAAGT TTCCACAACT GTGTAAATTT TGTGATGTGA
 251 GATTTTCCAC CTGTGACAAC CAGAAATCCT GCATGAGCAA CTGCAGCATC
 301 ACCTCCATCT GTGAGAAGCC ACAGGAAGTC TGTGTGGCTG TATGGAGAAA
 351 GAATGACGAG AACATAACAC TAGAGACAGT TTGCCATGAC CCCAAGCTCC
 401 CCTACCATGA CTTTATTCTG GAAGATGCTG CTTCTCCAAA GTGCATTATG
 451 AAGGAAAAAA AAAAGCCTGG TGAGACTTTC TTCATGTGTT CCTGTAGCTC
 501 TGATGAGTGC AATGACAACA TCATCTTCTC AGAAGAATAT AACACCAGCA
 551 ATCCTGACAC CGGTGGAGGT GGAAGTGGTG GAGGAGGTTC TGGTGGTGGA
 601 GGTTCTGGAG GTGGAGGAAG TGGTGGAGGT GGTTCTGGAG GTGGTGGAAG
 651 TACTCACACA TGCCCACCGT GCCCAGCACC TGAACTCCTG GGGGGACCGT
 701 CAGTCTTCCT CTTCCCCCCA AAACCCAAGG ACACCCTCAT GATCTCCCGG
 751 ACCCCTGAGG TCACATGCGT GGTGGTGGAC GTGAGCCACG AAGACCCTGA
 801 GGTCAAGTTC AACTGGTACG TGGACGGCGT GGAGGTGCAT AATGCCAAGA
 851 CAAAGCCGCG GGAGGAGCAG TACAACAGCA CGTACCGTGT GGTCAGCGTC
 901 CTCACCGTCC TGCACCAGGA CTGGCTGAAT GGCAAGGAGT ACAAGTGCAA
 951 GGTCTCCAAC AAAGCCCTCC CAGCCCCCAT CGAGAAAACC ATCTCCAAAG
1001 CCAAAGGGCA GCCCCGAGAA CCACAGGTGT ACACCCTGCC CCCATCCCGG
1051 GAGGAGATGA CCAAGAACCA GGTCAGCCTG ACCTGCCTGG TCAAAGGCTT
1101 CTATCCCAGC GACATCGCCG TGGAGTGGGA GAGCAATGGG CAGCCGGAGA
1151 ACAACTACAA GACCACGCCT CCCGTGCTGG ACTCCGACGG CTCCTTCTTC
1201 CTCTATAGCA AGCTCACCGT GGACAAGAGC AGGTGGCAGC AGGGGAACGT
1251 CTTCTCATGC TCCGTGATGC ATGAGGCTCT GCACAACCAC TACACGCAGA
1301 AGAGCCTCTC CCTGTCTCCG GGTAAATGA
```

The various constructs were successfully expressed in CHO cells and were purified to a high degree of purity as determined by analytical size-exclusion chromatography and SDS-PAGE. The hTβRII (G4S)2-hFc, hTβRII (G4S)3-hFc, hTβRII (G4S)4-hFc, hTβRII (G4S)5-hFc and hTβRII (G4S)6-hFc proteins displayed similarly strong stability as determined by SDS-PAGE analysis when maintained in PBS for 13 days at 37° C. The hTβRII (G4S)2-hFc, hTβRII (G4S)3-hFc, hTβRII (G4S)4-hFc proteins were also maintained in rat, mouse or human serum and displayed similarly strong stability.

TβRII ECD Variants

In addition to the TβRII domains included in the fusion proteins described above (e.g., SEQ ID NO: 18), the disclosure also contemplates fusion proteins comprising alternative TβRII domains. For example, the fusion protein may comprise the wild-type hTβRII$_{short}$(23-159) sequence shown below (SEQ ID NO: 27) or any of the other TβRII polypeptides disclosed below:

```
                                               (SEQ ID NO: 27)
  1 TIPPHVQKSV NNDMIVTDNN GAVKFPQLCK FCDVRFSTCD NQKSCMSNCS

51 ITSICEKPQE VCVAVWRKND ENITLETVCH DPKLPYHDFI LEDAASPKCI

101 MKEKKKPGET FFMCSCSSDE CNDNIIFSEE YNTSNPD
```

(1) The hTβRII$_{short}$(23-159/D110K) amino acid sequence shown below (SEQ ID NO: 36), in which the substituted residue is underlined.

```
                                               (SEQ ID NO: 36)
  1 TIPPHVQKSV NNDMIVTDNN GAVKFPQLCK FCDVRFSTCD NQKSCMSNCS

51 ITSICEKPQE VCVAVWRKND ENITLETVCH DPKLPYHKFI LEDAASPKCI

101 MKEKKKPGET FFMCSCSSDE CNDNIIFSEE YNTSNPD
```

(2) The N-terminally truncated hTβRII$_{short}$(29-159) amino acid sequence shown below (SEQ ID NO: 28).

```
                                               (SEQ ID NO: 28)
  1 QKSVNNDMIV TDNNGAVKFP QLCKFCDVRF STCDNQKSCM SNCSITSICE

51 KPQEVCVAVW RKNDENITLE TVCHDPKLPY HDFILEDAAS PKCIMKEKKK

101 PGETFFMCSC SSDECNDNII FSEEYNTSNP D
```

(3) The N-terminally truncated hTβRII$_{short}$(35-159) amino acid sequence shown below (SEQ ID NO: 29).

```
                                               (SEQ ID NO: 29)
  1 DMIVTDNNGA VKFPQLCKFC DVRFSTCDNQ KSCMSNCSIT SICEKPQEVC

51 VAVWRKNDEN ITLETVCHDP KLPYHDFILE DAASPKCIMK EKKKPGETFF

101 MCSCSSDECN DNIIFSEEYN TSNPD
```

(4) The C-terminally truncated hTβRII$_{short}$(23-153) amino acid sequence shown below (SEQ ID NO: 30).

```
                                               (SEQ ID NO: 30)
  1 TIPPHVQKSV NNDMIVTDNN GAVKFPQLCK FCDVRFSTCD NQKSCMSNCS

51 ITSICEKPQE VCVAVWRKND ENITLETVCH DPKLPYHDFI LEDAASPKCI

101 MKEKKKPGET FFMCSCSSDE CNDNIIFSEE Y
```

(5) The C-terminally truncated hTβRII$_{short}$(23-153/N70D) amino acid sequence shown below (SEQ ID NO: 38), in which the substituted residue is underlined.

```
                                               (SEQ ID NO: 38)
  1 TIPPHVQKSV NNDMIVTDNN GAVKFPQLCK FCDVRFSTCD NQKSCMSDCS

51 ITSICEKPQE VCVAVWRKND ENITLETVCH DPKLPYHDFI LEDAASPKCI

101 MKEKKKPGET FFMCSCSSDE CNDNIIFSEE Y
```

Applicants also envision five corresponding variants (SEQ ID NOs: 37, 33, 34, 39) based on the wild-type hTβRII$_{long}$(23-184) sequence shown above and below (SEQ ID NO: 49), in which the 25 amino-acid insertion is underlined. Note that splicing results in a conservative amino acid substitution (Val→Ile) at the flanking position C-terminal to the insertion.

```
                                                    (SEQ ID NO: 49)
  1 TIPPHVQKSDVEMEAQKDEIICPSCNRTAHPLRHINNDMI VTDNNGAVKF

51 PQLCKFCDVR FSTCDNQKSC MSNCSITSIC EKPQEVCVAV WRKNDENITL

101 ETVCHDPKLP YHDFILEDAA SPKCIMKEKK KPGETFFMCS CSSDECNDNI

151 IFSEEYNTSN PD
```

(1) The hTβRII$_{long}$(23-184/D135K) amino acid sequence shown below (SEQ ID NO: 37), in which the substituted residue is double underlined.

```
                                                    (SEQ ID NO: 37)
  1 TIPPHVQKSDVEMEAQKDEIICPSCNRTAHPLRHINNDMI VTDNNGAVKF

51 PQLCKFCDVR FSTCDNQKSC MSNCSITSIC EKPQEVCVAV WRKNDENITL

101 ETVCHDPKLP YHKFILEDAA SPKCIMKEKK KPGETFFMCS CSSDECNDNI

151 IFSEEYNTSN PD
```

(2) The N-terminally truncated hTβRII$_{long}$(29-184) amino acid sequence shown below (SEQ ID NO: 33).

```
                                                    (SEQ ID NO: 33)
  1 QKSDVEMEAQKDEIICPSCNRTAHPLRHIN NDMIVTDNNG AVKFPQLCKF

51 CDVRFSTCDN QKSCMSNCSI TSICEKPQEV CVAVWRKNDE NITLETVCHD

101 PKLPYHDFIL EDAASPKCIM KEKKKPGETF FMCSCSSDEC NDNIIFSEEY

151 NTSNPD
```

(3) The N-terminally truncated hTβRII$_{long}$(60-184) amino acid sequence shown below (same as SEQ ID NO: 29).

```
                                                (same as SEQ ID NO: 29)
  1 DMIVTDNNGA VKFPQLCKFC DVRFSTCDNQ KSCMSNCSIT SICEKPQEVC

51 VAVWRKNDEN ITLETVCHDP KLPYHDFILE DAASPKCIMK EKKKPGETFF

101 MCSCSSDECN DNIIFSEEYN TSNPD
```

(4) The C-terminally truncated hTβRII$_{long}$(23-178) amino acid sequence shown below (SEQ ID NO: 34).

```
                                                    (SEQ ID NO: 34)
  1 TIPPHVQKSDVEMEAQKDEIICPSCNRTAHPLRHINNDMI VTDNNGAVKF

51 PQLCKFCDVR FSTCDNQKSC MSNCSITSIC EKPQEVCVAV WRKNDENITL

101 ETVCHDPKLP YHDFILEDAA SPKCIMKEKK KPGETFFMCS CSSDECNDNI

151 IFSEEY
```

(5) The C-terminally truncated hTβRII$_{long}$(23-178/N95D) amino acid sequence shown below (SEQ ID NO: 39), in which the substituted residue is double underlined.

```
                                                    (SEQ ID NO: 39)
  1 TIPPHVQKSDVEMEAQKDEIICPSCNRTAHPLRHINNDMI VTDNNGAVKF

51 PQLCKFCDVR FSTCDNQKSC MSDCSITSIC EKPQEVCVAV WRKNDENITL

101 ETVCHDPKLP YHDFILEDAA SPKCIMKEKK KPGETFFMCS CSSDECNDNI

151 IFSEEY
```

Additional TβRII ECD variants include:
(A) The N- and C-terminally truncated hTβRII$_{short}$(35-153) or hTβRII$_{long}$(60-178) amino acid sequence shown below (SEQ ID NO: 32).

```
                                                  (SEQ ID NO: 32)
  1 DMIVTDNNGA VKFPQLCKFC DVRFSTCDNQ KSCMSNCSIT SICEKPQEVC

51 VAVWRKNDEN ITLETVCHDP KLPYHDFILE DAASPKCIMK EKKKPGETFF

101 MCSCSSDECN DNIIFSEEY
```

(B) The N- and C-terminally truncated hTβRII$_{short}$(29-153) amino acid sequence shown below (SEQ ID NO: 31).

```
                                                  (SEQ ID NO: 31)
  1 QKSVNNDMIV TDNNGAVKFP QLCKFCDVRF STCDNQKSCM SNCSITSICE

51 KPQEVCVAVW RKNDENITLE TVCHDPKLPY HDFILEDAAS PKCIMKEKKK

101 PGETFFMCSC SSDECNDNII FSEEY
```

(C) The N- and C-terminally truncated hTβRII$_{long}$(29-178) amino acid sequence shown below (SEQ ID NO: 35).

```
                                                  (SEQ ID NO: 35)
  1 QKSDVEMEAQKDEIICPSCNRTAHPLRHIN NDMIVTDNNG AVKFPQLCKF

51 CDVRFSTCDN QKSCMSNCSI TSICEKPQEV CVAVWRKNDE NITLETVCHD

101 PKLPYHDFIL EDAASPKCIM KEKKKPGETF FMCSCSSDEC NDNIIFSEEY
```

Any of the above variants (SEQ ID NO: 36, 28, 29, 30, 38, 37, 33, 34, 39, 32, 31, and 35) could incorporate an insertion of 36 amino acids (SEQ ID NO: 41) between the pair of glutamate residues (positions 151 and 152 of SEQ ID NO: 1, or positions 176 and 177 of SEQ ID NO: 2) located near the C-terminus of the hTβRII ECD, as occurs naturally in the hTβRII isoform C (Konrad et al., BMC Genomics 8:318, 2007).

```
                   (SEQ ID NO: 41)
 GRCKIRHIGS NNRLQRSTCQ NTGWESAHVM KTPGFR
```

As an example, the paired glutamate residues flanking the optional insertion site are denoted below (underlined) for the hTβRII$_{short}$(29-159) variant (SEQ ID NO: 28).

```
                                                  (SEQ ID NO: 28)
  1 QKSVNNDMIV TDNNGAVKFP QLCKFCDVRF STCDNQKSCM SNCSITSICE

51 KPQEVCVAVW RKNDENITLE TVCHDPKLPY HDFILEDAAS PKCIMKEKKK

101 PGETFFMCSC SSDECNDNII FSEEYNTSNP D
```

Fc Domain Variants

While the constructs described above were generated with an Fc domain having the amino acid sequence of SEQ ID NO: 20, the disclosure contemplates hTβRII-hFc fusion proteins comprising alternative Fc domains, including a human IgG2 Fc domain (SEQ ID NO: 42, below) or full-length human IgG1 Fc (hG1Fc) (SEQ ID NO: 43, below). Optionally, a polypeptide unrelated to an Fc domain could be attached in place of the Fc domain.

```
                                                  (SEQ ID NO: 42)
  1 VECPPCPAPP VAGPSVFLFP PKPKDTLMIS RTPEVTCVVV DVSHEDPEVQ

51 FNWYVDGVEV HNAKTKPREE QFNSTFRVVS VLTVVHQDWL NGKEYKCKVS

101 NKGLPAPIEK TISKTKGQPR EPQVYTLPPS REEMTKNQVS LTCLVKGFYP
```

```
151 SDIAVEWESN GQPENNYKTT PPMLDSDGSF FLYSKLTVDK SRWQQGNVFS

201 CSVMHEALHN HYTQKSLSLS PGK (SEQ ID NO: 43)
  1 GGPKSCDKTH TCPPCPAPEL LGGPSVFLFP PKPKDTLMIS RTPEVTCVVV

51 DVSHEDPEVK FNWYVDGVEV HNAKTKPREE QYNSTYRVVS VLTVLHQDWL

101 NGKEYKCKVS NKALPAPIEK TISKAKGQPR EPQVYTLPPS REEMTKNQVS

151 LTCLVKGFYP SDIAVEWESN GQPENNYKTT PPVLDSDGSF FLYSKLTVDK

201 SRWQQGNVFS CSVMHEALHN HYTQKSLSLS PGK
```

Leader Sequence Variants

While the generated constructs described above included the TPA leader sequence, alternative leader sequences may be used, such as the native leader sequence (SEQ ID NO: 22—below) or the honey bee melittin (SEQ ID NO: 24—below) leader sequences.

```
            Native:
                                    (SEQ ID NO: 22)
            MGRGLLRGLWPLHIVLWTRIAS Honey bee melittin (HBML):
                                    (SEQ ID NO: 24)
            MKFLVNVALVFMVVYISYIYA
```

Example 2. Differential Ligand Inhibition by Receptor Fusion Protein Variants in Cell-Based Assay Affinities of TGFβ1, TGFβ2 and TGFβ3 for hTβRII (G4S)2-hFc; hTβRII (G4S)3-hFc; hTβRII (G4S)4-hFc; hTβRII-hFc; and hTβRII extended hinge-hFc proteins were evaluated in vitro with a Biacore™ instrument, and the results are summarized in FIGS. 4A and 4B. Each of the fusion proteins was capable of binding TGFβ1 and TGFβ3 with high affinity, but the constructs having linker lengths longer than or equal to (G4S)4 (SEQ ID NO: 19) were surprisingly capable of binding to both TGFβ1 and TGFβ3 with higher affinity than constructs having linker lengths shorter than (G4S)4 (SEQ ID NO: 19). Binding between TGFβ2 and any of the constructs was low or transient. Deglycosylation of the constructs did not change binding.

A reporter gene assay in A549 cells was used to determine the ability of hTβRII-hFc variants to inhibit activity of TGFβ1, TGFβ2 and TGFβ3. This assay is based on a human lung carcinoma cell line transfected with a pGL3(CAGA)12 reporter plasmid (Dennler et al, 1998, EMBO 17: 3091-3100) as well as a *Renilla* reporter plasmid (pRLCMV) to control for transfection efficiency. The CAGA motif is present in the promoters of TGFβ-responsive genes (for example, PAI-1), so this vector is of general use for factors signaling through SMAD2 and SMAD3.

On the first day of the assay, A549 cells (ATCC®: CCL-18S™) were distributed in 48-well plates. On the second day, a solution containing pGL3(CAGA)12, pRLCMV, X-tremeGENE 9 (Roche Applied Science), and OptiMEM (Invitrogen) was preincubated, then added to Eagle's minimum essential medium (EMEM, ATCC®) supplemented with 0.1% BSA, which was applied to the plated cells for incubation overnight at 37° C., 5% $CO_2$. On the third day, medium was removed, and cells were incubated overnight at 37° C., 5% $CO_2$ with a mixture of ligands and inhibitors prepared as described below.

Serial dilutions of test articles were made in a 48-well plate in assay buffer (EMEM+0.1% BSA). An equal volume of assay buffer containing the test ligand was added to obtain a final ligand concentration equal to the EC50 determined previously. Human TGFβ1, human TGFβ2, and human TGFβ3 were obtained from PeproTech. Test solutions were incubated at 37° C. for 30 minutes, then a portion of the mixture was added to all wells. After incubation with test solutions overnight, cells were rinsed with phosphate-buffered saline, then lysed with passive lysis buffer (Promega E1941) and stored overnight at −70° C. On the fourth and final day, plates were warmed to room temperature with gentle shaking. Cell lysates were transferred in duplicate to a chemiluminescence plate (96-well) and analyzed in a luminometer with reagents from a Dual-Luciferase Reporter Assay system (Promega E1980) to determine normalized luciferase activity.

Figure 5A:
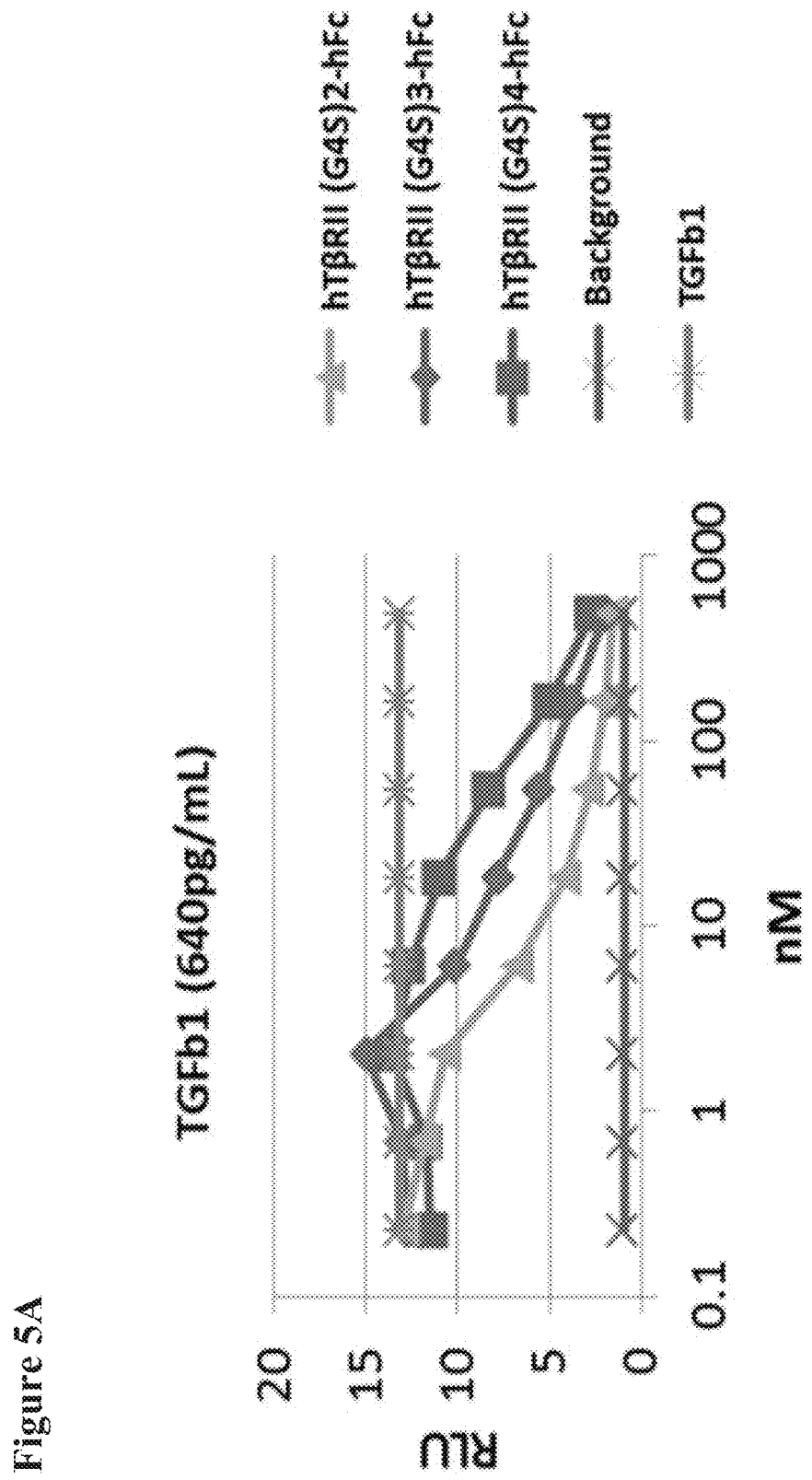
FIGS. 5A and 5C graph the results from reporter gene assays testing the affinity of TGFβ1 for one of several different TβRII-Fc fusion protein constructs.
Figure 5B:
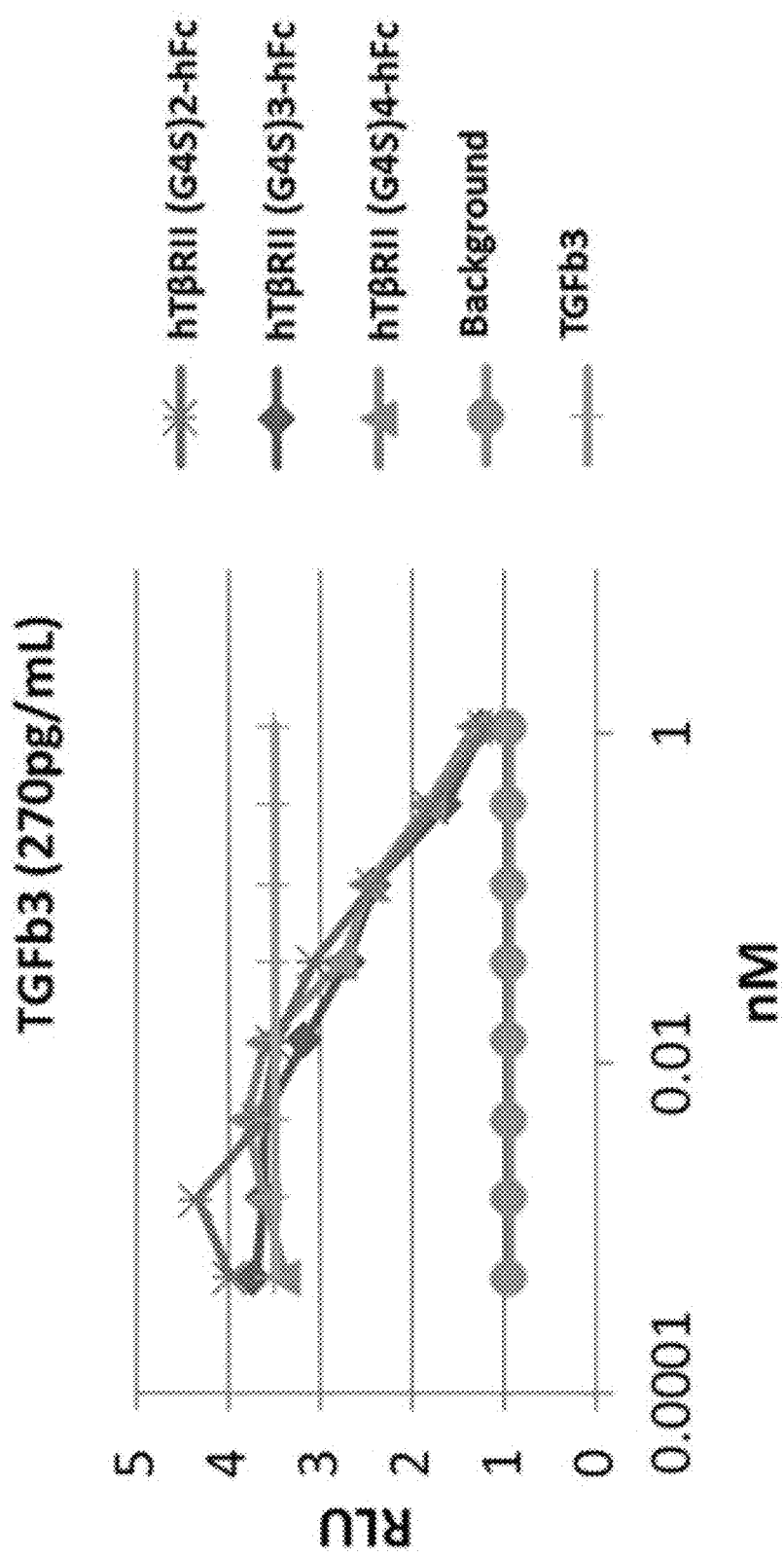
FIGS. 5B and 5D graph the results from reporter gene assays testing the affinity of the TGFβ3 for one of several different TβRII-Fc fusion protein constructs.
Figure 5C:
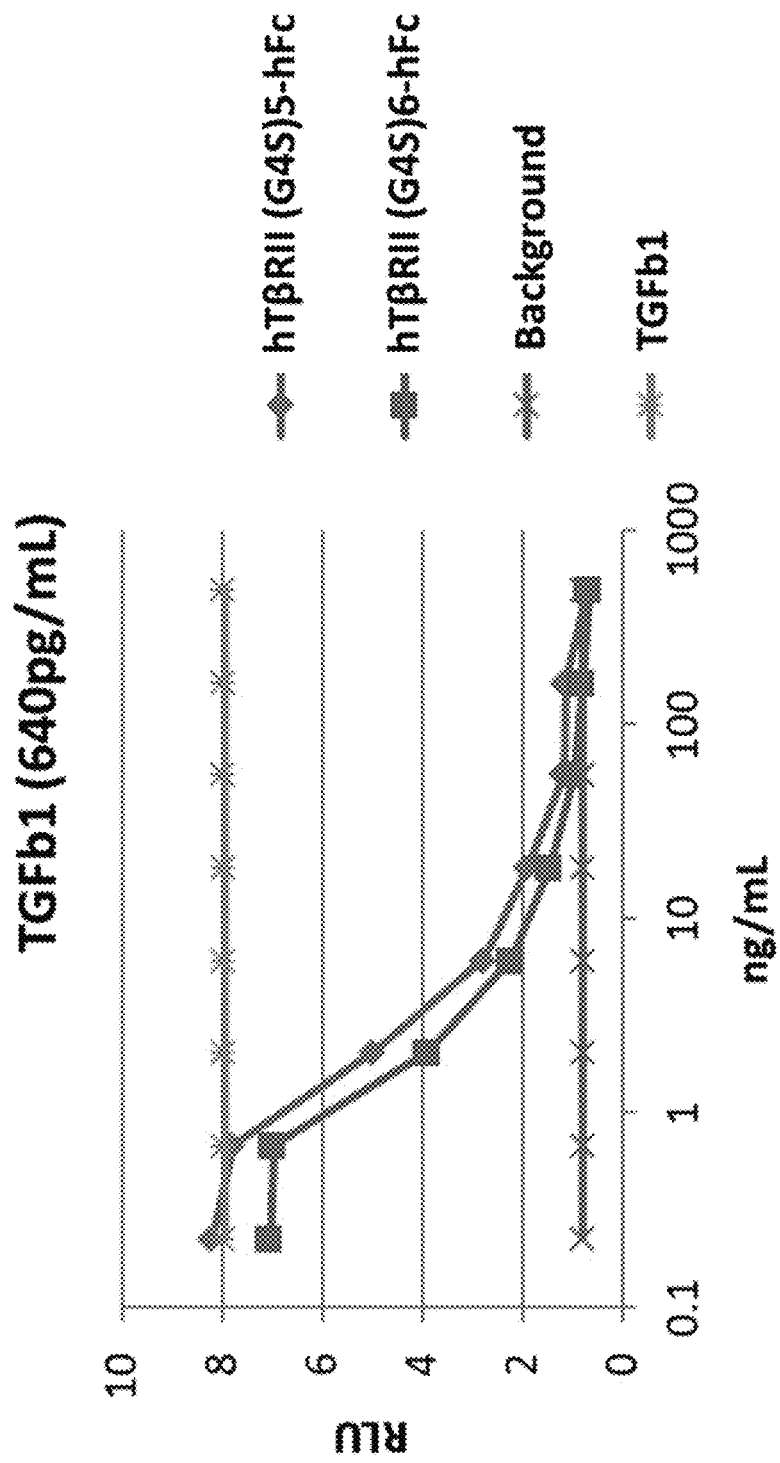
Figure 5D:
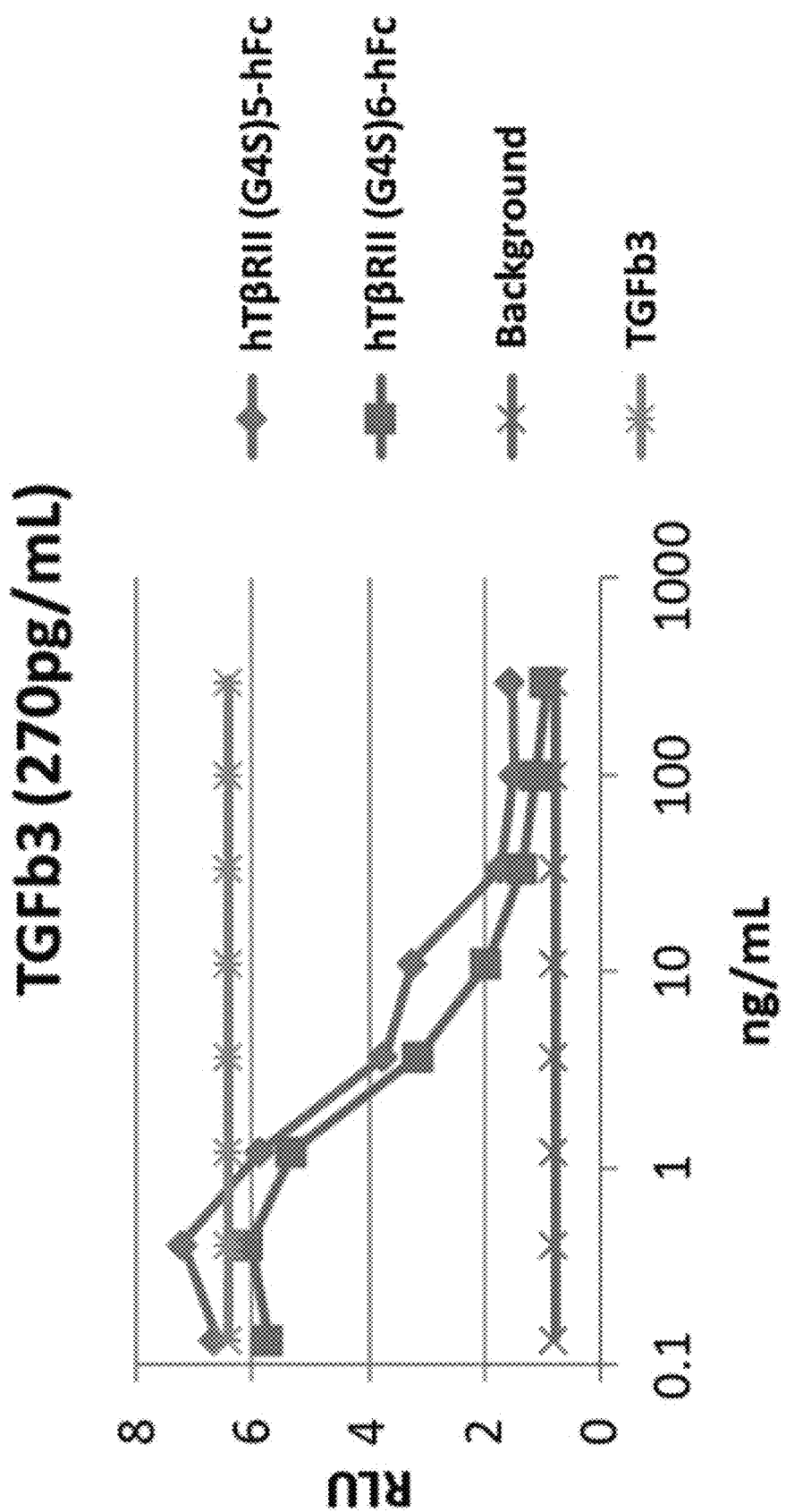

As illustrated in FIGS. 5A-5F, the hTβRII (G4S)2-hFc; hTβRII (G4S)3-hFc; hTβRII (G4S)4-hFc; hTβRII (G4S)5-hFc; hTβRII (G4S)6-hFc; hTβRII-hFc; and hTβRII extended hinge-hFc proteins all were capable of inhibiting both TGFβ1 and TGFβ3. Interestingly, while there was a correlation between improved TGFβ1 and TGFβ3 inhibition and linker length for the the hTβRII (G4S)2-hFc; hTβRII (G4S)3-hFc and hTβRII (G4S)4-hFc constructs (FIG. 5E), this improvement trend appeared to have plateaued for hTβRII (G4S)5-hFc and hTβRII (G4S)6-hFc constructs (FIG. 5F).

INCORPORATION BY REFERENCE

All publications and patents mentioned herein are hereby incorporated by reference in their entirety as if each individual publication or patent was specifically and individually indicated to be incorporated by reference.

While specific embodiments of the subject matter have been discussed, the above specification is illustrative and not restrictive. Many variations will become apparent to those skilled in the art upon review of this specification and the claims below. The full scope of the invention should be determined by reference to the claims, along with their full scope of equivalents, and the specification, along with such variations.

We claim:

1. A Transforming Growth Factor-β Receptor II (TβRII) fusion polypeptide comprising an amino acid sequence of SEQ ID NO: 13, 48 53 or 56.

2. The polypeptide of claim 1, wherein the polypeptide inhibits TGFβ1 with an $IC_{50}$ of between 0.02 nM and 0.1 nM, or wherein the polypeptide inhibits TGFβ3 with an $IC_{50}$ of between 0.02 nM and 0.05 nM, as determined using a reporter gene assay.

3. The polypeptide of claim 2, wherein the reporter gene assay is a CAGA reporter assay.

4. A pharmaceutical preparation comprising the polypeptide of claim 1 and a pharmaceutically acceptable excipient.

* * * * *

UNITED STATES PATENT AND TRADEMARK OFFICE
CERTIFICATE OF CORRECTION

PATENT NO. : 11,021,527 B2
APPLICATION NO. : 15/969957
DATED : June 1, 2021
INVENTOR(S) : Ravindra Kumar et al.

Page 1 of 1

It is certified that error appears in the above-identified patent and that said Letters Patent is hereby corrected as shown below:

In the Specification

In Column 20, Line 40, please delete:
"together by means of a (GGGGS)4 linker (SEQ ID NO: 58)"

And replace with:
--together by means of a $(GGGGS)_4$ linker (SEQ ID NO: 58)--

In the Claims

In Column 157, Line 35, please delete:
"SEQ ID NO: 13, 48 53 or 56."

And replace with:
--SEQ ID NO: 13, 48, 53 or 56.--

Signed and Sealed this
Twenty-eighth Day of December, 2021

Drew Hirshfeld
*Performing the Functions and Duties of the*
*Under Secretary of Commerce for Intellectual Property and*
*Director of the United States Patent and Trademark Office*